United States Patent
Robinson et al.

(10) Patent No.: US 12,020,794 B2
(45) Date of Patent: Jun. 25, 2024

(54) METHODS AND SYSTEMS FOR DISPENSING OPIOIDS ACCORDING TO PAIN-MODULATING REGIMEN

(71) Applicant: Green Sky Creations LLC, Seattle, WA (US)

(72) Inventors: Simon Robinson, Seattle, WA (US); Justin Esterberg, Mesa, AZ (US); Brad Douglass, Black Diamond, WA (US)

(73) Assignee: Green Sky Creations LLC, Seattle, WA (US)

(*) Notice: Subject to any disclaimer, the term of this patent is extended or adjusted under 35 U.S.C. 154(b) by 0 days.

(21) Appl. No.: 18/540,760

(22) Filed: Dec. 14, 2023

(65) Prior Publication Data

US 2024/0120055 A1    Apr. 11, 2024

Related U.S. Application Data

(63) Continuation-in-part of application No. 18/077,853, filed on Dec. 8, 2022, which is a continuation of
(Continued)

(51) Int. Cl.
*G16H 20/10* (2018.01)
*A61B 5/00* (2006.01)
(Continued)

(52) U.S. Cl.
CPC ........... *G16H 20/10* (2018.01); *A61B 5/4848* (2013.01); *A61K 9/48* (2013.01); *A61K 31/05* (2013.01); *A61K 31/352* (2013.01); *G16H 50/50* (2018.01)

(58) Field of Classification Search
CPC ...... G16H 20/10; G16H 50/50; A61B 5/4848; A61K 9/48; A61K 31/05; A61K 31/352
See application file for complete search history.

(56) References Cited

U.S. PATENT DOCUMENTS

| 2010/0249045 A1* | 9/2010 | Babul ................... A61K 31/44 514/630 |
| 2011/0097395 A1 | 4/2011 | Babul et al. |

(Continued)

FOREIGN PATENT DOCUMENTS

| WO | WO-2019165387 A1 * | 8/2019 | ............. A61K 31/01 |
| WO | 2020227440 | 11/2020 | |

OTHER PUBLICATIONS

Steinkamp JM, Goldblatt N, Borodovsky JT, LaVertu A, Kronish IM, Marsch LA, Schuman-Olivier Z Technological Interventions for Medication Adherence in Adult Mental Health and Substance Use Disorders: A Systematic Review JMIR Ment Health 2019;6(3):e12493. (Year: 2019).*

(Continued)

*Primary Examiner* — Linh Giang Le
(74) *Attorney, Agent, or Firm* — Perkins Coie LLP

(57) ABSTRACT

A method for dispensing opioids using a dispensing container in an anti-addiction pain-modulating regimen includes generating a dosage scheme for dispensing an opioid compound using the dispensing container including a controller programmable according to the dosage scheme and locked compartments storing the opioid compound. The dosage scheme includes a first dosage scheme for an opioid compound and a first dosage scheme for a cannabinoid compound to be administered to the patient concurrently over a period of time. The method includes sending the dosage scheme for operating the dispensing container. The controller stores one or more authentication programs and is programmed to authenticate the patient using the one or more authentication programs, and in response to authenticating the patient, unlock one or more of the compartments to allow the patient to access to a dosage of the opioid (Continued)

compound held in the one or more compartments according to the dosage scheme.

20 Claims, 20 Drawing Sheets

Related U.S. Application Data application No. 17/713,994, filed on Apr. 5, 2022, now Pat. No. 11,551,799, application No. 18/540,760 is a continuation-in-part of application No. 17/697,253, filed on Mar. 17, 2022, now abandoned.

(51) Int. Cl.
*A61K 9/48* (2006.01)
*A61K 31/05* (2006.01)
*A61K 31/352* (2006.01)
*G16H 50/50* (2018.01)

(56) References Cited

U.S. PATENT DOCUMENTS

| | | |
|---|---|---|
| 2012/0270895 A1 | 10/2012 | Wermeling |
| 2017/0372018 A1 | 12/2017 | Rosenblatt et al. |
| 2018/0110725 A1 | 4/2018 | Lanzkowsky |
| 2018/0228751 A1 | 8/2018 | Stott et al. |
| 2020/0005948 A1 | 1/2020 | Gupta et al. |
| 2020/0227174 A1 | 7/2020 | Rosenblatt et al. |
| 2020/0372993 A1 | 11/2020 | Chu |
| 2021/0043293 A1 | 2/2021 | Valuck et al. |
| 2023/0298718 A1 | 9/2023 | Robinson et al. |

OTHER PUBLICATIONS

Imtiaz et al. 2021, "Hypoxia driven opioid targeted automated device for overdose rescue." Scientific reports vol. 11, 1 24513. Dec. 31, 2021, doi:10.1038/s41598-021-04094-x.

Wiskerke, Joost; Stoop, Nicky; Schetters, Dustin; Schoffelmeer, Anton N M; Pattij, Tommy. "Cannabinoid CB1 Receptor Activation Mediates the Opposing Effects of Amphetamine on Impulsive Action and Impulsive Choice." PLoS ONE6.10: e25856. Public Library of Science. (Oct. 7, 2011) (Year: 2011).

\* cited by examiner

| Composition Database ||
| --- | --- |
| First Stage | Second Stage |
| 10 mg of THC and 10 mg of CBD | 20 mg of CBD and 5 mg of THC |
| 5 mg of THC and 50 mg of CBD | 30 mg of CBD and 0 mg of THC |
| 5 mg of THC and 5 mg of THCA | 50 mg CBD |
| 15 mg of CBN | 2 mg THC and 2 mg CBD |
| 25 mg delta-8 of THC | 25 mg of delta-8 THC |
| 100 mg CBG and 10 mg delta-9 THC | 50 mg CBG |
| 0 mg of THC or CBD | 20 mg delta-9 THC |
| 50 mg CBC | 50 mg THC |
| 2.5 mg delta-8 THC | 2.5 mg CBD |
| 10 mg of THCV and 10 mg CBDV | 20 mg of CBDV and 5 mg of THCV |
| 50 mg of CBGA and 10 mg CBNA | 10 mg CBNA and 10 mg CBGA |
| 5 mg of THC and 10 mg HHC | 5 mg CBD and 10 mg HHC |
| 10 mg of THC and 10 mg of CBE | 0 mg of THC and 5 mg of CBD |

*FIG. 2*

| Analgesic Database ||
|---|---|
| S. No. | Analgesic |
| 1 | Acetaminophen |
| 2 | Naproxen |
| 3 | Ibuprofen |
| 4 | Aspirin |
| 5 | Bromfenac |
| 6 | Etodolac |
| 7 | Oxaprozin |
| 8 | Loxoprofen |
| 9 | Piroxicam |
| 10 | Droxicam |
| 11 | Sulindac |
| 12 | Nalfon |

*FIG. 3*

| Bioavailability Enhancer Database ||
|---|---|
| S. No. | Bioavailability Enhancer |
| 1 | N-acylated fatty amino acid |
| 2 | Green tea catechins |
| 3 | Piperine |
| 4 | DMSO |
| 5 | Soy lecithin |

*FIG. 4*

| Pharmaceutical Composition Database ||
|---|---|
| S. No. | Pharmaceutical Composition |
| 1 | Methyl acrylate-methacrylic acid copolymers |
| 2 | Cellulose acetate phthalate (CAP) |
| 3 | Cellulose acetate succinate |
| 4 | Hydroxypropyl methyl cellulose phthalate |
| 5 | Hydroxypropyl methyl cellulose acetate succinate (hypromellose acetate succinate) |
| 6 | Polyvinyl acetate phthalate (PVAP) |
| 7 | Methyl methacrylate-methacrylic acid polymers |
| 8 | Shellac |
| 9 | Cellulose acetate trimellitate |
| 10 | Sodium alginate |
| 11 | Zein |
| 12 | Enteric coating aqueous solution (ethylcellulose, medium chain triglycerides [coconut], oleic acid, sodium alginate, stearic acid) (coated softgels) |

*FIG. 5*

| Sleep Composition Database | | |
|---|---|---|
| S. No. | Sleep Composition | |
| | Pharmaceutical Composition | Botanical Extract |
| 1 | Doxepin (Silenor) | Valerian |
| 2 | Estazolam | Rosemary |
| 3 | Eszopiclone (Lunesta) | St. John's Wort |
| 4 | Ramelteon (Rozerem) | Hawthorn |
| 5 | Temazepam (Restoril) | Chamomile |
| 6 | Triazolam (Halcion) | Hop |
| 7 | Zaleplon (Sonata) | Lavender |
| 8 | Zolpidem (Ambien, Edluar, Intermezzo, Zolpimist) | Valerian and Hops |
| 9 | Zolpidem extended release (Ambien CR) | Magnolia Bark |
| 10 | Suvorexant (Belsomra) | Passionflower |

*FIG. 6*

| Kit Database | | | | | | | | | | |
|---|---|---|---|---|---|---|---|---|---|---|
| Short-Term Pain | | | | | | | | | | |
| | 2-Days before surgery | 1-Day before surgery | Day of surgery | 1-Day Post-surgery | 2-Days Post-surgery | 3-Days Post-surgery | 4-Days Post-surgery | 5-Days Post-surgery | 6-Days Post-surgery | 7-Days Post-surgery | 8-Days Post-surgery |
| | 12/15/2020 | 12/16/2020 | 12/17/2020 | 12/18/2020 | 12/19/2020 | 12/20/2020 | 12/21/2020 | 12/22/2020 | 12/23/2020 | 12/24/2020 | 12/25/2020 and beyond |
| Opioid Dose | 0 mg | 0 mg | 25 mg of hydrocodone 4 times daily (100 mg total) | 25 mg of hydrocodone 4 times daily (100 mg total) | 20 mg of hydrocodone 4 times daily (80 mg total) | 15 mg of hydrocodone 4 times daily (60 mg total) | 10 mg of hydrocodone 4 times daily (40 mg total) | 10 mg of hydrocodone 3 times daily (30 mg total) | 10 mg of hydrocodone 2 times daily (20 mg total) | 10 mg of hydrocodone once daily (10 mg total) | 0 mg |
| Cannabinoid Dose | 25 mg of CBD 2X times daily (50 mg total) | 25 mg of CBD 4X times daily (100 mg total) | 25 mg of CBD 4X times daily (100 mg total) | 25 mg of CBD 4X times daily (100 mg total) | 30 mg of CBD 4X times daily (120 mg total) | 35 mg of CBD 4X times daily (140 mg total) | 40 mg of CBD 4X times daily (160 mg total) | 45 mg of CBD 4X times daily (180 mg total) | 50 mg of CBD 4X times daily (200 mg total) | 50 mg of CBD 4X times daily (200 mg total) | 25 – 50 mg as needed |
| Other Medications | 0 mg | 0 mg | 500 mg Acetaminophen, 300 mg ibuprofen, twice daily | 500 mg Acetaminophen, 300 mg ibuprofen, twice daily | 500 mg Acetaminophen, 300 mg ibuprofen, twice daily | 500 mg Acetaminophen, 300 mg ibuprofen, twice daily | 500 mg Acetaminophen, 300 mg ibuprofen, once daily | 500 mg Acetaminophen, 300 mg ibuprofen, once daily | 500 mg Acetaminophen, 300 mg ibuprofen, once daily | 500 mg Acetaminophen, 300 mg ibuprofen, as needed | 500 mg Acetaminophen, 300 mg ibuprofen, as needed |
| Long-Term Pain | | | | | | | | | | |
| | Week 1 | Week 2 | Week 3 | Week 4 | Week 5 | Week 6 | Week 7 | Week 8 and beyond | | | |
| Opioid Dose | 25 mg of hydrocodone 4 times daily (100 mg total) | 25 mg of hydrocodone 3 times daily (75 mg total) | 25 mg of hydrocodone 2 times daily (50 mg total) | 25 mg of hydrocodone once daily (25 mg total) | 10 mg of hydrocodone twice daily (20 mg total) | 5 mg of hydrocodone twice daily (10 mg total) | 5 mg of hydrocodone once daily (5 mg total) | 0 mg | | | |
| Cannabinoid Dose | 25 mg of CBD 4X times daily (100 mg total) | 50 mg of CBD 4X times daily (200 mg total) | 100 mg of CBD 4X times daily (400 mg total) | 150 mg of CBD 4X times daily (600 mg total) | 200 mg of CBD 4X times daily (800 mg total) | 250 mg of CBD 4X times daily (1000 mg total) | 300 mg of CBD 4X times daily (1200 mg total) | 300-500 mg of CBD 4X times daily, or as needed (2000 mg max total) | | | |
| Other Medications | 500 mg Acetaminophen, 300 mg ibuprofen, twice daily | 500 mg Acetaminophen, 300 mg ibuprofen, twice daily | 500 mg Acetaminophen, 300 mg ibuprofen, 3 times daily | 500 mg Acetaminophen, 300 mg ibuprofen, 3 times daily (as needed) | 500 mg Acetaminophen, 300 mg ibuprofen, 3-4 times daily (as needed) | 500 mg Acetaminophen, 300 mg ibuprofen, 3-4 times daily (as needed) | 500 mg Acetaminophen, 300 mg ibuprofen, 3-4 times daily (as needed) | 500 mg Acetaminophen, 300 mg ibuprofen, 3-4 times daily (as needed) | | | |

FIG. 14

| User Database | | |
|---|---|---|
| Name | Anthony | Jake |
| Gender | Male | Male |
| Age | 32 | 24 |
| Weight | 110 kgs | 65 kgs |
| Height | 6'2" | 5'8" |
| Other medical condition | Diabetic | No other condition |
| Personality | Strong | Weak |
| Disposition (1-5) | 4 | 2 |

*FIG. 16*

METHODS AND SYSTEMS FOR DISPENSING OPIOIDS ACCORDING TO PAIN-MODULATING REGIMEN

CROSS-REFERENCE TO RELATED APPLICATIONS

This application is a continuation-in-part of U.S. patent application Ser. No. 18/077,853, filed Dec. 8, 2022, which is a continuation of U.S. patent application Ser. No. 17/713,994, filed Apr. 5, 2022, now issued as U.S. Pat. No. 11,551,799, the content of each of which are incorporated herein by reference in their entireties. This application is also related to U.S. patent application Ser. No. 17/697,253, filed Mar. 17, 2022, which is incorporated herein by reference in its entirety.

TECHNICAL FIELD

The present disclosure is related to cannabinoid compositions having enhanced bioavailability. The cannabinoid compositions disclosed herein can further comprise other psychoactive ingredients and possess improved multi-stage bioavailability, physiological targeting, and delayed onset.

BACKGROUND

Food products containing edible *Cannabis* extract have emerged as a popular and lucrative facet of the legalized market for both recreational and medicinal *Cannabis*. The many formulations of *Cannabis* extracts used in edibles present a unique regulatory challenge for policy makers. Although edibles are often considered a safe, discreet, and effective means of attaining the therapeutic and/or intoxicating effects of *Cannabis* without exposure to the potentially harmful risks of *Cannabis* smoking, there has been limited research evaluating how ingestion differs from other methods of *Cannabis* administration in terms of therapeutic efficacy, subjective effects, and safety. The most prominent difference between ingestion and inhalation as routes of administration for *Cannabis* extracts and many other psychoactive plant preparations (e.g., psilocybin-containing fungi) is the delayed onset of drug-effect with ingestion. Uninitiated consumers often do not understand or expect this and may consume a greater than intended amount of the active drug before the drug has taken effect, which can result in profoundly physical or psychological adverse effects.

Accordingly, there is a need to develop cannabinoid compositions having improved, better controlled bioavailability. The compositions disclosed herein satisfy the need in the art.

SUMMARY

This disclosure relates to a formulation formulated into a single dosage form, comprising two or more compositions staged for release at different times or having different release profiles. One or more staged composition comprises one or more active agents such as cannabinoids including THC and CBD, analgesics, sleeping aids, and botanical extracts. In some embodiments, one or more staged composition may comprise one or more bioavailability enhancers. In some embodiments, the formulation is formulated into a pill, a tablet, a capsule, a topical patch, a transdermal patch, a transmucosal patch, a lozenge, or a suppository. In some embodiments, the formulation further comprises one or more coatings between the two or more staged compositions.

In a related aspect, this disclosure relates to a method of delivering compositions staged for release at different time or having different release profiles by a single administration of the formulation disclosed herein.

BRIEF DESCRIPTION OF THE DRAWINGS

FIG. 2 illustrates a composition database, according to an embodiment.

FIG. 3 illustrates an analgesic database, according to an embodiment.

FIG. 4 illustrates a bioavailability database, according to an embodiment.

FIG. 5 illustrates a pharmaceutical database, according to an embodiment.

FIG. 6 illustrates a sleep database, according to an embodiment.

FIG. 14 illustrates a software kit database, in accordance with some embodiments.

FIG. 16 illustrates a user database, in accordance with some embodiments.

DETAILED DESCRIPTION

Figure 1:
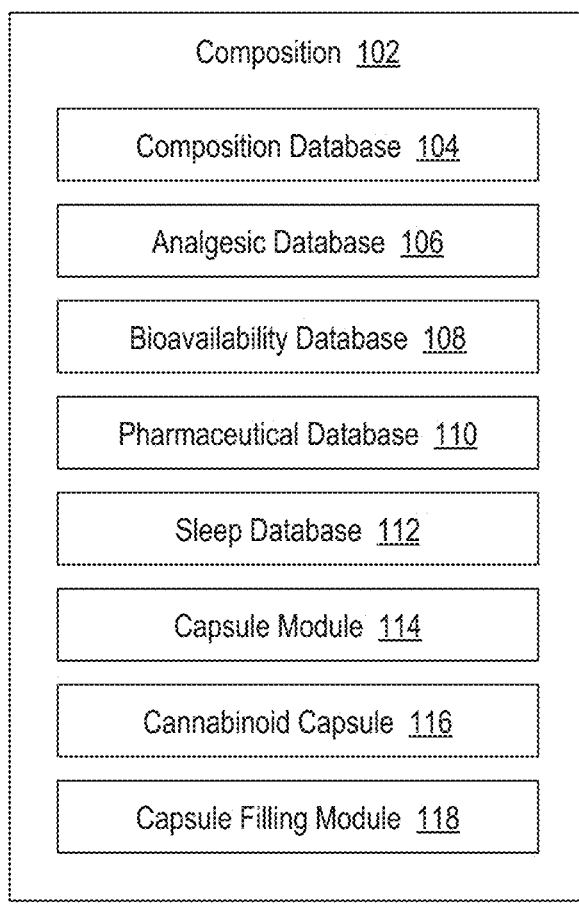
FIG. 1 illustrates a system for selecting compositions for multi-stage release of cannabinoids, according to an embodiment.

The pharmacokinetic profile of a drug substance includes absorption, which varies depending on route of administration, distribution throughout the body, metabolism by the liver and extra-hepatic tissues such as the gut microbiome, and elimination in the feces, urine, sweat, oral fluid, and hair. Often the acronym ADME is used to abbreviate these four main considerations of pharmacokinetics and pharmacology-absorption, distribution, metabolism, and elimination. Pharmacokinetic processes are dynamic, may change over time, and can be affected by the frequency and magnitude of drug exposure as well as other environmental considerations, such as what has been eaten or the physical condition of the epidermis, depending on the route of administration.

At present, it is not currently possible to administer two differing cannabinoid compositions at the same time while pre-programming selective delays in their impact on plasma levels and respective effects. For example, it may be advantageous to administer a cannabinoid treatment wherein a single dose provides a ratio of THC:CBD in a 10:1 proportion during the first hour of onset, and a ratio of THC:CBD of 1:1 during the second hour of onset. However, due to the challenges associated with the pharmacokinetics of ingested cannabinoids, simply delaying the second dose by an hour may not have the intended effect or may not maintain blood concentrations within a preferred range. Similarly, timing of dosing may present challenges for certain patients and caregivers. There exists a need for a method of introducing cannabinoid and other psychoactive compounds in which the onset and sunset of effects can be both programmed and managed using various bioavailability enhancements and triggers when administering a plurality of psychoactive compounds at once.

Disclosed herein is a means for administering a plurality of psychoactive compounds, including cannabinoid compositions, in a single dose that can have disparate, but controlled initiations of onset. In certain embodiments, a single treatment is administered to a subject to elicit various therapeutic effects, for example, alleviating pain, providing energizing effects, increasing appetite, assisting with sleep, stimulating introspection, aiding meditative practice, or some combination of the therapeutic effects of cannabinoids and other psychoactive substance, at various times and in various parts of the subject's digestive tract. In certain embodiments, the subject is a mammal. In certain embodiments, the subject is human.

In one aspect, disclosed herein is a formulation comprising two or more compositions staged for release at a different time or with different release profiles. For example, the formulation comprises a first staged composition comprising one or more active agents, and a second staged composition comprising one or more active agents, wherein the first staged composition and the second staged composition have different release profiles or staged for release at different time. For example, the active agent can be formulated for immediate release, controlled release, sustained release, or delayed release. In another example, the active agent can be embedded into different layers such that the active agent in the outer layer is released first, and then the active agent embedded in an inner layer or inside the core can only be released after the outer layer is completely or partially dissolved, degraded, or disintegrated to expose the inner layer or the core. In yet another example, the first staged composition comprises microcapsules or beadlets and the second staged composition comprises one or more large capsules or softgels that completely encapsulates the first staged composition.

The one or more active agents in the first staged composition may be the same or different from the one or more active agents in the second staged composition. For example, the first staged composition is used for alleviating pain quickly and second staged composition is used for managing or maintaining the pain state created by the first stage composition after the first stage composition is fully metabolized. The formulation provides a solution to pain management and controlling the release of a plurality of cannabinoid or other physiologically active or functional compounds in vivo. Further, the formulation helps in administering two or more distinct compositions at the same time where a later stage composition has a pre-defined time delay in entering the patient's bloodstream relative to the earlier stage composition. Various active agents can be included in the formulation for a desirable stage of release. These active agents include but are not limited to cannabinoids such as THC and CBD, analgesics such as acetaminophen, naproxen, ibuprofen, aspirin, bromfenac, etodolac, oxaprozin, loxoprofen, piroxicam, droxicam, sulindac, and nalfon, sleeping aids such as doxepin (Silenor), estazolam, eszolam, eszopiclone (Lunesta), ramelteon (Rozerem), temazepam (Restoril), triazolam (Halcion), zaleplon (Sonata), zolpidem (Ambien, Edluar, Intermezzo, Zolpimist) and zolpidem extended release (Ambien CR), and suvorexant (Belsomra), and botanical extracts such as valerian, rosemary, St. John's wort, hawthorn, chamomile, hop, lavender, valerian and hops, *magnolia* bark, and passion flower. In some embodiments, one or more staged composition comprises a bioavailability enhancer such as N-acylated fatty amino acid, green tea catechins, piperine, DMSO, and soy lecithin.

In some embodiments, the formulation is formulated in an oral dosage form including a solid oral dosage form, a liquid oral dosage form, or a combination thereof. Various oral dosage forms may be used such as a pill, a tablet, and a capsule. In some embodiments, the formulation comprising a core and at least one layer encapsulating the core, wherein the core comprises a first staged composition and the layer comprises a second staged composition. In some embodiments, the formulation comprising a core and one or more layers encapsulating the core, wherein each layer and the core comprise compositions having different release profiles or different release time thereby to obtain a multi-stage formulation. In some embodiments, the formulation comprises a coating over the core to separate the core from the encapsulating layer(s). In some embodiments, the formulation comprises one or more coatings to separate the layers. The coating can further modify the release profile of the core and each layer. In some embodiments, the thickness of the core and each layer may vary or be independently adjusted to contain various amounts of active agents and/or to achieve desirable release profiles. In some embodiments, the solid dosage form and the liquid dosage form may be combined, for example, the core is in a liquid dosage form or semi-liquid dosage form including but not limited to liquid, gel, emulsion, and the encapsulating layer is in a solid dosage form. In some embodiments, the solid dosage form may take the form of beadlets or microcapsules ensconced within a second liquid dosage form which is then encapsulated by an outer capsule material, softgel, or other coating. In some embodiments, more than one beadlet composition or type may be utilized. In some embodiments, the formulation is formulated into a topical patch comprising multiple layers, a transdermal patch comprising multiple layers or a transmucosal patch comprising multiple layers, wherein each layer is released at different time or comprises compositions of different release profiles. In some embodiments, the patch includes microcapsules or active dots embedded within one or more layers of the topical, transdermal or transmucosal patch. Other dosage forms include lozenges, suppositories, etc.

In some embodiments, the first staged composition has a first thickness or time delay and the second staged composition has a second thickness or time delay. In some embodiments, a multi-stage formulation disclosed herein comprises a first staged oral cannabinoid composition which may be present in an oil-in-water emulsion containing one or more substances that serve to enhance absorption into biological tissue (such as surfactants, amino acids, cyclodextrins, active transporters, phages), and a second staged oral composition capable of activating the bioavailability enhancement of the first staged composition. In some embodiments, the time delay between administration of the first staged composition and administration of the second staged composition may modify the bioavailability of the cannabinoid administered in the first staged composition. In some embodiments, the multi-stage formulation increases the bioavailability of a cannabinoid or another analgesic pharmaceutical by altering the physical properties of the cannabinoid through aggregation phenomena or chemically through the creation of a molecular variant of the cannabinoid. Myristoylation, palmitorylation and palmitoleoylation are examples of acylation reactions which can for example, convert nitrogen- or oxygen-containing groups into their related acylated variants (e.g., amino acids converting into N-acylated amino acids). Another example includes methylation using methylating agents such as S-adenosylmethionine (SAM-e), trimethylglycine, and tetrahydrofolate which can for example create methyl ether or methyl ester variants of the original bioactive compound. In some embodiments, the multi-stage formulation is a multi-layered pill, tablet, or capsule including a cannabinoid and a formulation that comprises bioavailability enhancers.

In some embodiments, the formulation comprises a first layer comprising a first composition, and at least a second layer comprising a second composition, wherein the second composition may contain one or more active agents, for example, active cannabinoids and the first composition may contain one or more active agents such as NSAIDs. In some embodiments, the multi-stage composition comprises a first layer comprising a first composition comprising a psychoactive compound such as dimethyltryptamine (DMT) as an active agent, and at least a second layer comprising a second composition comprising active compounds that alter the effect or metabolic response to the first composition, such as monoamine oxidase inhibitors (e.g., harmine, harmaline, quercetin, berberine).

In some embodiments, the formulation may facilitate a multilayered capsule for sleep including a cannabinoid and a bioavailability enhancing formulation. Wherein the method involves administering a capsule with at least two layers, the at least two layers comprising at least two compositions, the first composition comprising a cannabinoid (e.g., CBD) and the second composition comprising a botanical or pharmaceutical substance indicated in aiding sleep or acting on or with the first composition to accentuate, activate, or synergize with the contents of the first composition. In another embodiment, the formulated capsule may be a multi-layered capsule for sleep stages including a cannabinoid and a bioavailability enhancer. Wherein the method involves administering a capsule with at least two layers, the at least two layers comprising at least two compositions, the first composition comprised of psychoactive compounds and other botanical or therapeutic substances selected for a first sleep stage, the second composition comprised of psychoactive compounds and other botanical or therapeutic substances selected for a second sleep stage. Further, the composition 102 may determine the bioavailability enhancer or bioavailability delayer to enhance, extend or program in time the activity of the first and second stage psychoactive compound composition.

In some embodiments, the formulation may be a multi-layered pill, tablet, or capsule for aiding sleep including a cannabinoid and a bioavailability enhancing formulation. For example, the formulation comprises at least two layers, the at least two layers comprising at least two compositions, the first composition comprising a cannabinoid (e.g., CBD) and the second composition comprising a botanical or pharmaceutical substance indicated in aiding sleep or acting on or with the first composition to accentuate, activate, or synergize with the contents of the first composition. In some embodiments, the formulation comprising a cannabinoid and a bioavailability enhancer is formulated for different sleep stages. For example, the formulation comprises at least two layers, the at least two layers comprising at least two compositions, the first composition comprised of psychoactive compounds and other botanical or pharmaceutical substances selected for a first sleep stage, the second composition comprised of psychoactive compounds and other botanical or pharmaceutical substances selected for a second sleep stage. Further, the formulation further comprises one or more bioavailability enhancers to enhance the activity of the first and second stage psychoactive compound composition.

In some embodiments, a first staged composition comprises a modulator that modulates the metabolic machinery of the organism to impact the pharmacokinetics of the active agent contained in a second staged composition. The modulator may be released into the blood stream of the subject before or after release of the active agent. For example, the first staged composition may comprise a phase 1 and/or phase 2 inhibitor that is first introduced in the body prior to the introduction of a cannabinoid (e.g., delta-9 THC) into the body as a means of inhibiting the metabolism of the cannabinoid to an inactive metabolite thus maintaining a pharmacologically relevant blood concentration range of the cannabinoid in plasma for a longer duration. Phase I detoxification yields, in general, more polar and more water-soluble metabolites, but that may retain pharmacological activity by often adding an oxygen-functional group to a lipophilic substance. Many of the end products of phase I detoxification also become substrates for phase II detoxification. Examples of phase I transformations include oxidation, reduction and hydrolysis reactions. Phase II detoxification yields a large polar metabolite by adding endogenous hydrophilic groups to form water-soluble inactive compounds that can be excreted by the body. Examples of phase II transformations include methylation, glucuronidation, acetylation, sulfation, etc. Delta-9 THC is lipophilic and quickly undergoes phase 1 detoxification to 11-hydroxy-delta-9 THC in the liver. 11-hydroxy-delta-9 THC is still active at CB1 receptors and can undergo further phase 1 detoxification-a second oxidative step-into 11-nor-carboxy-delta-9-THC, which is not active at CB1 receptors. Both 11-hydroxy and 11-nor-carboxy THC metabolites are then glucuronidated (phase II) before they are excreted from the body in urine. (See www.ncbi.nlm.nih.gov/books/NBK544353/.) Specific phase 1 inhibitors and inducers can be used to tailor what drug metabolizing reactions take place such that one can either accelerate or decelerate the half-life of an active substance or metabolite. Various subclasses of the super-family of cytochrome P450 (CYP) enzymes can be targeted including CYP1A2, CYP2B6, CYP2C8, CYP2C9, CYP2C19, CYP2D6, CYP3A4/5, and others. Inhibitors of CYP enzymes include piperine, narigenin, caffeine, niacin, bergamottin, and *Hypericum perforatum* (St. John's Wort), *Allium sativum* (garlic), *Curcuma longa* (turmeric). Inducers of CYP enzymes include berberine, St. John's Wort, ethanol, and others including various drug substances (Hakkola et al., "Inhibition and induction of CYP enzymes in humans: an update," Archives of Toxicology 94: 3671-3722 (2020)). In another example, a first staged composition comprises a monoamine oxidase inhibitor, and a second staged composition comprises a tryptamine, such as psilocin, psilocybin, dimethyltryptamine, or 5-MeO-dimethyltryptamine. In another example, a first stage composition comprises a monoamine oxidase inducer and a second stage composition comprises a phenethylamine, such as amphetamine, methylenedioxymethamphetamine, or 4-bromo-2,5-dimethoxyphenethylamine.

In some embodiments, the formulation disclosed herein may facilitate a multi-layered topical, transdermal or transmucosal delivery of a cannabinoid and/or psychoactive substance with targeted bioavailability enhancement or an altered metabolic response. In some embodiments, this disclosure relates to a topical patch, a transdermal patch or mucosal pouch, which comprises at least two layers, each layer comprising one of at least two compositions, wherein a first composition contains a cannabinoid and/or psychoactive, and a second composition contains a bioavailability enhancer.

FIG. 1 illustrates a composition system 102 for multi-stage release of cannabinoids, according to an embodiment. The composition system 102 may also utilize a composition database 104 containing composition data, including the first staged and second staged compositions and their quantity (e.g., quantity measured in mg). In one embodiment, the composition system 102 may be coupled to an analgesic database 106 to add analgesic or non-steroidal anti-inflammatory substances in the other cannabinoid or psychoactive compound composition. In another embodiment, the composition system 102 may be coupled to a sleep composition database 112 to pair a sleep composition with the cannabinoid or other psychoactive compound composition. In one case, a plurality of compositions 102 might be available and the practitioner may recommend a particular composition from the composition system 102 to the subject. In another case, the composition may be customized for each subject by the practitioner based on the sleep stages of the subject. For example, the two-stage cannabinoid composition is formulated from the first staged composition (i.e., e.g., 10 mg of THC and 10 mg of CBD, 100 mg of ibuprofen) and a bioavailability enhancer (e.g., N-acylated fatty amino acid) and second staged composition (e.g., 5 mg of THC and 50 mg of CBD, 100 mg of acetaminophen) and a second bioavailability enhancer (e.g., piperine). Further, embodiments may utilize the composition database 104, which may include different cannabinoid compositions for the first and second staged compositions. Further, embodiments may utilize the analgesic or non-steroidal anti-inflammatory drugs (NSAID) database 106, which may be coupled to the capsule formulation engine module 114. Further, analgesic compounds may be used with the first staged composition, second staged composition, or in both stages. For example, the analgesic compounds may be acetaminophen, naproxen, ibuprofen, aspirin, Bromfenac, Etodolac, Oxaprozin, Loxoprofen, Piroxicam, Droxicam, Sulindac, Nalfon.

Further, embodiments may include a bioavailability enhancer database 108, which may be coupled to the capsule formulation module 114. Further, embodiments may include a formulation database 110, which may be coupled to the capsule formulation module 114. Further, embodiments may include the sleep composition database 112, which may be coupled to the capsule formulation module 114 to add a sleep composition in the cannabinoid composition. Further, embodiments may include the capsule formulation module 114 which formulates a cannabinoid capsule for the subject. Further, embodiments may include a cannabinoid capsule 116 which is an example of an article of manufacture which may include the composition 102. The cannabinoid capsule 116 including an interior capsule which is enclosed within an exterior capsule such that when the cannabinoid capsule 116 is ingested, it will first dissolve the exterior capsule, releasing a first staged cannabinoid composition and the interior capsule, and after a period of time the interior capsule will dissolve releasing a second staged cannabinoid composition. Further, embodiments may include a capsule filling module 118 which is the process by which a cannabinoid capsule 116 is assembled wherein an interior capsule is filled with a second staged cannabinoid composition and is sealed before being inserted into an exterior capsule filled with a first staged cannabinoid composition after which the exterior capsule is sealed. Example composition systems, components, and databases (e.g., engines) are discussed in connection with FIGS. 10-11.

FIG. 2 illustrates the composition database 104, which may include different cannabinoid or and/or psychoactive compositions for the first and second staged compositions. In one embodiment, the first and second staged cannabinoid and/or psychoactive composition may be released inside the human body according to the level of pH of the digestive tract of the human body. In an exemplary embodiment, the first staged compositions may be absorbed in the stomach having pH level 6.5 to 7.5 and the second staged compositions may be absorbed in the large or small intestine having pH level 4-10. In another embodiment, the release of the first and second staged cannabinoid composition may be a timed event. Further, the cannabinoid or and/or psychoactive composition may be released in capsule form wherein the first staged composition may be an outer coating or shell of composition. The second staged composition may be an internal composition to the capsule. In another embodiment, the cannabinoid or and/or psychoactive composition may be released in the transdermal patch form. In yet another embodiment, the cannabinoid or and/or psychoactive composition may be released in oral lozenge form. In yet another embodiment, the cannabinoid or and/or psychoactive composition may be released in suppository form. In yet another embodiment, a new form factor having a bead inside the capsule may be used for the release of two-stage cannabinoid composition. In one embodiment, the first composition may be the outer layer of the capsule, the inner liquid contents of the capsule, and the second composition may be a bead or beads floating inside the liquid contents of the capsule. In another embodiment, one of at least two compositions may be released based on the sleep stage detected from a wearable device. Further, the composition database 104 may be coupled to a capsule formulation module 114.

FIG. 3 illustrates the analgesic database 106, which may be coupled to the capsule formulation module 114. Further, an analgesic may be used with the first staged composition, second staged composition, or in both stages. For example, the analgesic may be acetaminophen, naproxen, ibuprofen, aspirin, Bromfenac, Etodolac, Oxaprozin, Loxoprofen, Piroxicam, Droxicam, Sulindac, Nalfon.

FIG. 4 illustrates the bioavailability enhancer database 108, which may be coupled to the capsule formulation module 114. In one embodiment, the bioavailability enhancer may be selected based on the desired bioavailability of the cannabinoid. In another embodiment, the bioavailability enhancer may be selected based on the delivery method for the cannabinoid composition. The delivery method may include sublingual, oral, inhalable, suppository and topical. In yet another embodiment, the bioavailability enhancer may be selected based on other factors. The other factors may include taste, the potential for allergies, side-effects, and price. Further, the bioavailability enhancer database 108 may store information related to bioavailability enhancers used in two-stage compositions. For example, the bioavailability enhancer may be N-acylated fatty amino acid, green tea catechins, piperine, DMSO, soy lecithin, amongst others.

FIG. 5 shows a formulation database 110, which may be coupled to the capsule formulation module 114. Further, the formulation may only be used with the first staged composition for delaying the release of the first staged composition. Further, the formulation database 110 may store information related to the ingredients and compositions used in the first staged composition. For example, the composition may comprise substances that support functions such as extended/controlled release and enteric coatings such as, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, enteric coating aqueous solution (ethylcellulose, medium chain triglycerides [coconut], oleic acid, sodium alginate, stearic acid) (coated softgels).

FIG. 6 illustrates the sleep composition database 112, which may be coupled to the capsule formulation module 114 to add sleep composition in the cannabinoid composition. For example, the sleep compositions may comprise extracts or other preparations of botanicals, such as Valerian, Rosemary, St. John's Wort, Hawthorn, Chamomile, Hops, Lavender, Magnolia Bark, and Passionflower. Further, the composition may comprise Doxepin (Silenor), Estazolam, Eszopiclone (Lunesta), Ramelteon (Rozerem), Temazepam (Restoril), Triazolam (Halcion), Zaleplon (Sonata), Zolpidem (Ambien, Edluar, Intermezzo, Zolpimist), Zolpidem extended release (Ambien CR), Suvorexant (Belsomra).

Figure 7:
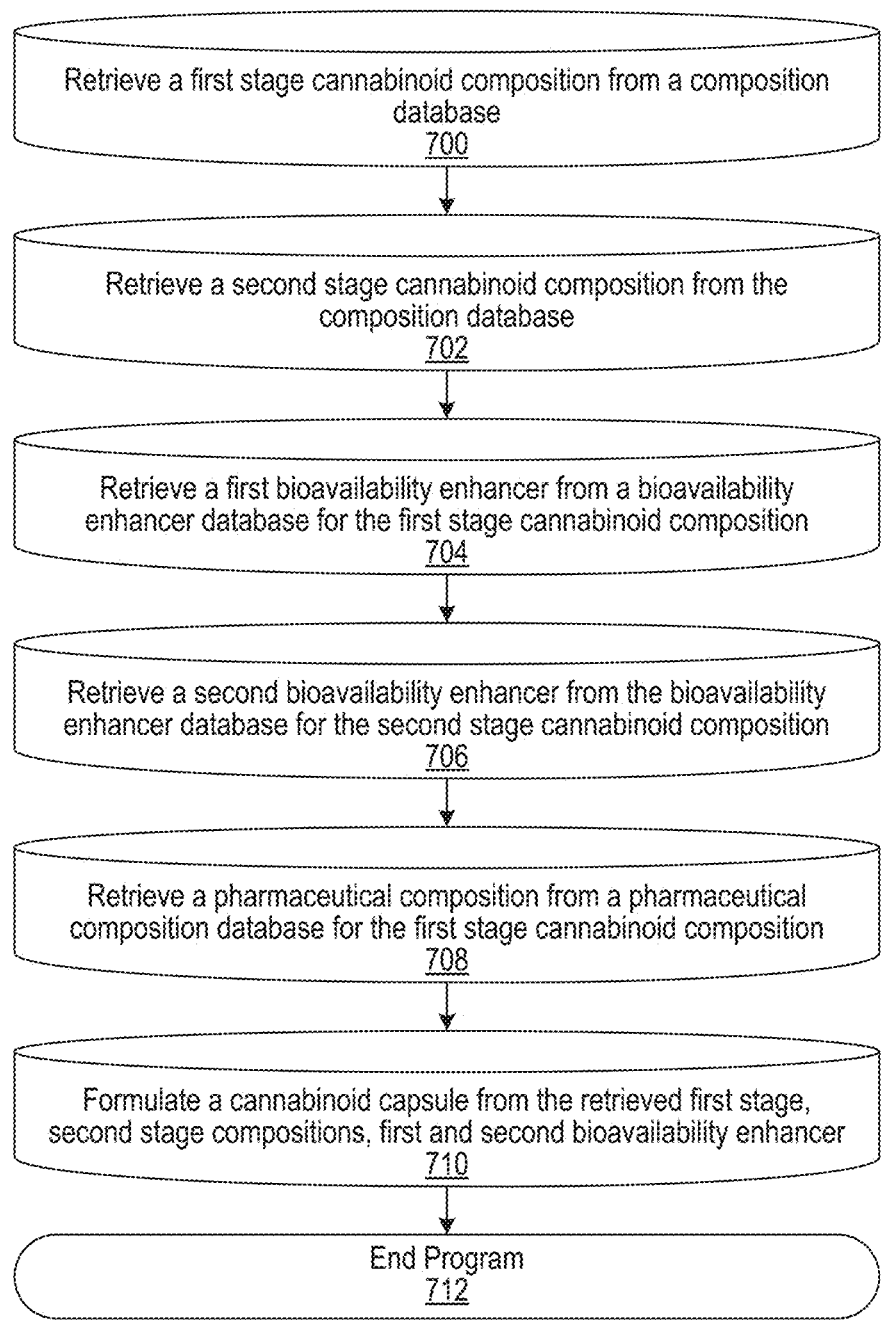
FIG. 7 illustrates a flowchart showing a method for formulating a capsule, according to an embodiment.

FIG. 7 illustrates a flowchart of a method for formulating a capsule, according to an embodiment. Embodiments may use the capsule module 114, to formulate a cannabinoid or and/or psychoactive capsule for the subject by selecting specific excipients and other nonactive ingredients that are compatible with the active ingredients. The method can be used for personalized healthcare to, for example, provide patient-specific compositions, or composition form based on, for example, the patient's health status, electronic medical records, physician input, etc. A healthcare provider can design formulations for achieving target personalized outcomes.

At first, the capsule formulation module 114 may retrieve a first staged cannabinoid or and/or psychoactive composition from the composition database 104. The cannabinoid or and/or psychoactive composition can be selected based on the patient's condition, sensitivity to active agents, etc. For example, the capsule formulation module 114 retrieves the first staged cannabinoid or and/or psychoactive composition i.e., 10 mg of THC and 10 mg of CBD or 20 mg of psilocybin from the composition database 104. In one embodiment, the capsule formulation module 114 may add an analgesic or NSAID composition from the analgesic database 106 to the first staged cannabinoid composition. For example, the capsule formulation module 114 adds 100 mg of ibuprofen from the analgesic database 106 to the first staged cannabinoid composition. Further, the capsule formulation module 114 may retrieve a second staged cannabinoid composition from the composition database 104. For example, the capsule formulation module 114 retrieves the second staged cannabinoid composition i.e., 5 mg of THC and 50 mg of CBD from the composition database 104. In one embodiment, the capsule formulation module 114 may add an analgesic or NSAID composition from the analgesic database 106 to the second staged cannabinoid or and/or psychoactive composition. For example, the capsule formulation module 114 adds 100 mg of acetaminophen from the analgesic database 106 to the second staged cannabinoid composition. Further, the capsule formulation module 114 may retrieve a first bioavailability enhancer from the bioavailability enhancer database 108 for the first staged cannabinoid composition. For example, the capsule formulation module 114 retrieves the bioavailability enhancer i.e., N-acylated fatty amino acid from the bioavailability enhancer database 108 as an effective adjuvant to the first staged cannabinoid or and/or psychoactive composition. Further, the capsule formulation module 114 may retrieve a second bioavailability enhancer from the bioavailability enhancer database 108 for a second staged cannabinoid or and/or psychoactive composition. For example, the capsule formulation module 114 retrieves the bioavailability enhancer i.e., piperine from the bioavailability enhancer database 108 for second staged cannabinoid composition. Further, the capsule formulation module 114 may retrieve the formulation from the formulation database 110 for the first staged cannabinoid composition. For example, the capsule formulation module 114 retrieves the controlled-release ingredient(s) e.g., cellulose acetate phthalate (CAP) or formulation from the formulation database 110 for delaying the absorption/dissolution of the first staged cannabinoid composition. In one embodiment, the formulation may be used for delaying the release/absorption/dissolution of the first layer (e.g., cellulose acetate phthalate (CAP)). Further, the capsule formulation module 114 may formulate a cannabinoid capsule from the retrieved first staged and second staged compositions and first and second bioavailability enhancer. For example, the capsule formulation module 114 formulates the cannabinoid capsule with the first staged composition i.e., 10 mg of THC and 10 mg of CBD, 100 mg of ibuprofen, first bioavailability enhancer N-acylated fatty amino acid and pharmaceutical composition cellulose acetate phthalate (CAP) and second staged composition i.e., 5 mg of THC and 50 mg of CBD, 100 mg of acetaminophen, second bioavailability enhancer piperine. In one embodiment, the capsule formation module 114, may formulate the cannabinoid capsule with the formulation. For example, the capsule formation module 114 formulates the cannabinoid capsule with cellulose acetate phthalate (CAP). In one example embodiment, the first composition is slowly released as the subject begins to digest the first layer. The subject may begin to feel the effects of the first composition within 30-45 minutes. As the oral capsule transits the digestive tract, the first layer eventually completely dissolves, whereupon the second layer is exposed and the contents of the second layer begin to diffuse into digestive fluids, and then the subject's body begins to absorb the second composition into the blood stream, or the second composition merely actuates its intended effect in the digestive tract without absorption into the body or blood. The subject may begin to feel the effects of the second composition approximately 1.5-2 hours after ingesting the first capsule. The oral capsule may be useful for treating acute pain quickly (via the first composition), as well as preventing the pain from returning after the first composition is fully metabolized (via the second composition). In one example embodiment, the capsule formulation module 114 may utilize the sleep composition database 112 to add sleep composition in the cannabinoid and/or psychoactive composition. Thereafter, the program ends.

Figure 8:
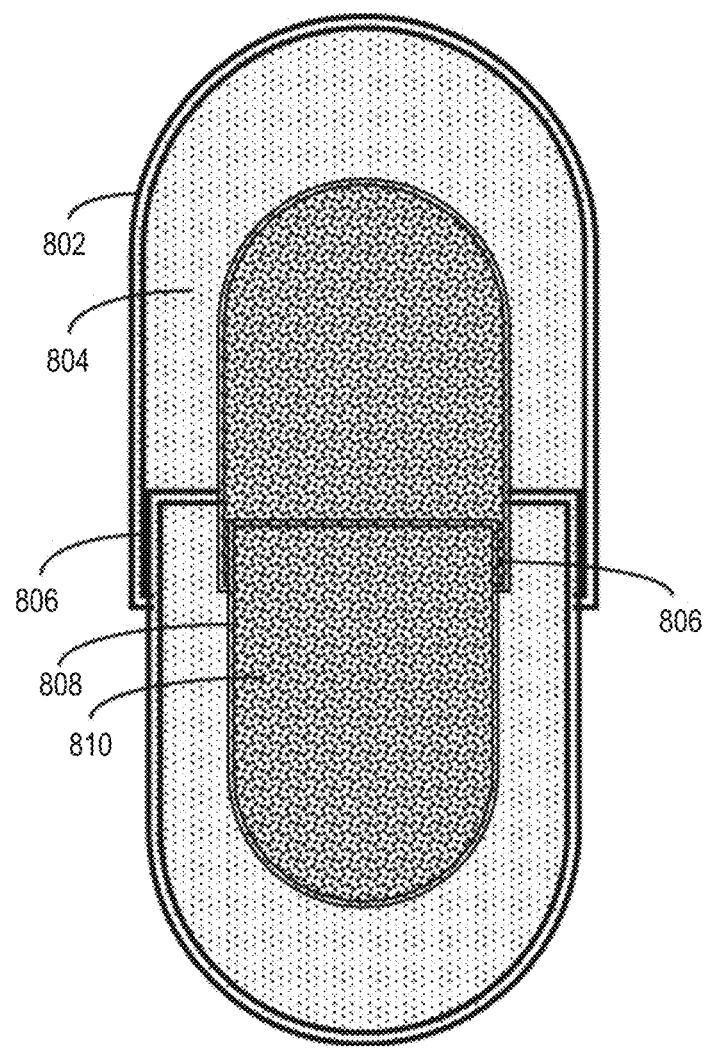
FIG. 8 illustrates a cannabinoid capsule, according to an embodiment.

FIG. 8 illustrates an example of a cannabinoid capsule 116, which is an example of a dual-stage capsule containing a first and a second cannabinoid composition. The exterior capsule wall 802 is a water-soluble shell typically comprised of gelatin or a material derived from collagen or cellulose which encapsulates a first staged cannabinoid composition 804. The exterior capsule wall 802 will dissolve in the digestive track when ingested and will release the first staged cannabinoid composition 804 contained within. The thickness of the exterior capsule wall 802 may be uniform or varied such as to control the rate at which the first staged cannabinoid composition 804 is released, and similarly when the interior capsule wall 808 is exposed to the digestive track and can be dissolved similarly. The exterior capsule wall 802 can be made thicker or incorporate additives to slow the rate at which it dissolves to delay the release of the first staged cannabinoid composition 804 or be made thinner to increase the rate at which the first staged cannabinoid composition 804 is released. The first staged cannabinoid composition 804 is a formulation of at least one cannabinoid and at least one pharmaceutical compound intended to improve the characteristics of the at least one cannabinoid, such as improving its bioavailability or complementing the desired therapeutic effects. The first staged cannabinoid composition 804 is intended for initial release to achieve a desired therapeutic effect intended to precede a second therapeutic effect to be achieved by a second staged cannabinoid composition 810. Alternatively, the first staged cannabinoid composition 804 may initiate a desired therapeutic effect which will be maintained by a second staged cannabinoid composition 810 to be released after a delay. The first staged cannabinoid composition 804 may additionally contain compounds to delay the release of either the first staged cannabinoid composition 804 or the second staged cannabinoid composition 810 by protecting the interior capsule wall 808 from being exposed to the digestive track. An example of a first staged cannabinoid composition may be a mixture of THC and CBD in a ratio of 10:1 and a ratio of cannabinoids to acetaminophen in a ratio of 1:1, such that the acetaminophen is the additive. The capsule seal 806 is where two overlapping halves of either an exterior capsule wall 802 or an interior capsule wall 808 meet and engage one another. The capsule seal 806 is typically achieved by the two halves being pressed together, creating a friction fit, by creating a mechanical indentation around the circumference of the capsule where the two halves overlap, or by adding an adhesive material to chemically bond the two capsule halves when they are pressed together. The interior capsule wall 808 is a smaller version of the exterior capsule wall 802. The interior capsule wall 808 may be comprised of similar materials as the exterior capsule wall 802 such as gelatin or a material derived from collagen or cellulose which encapsulates a second staged cannabinoid composition 804. The interior capsule wall 808 may vary in thickness or composition to achieve the desired delay and rate of release and may have different characteristics than the exterior capsule wall 802. The second staged cannabinoid composition 810 is a formulation of at least one cannabinoid and at least one pharmaceutical compound intended to improve the characteristics of the at least one cannabinoid, such as improving its bioavailability or complementing the desired therapeutic effects. The second staged cannabinoid composition 810 is typically different than the first staged cannabinoid composition 804, although they can be the same but intended to be released after a delay so as to facilitate the administration of a second dose of the first staged cannabinoid composition 804 following a delay. The second staged cannabinoid composition 810 may be comprised of the same cannabinoids and additives as the first staged cannabinoid composition 804 but in different ratios. For example, the first staged cannabinoid composition 804 may contain THC and CBD in a ratio of 10:1 while the second staged cannabinoid composition 810 may contain THC and CBD in a ratio of 1:1. Alternatively, different cannabinoids or additives may be included in the second staged cannabinoid composition 810 than in the first staged cannabinoid composition 804.

Figure 9:
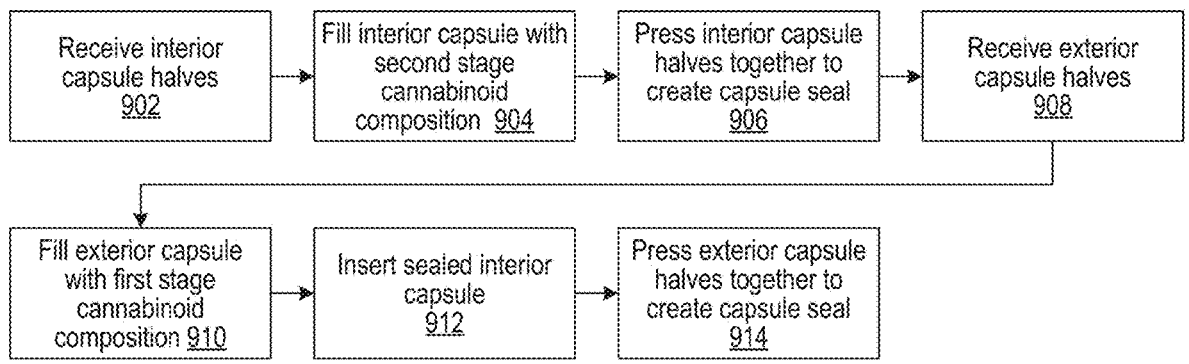
FIG. 9 illustrates a flowchart showing a method for manufacturing capsule filling module, according to an embodiment.

Further, embodiments may include the capsule filling module 118, shown as FIG. 9, which describes a method of filling a cannabinoid and/or psychoactive capsule. The process begins by receiving at step 902, a top and bottom half of an interior capsule. The interior capsule being smaller in size than the exterior capsule such that the interior capsule, or many interior capsules such as microencapsulated beadlets, can fit within the exterior capsule in addition to a first staged cannabinoid composition. In an embodiment, the interior capsule shells are made of gelatin. Filling at step 904, the bottom half of the interior capsule with a measured dose of the second staged cannabinoid composition. The second staged cannabinoid composition containing at least one cannabinoid and an additive. In an embodiment, the interior capsule being filled with a second staged cannabinoid composition comprised of THC and CBD in a ratio of 1:1 and acetaminophen as an additive. Pressing at step 906, the halves of the filled interior capsule together such that the top and bottom halves of the interior capsule are firmly held in place by friction. In an embodiment, an indentation may be made along the overlapping portion of the top and bottom halves of the interior capsule to create a crimp, improving the reliability of the seal of the interior capsule. In an alternate embodiment, an adhesive may be applied to the exterior of the bottom half of the interior capsule such that when pressed together, the top half of the interior capsule slides over the bottom half of the interior capsule contacting the adhesive. Receiving at step 908, a top and bottom half of an exterior capsule. The exterior capsule being sufficiently larger in size than the sealed interior capsule such that the interior capsule can fit within the exterior capsule in addition to a first staged cannabinoid composition. In an embodiment, the exterior capsule halves are made of gelatin. Filling at step 910, the bottom half of the exterior capsule with a measured dose of the first staged cannabinoid composition. The first staged cannabinoid composition containing at least one cannabinoid and an additive. In an embodiment, the exterior capsule being filled with a first staged cannabinoid composition comprised of THC and CBD in a ratio of 10:1 and acetaminophen as an additive. The top half of the exterior capsule may additionally be filled. The first staged cannabinoid composition may be pressed into both the top and bottom halves of the exterior capsule to create a void located centrally within the exterior capsule sufficient to accommodate a sealed interior capsule. Inserting at step 912, a sealed interior capsule into the filled exterior capsule. The interior capsule being inserted into the void created in the first staged cannabinoid composition filling the bottom half of the exterior capsule. Pressing at step 914, the halves of the filled exterior capsule together such that the top and bottom halves of the interior capsule are firmly held in place by friction. The sealed exterior capsule fully encapsulating the first staged cannabinoid composition and a sealed interior capsule. In an embodiment, an indentation may be made along the overlapping portion of the top and bottom halves of the interior capsule to create a crimp, improving the reliability of the seal of the exterior capsule. In an alternate embodiment, an adhesive may be applied to the exterior of the bottom half of the exterior capsule such that when pressed together, the top half of the exterior capsule slides over the bottom half of the exterior capsule contacting the adhesive. In an alternate embodiment, the shell of the interior capsules can be formed concurrently with loading the interior capsules with active and inactive ingredients via sol-gel processes that precipitate microspheres upon changing the viscosity of the solution(s). In an alternate embodiment, the shell of the interior capsules can be formed concurrently with loading the interior capsules with active and inactive ingredients by utilizing a double nozzle system that produces concentric spheres of active ingredients and encapsulation formulations where the latter engulfs the former to produce a stable microsphere or beadlet.

Figure 10:
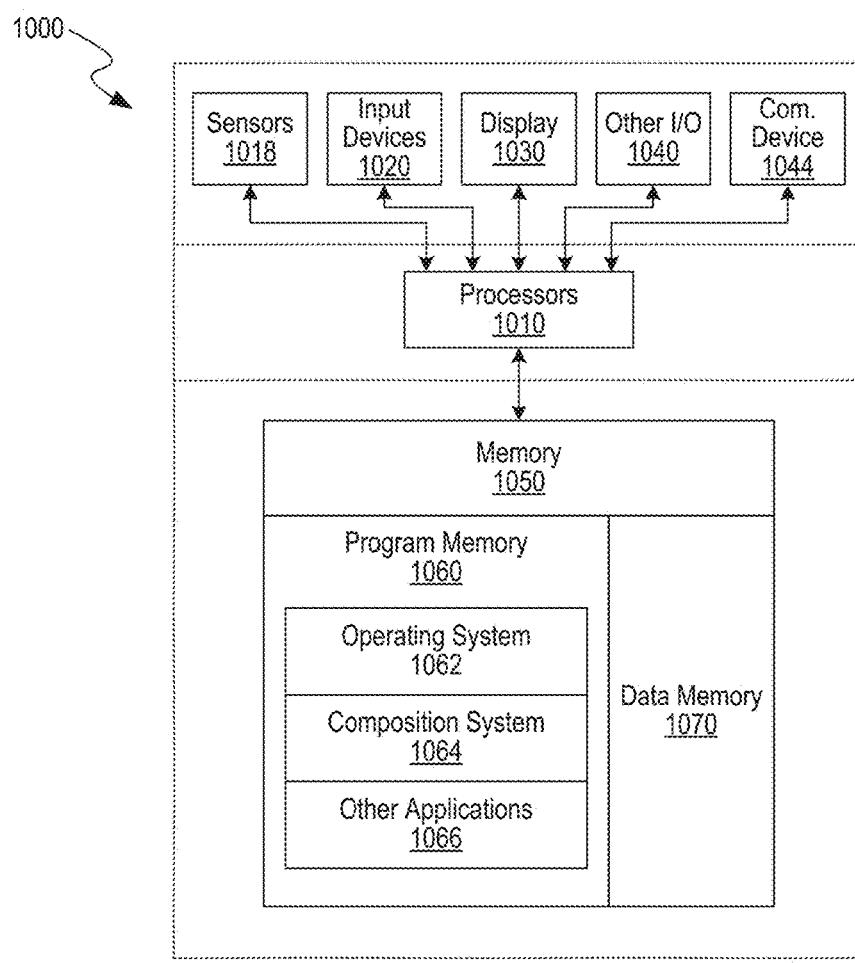
FIG. 10 is a block diagram illustrating an overview of a system on which some implementations of the disclosed technology can operate, according to an embodiment.

FIG. 10 is a block diagram illustrating an overview of a system 1000 in accordance with embodiments of the disclosed technology. The system 1000 can be used to, for example, perform all or some of the steps discussed in connection with FIGS. 7 and 12 and can be a component (e.g., a controller) of a manufacturing system for manufacturing capsules discussed in connection with FIG. 9. The system 1000 can include one or more sensors 1018 and input devices 1020 that provide input to the processor(s) 1010 (e.g., CPU(s), GPU(s), HPU(s), etc.), notifying the processor(s) of, for example, event(s), operation, and/or actions. The input can be mediated by a hardware controller that interprets the signals received from the input device and communicates the information to the processors 1010 using a communication protocol. The events can include, without limitation, user input events, new available data events, formulation modification events, manufacturing events, or the like.

The processors 1010 can be a single processing unit or multiple processing units in a device or distributed across multiple devices. The processors 1010 can be coupled to other hardware devices, for example, with the use of a bus, such as a PCI bus or SCSI bus. The processors 1010 can communicate with a hardware controller for devices, such as for a display 1130. Display 1030 can be used to display text, graphics, chemical structures, formulation data, manufacturing data, etc. In some implementations, display 1030 provides graphical and/or textual visual feedback (e.g., formulation analytics, formulation efficacy projections, available user data, dosage information, dosing schedules, etc.). In some implementations, display 1030 includes the input device as part of the display, such as when the input device is a touchscreen. Examples of display devices are: an LCD display screen, an LED display screen, a projected or augmented reality display. Other I/O devices 1040 can also be coupled to the processor, such as user devices, biometric device, monitoring equipment, network card, video card, audio card, USB, firewire or other external device. The system 1000 also includes a communication device 1040 capable of communicating wirelessly or wire-based with a network node. The communication device can communicate with another device or a server through a network using, for example, TCP/IP protocols to acquire information, such as information discussed in connection with FIGS. 1-9. The system 1000 can utilize the communication device to distribute operations across multiple network devices.

The processors 1010 can access memory 1050 in a device or distributed across multiple devices. A memory includes one or more of various hardware devices for volatile and non-volatile storage and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 1050 can include program memory 1060 that stores programs and software, such as an operating system 1062, formulation or composition system 1064 ("composition system 1064"), and other application programs 1066. Memory 1050 can also include data memory 1070, e.g., authentication information, database access information, configuration data, settings, user options or preferences, etc., which can be provided to the program memory 1050 or any element of the system 1000.

The system 1000 be configured for machine learning model(s). The machine learning models can be of various types, such as Convolutional Neural Networks (CNNs), other types of neural networks (e.g., fully connected), decision trees, forests of classification trees, Support Vector Machines, etc. Machine learning models can be trained to produce particular types of results, operations, etc. For example, a training procedure can include obtaining suitable training items with input associated with a result, applying each training item to the model, and updating model parameters based on comparison of model result to training item result. The machine learning model(s) can be generated by, for example, the cloud system using data from databases. Example machine learning models are discussed in connection with FIG. 12 and can design compositions, identify correlations between compositions, etc.

Figure 11:
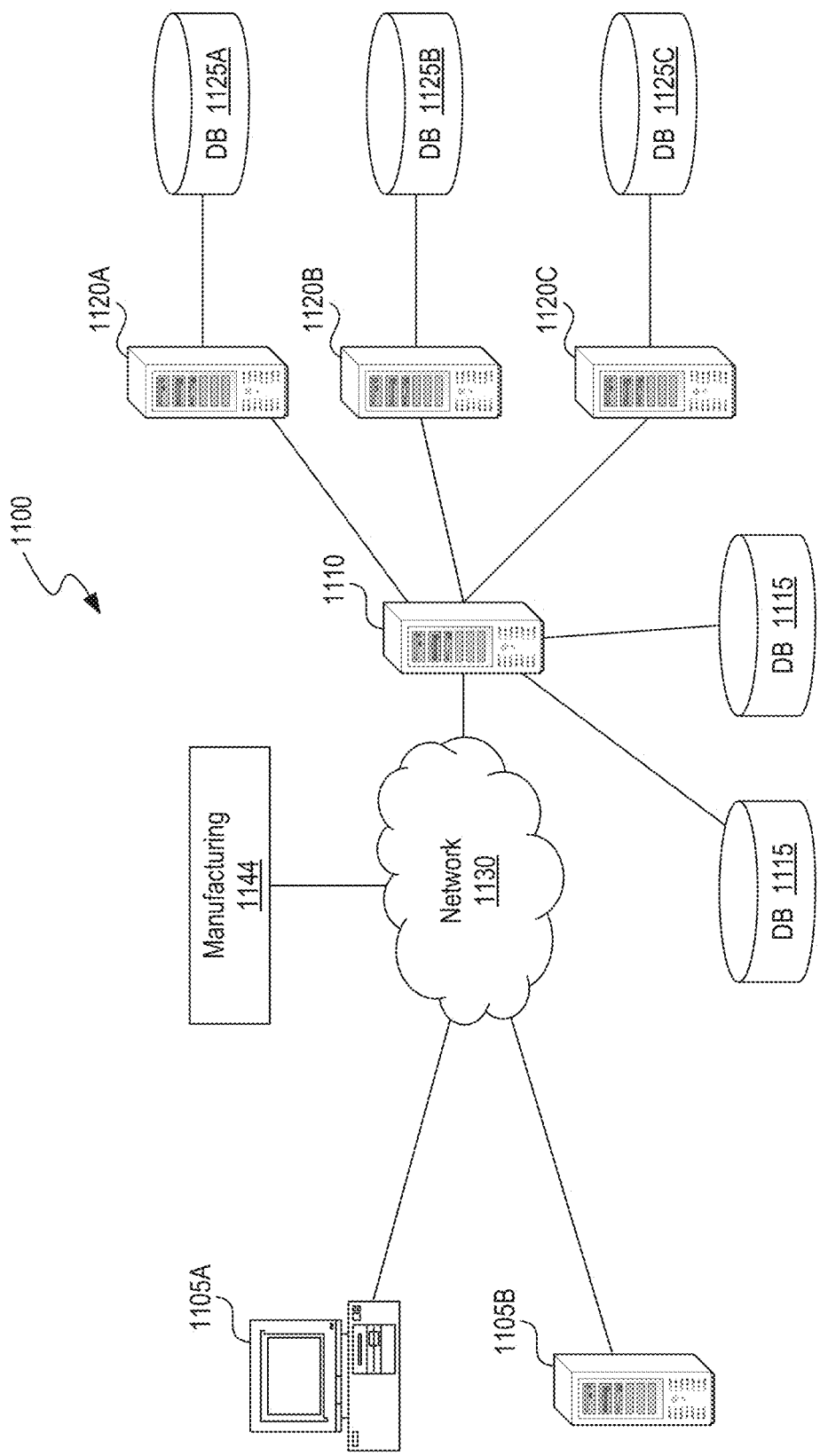
FIG. 11 is a block diagram illustrating an overview of an environment in which some implementations can operate.

FIG. 11 is a block diagram illustrating an overview of an environment or system 1100 ("system 1100") in which some implementations of the disclosed technology can operate. System 1100 can include one or more client computing devices 1105A-B. Client computing devices 1105A-B can operate in a networked environment using logical connections through network 1130 to one or more remote computers, such as a server computing device. The client computing devices 1105A-B can request, for example, personalized formulations, treatment protocols, compositions, composition analytics, patient records, etc.

In some implementations, server 1110 can receive client requests and coordinates fulfillment of those requests (e.g., personalized formulation orders, patient monitoring, etc.) through other servers, such as servers 1120A-C. Server computing devices 1110 and 1120A-C can comprise computing systems, such as device or system 1000 of FIG. 10. Though each server computing device 1110 and 1120A-C is displayed logically as a single server, server computing devices can each be a distributed computing environment encompassing multiple computing devices located at the same or at geographically disparate physical locations. In some implementations, each server 1120A-C corresponds to a group of servers.

Client computing devices 1105A-B and server computing device 1110 and 1120 can each act as a server or client to other server/client devices. Server 1110 can connect to one or more databases 1115. Servers 1120A-C can each connect to a corresponding database 1125A-C (collectively "databases 1125"). As discussed above, each server 1120 can correspond to a group of servers, and each of these servers can share a database or can have their own database. Databases 1115 and 1125 can store information, such as data discussed in connection with FIGS. 1-6 and other information disclosed herein. Though databases 1115 and 1125 are displayed logically as single units, databases 1115 and 1125 can each be a distributed computing environment encompassing multiple computing devices, can be located within their corresponding server, or can be located at the same or at geographically disparate physical locations. In some embodiments, the databases 1115 store patient data and can include, without limitation, sleep databases (e.g., database 112 of FIG. 1), biometric databases (e.g., biometric data from healthcare providers, wearable biometric devices), patient health databases, ERM databases, etc. The databases 1125 can include, without limitation, the composition databases 104, analgesic databases 106, bioavailability databases 108, and other databases disclosed herein. The server 1110 can acquire data from selected data bases to develop compositions.

Network 1130 can be a local area network (LAN), a wide area network (WAN) or other wired or wireless networks. Network 1130 may be the Internet or some other public or private network. Client computing devices 1105 can be connected to network 1130 through a network interface, such as by wired or wireless communication. While the connections between server 1110 and servers 1120 are shown as separate connections, these connections can be any kind of local, wide area, wired, or wireless network, including network 1130 or a separate public or private network.

The system 1000 can perform the steps discussed herein. For example, the server 1110 can function as the capsule module 114 (FIGS. 1 and 7) configured to formulate, for example, capsules for the subject by selecting specific excipients and other nonactive ingredients that are compatible with the active ingredients. The system 100 can retrieve data from one or more of the databases 1125A-C. The system 1000 can generate, store, train (including retraining), and/or modify one or more machine learning models, as discussed in connection with FIG. 12. In some embodiments, the system 1000 can generate formations for recreational and medicinal *Cannabis* formulations that comply with regulations, laws, and medical reimbursements. One or more of the databases 1125A-C can include, for example, regulations, laws, and medical reimbursements that are accessed based on the user's location, shipping information, etc. The system 100 can design cannabinoid compositions having improved, better controlled bioavailability. The number, type, and data structure of the databases 1115, 1125 can be selected based on the formulation design process.

The system 1100 can determine whether to manufacture multi-staged release compositions based on availability of suitable premade compositions. The server 1110 can be programmed to identify, order, and/or provide access to available compositions (e.g., preexisting or premade formulations in inventory, non-subject-specific formulations, etc.) to avoid or limit manufacturing times, subject-specific composition manufacturing costs, etc. In response to client requests, the system 1100 can send a notification from the server 1110 indicating the availability of the suitable composition. In some embodiments, the system 1100 (e.g., server 1110 or other servers) can query one or more of the databases 1125A-1125C storing inventory data, data of premade multi-staged release compositions (e.g., compositions in stock at local pharmacies, distribution centers, dispensaries, etc.), historical subject/user data, or the like. In some embodiments, the stored data can include, for example, inventory information (e.g., quantity of premade formulations), expiration information, composition of formulations, release profiles of compositions, manufacturing dates, manufacture information, ingredient lists, dosage forms, historical patient outcomes, and other information. The databases 1125A-1125C can store data disclosed herein, such as dosing models (e.g., subject-specific dosing models), subject/user data (e.g., electronic health records, physician notes, subject/user feedback, subject/user biometric data, etc.), sets of composition data, combinations thereof, or the like. Sets of composition data can include, without limitation, ingredient lists, percentages of ingredients, dosage forms, manufacturing instructions, or the like.

The system 1100 can determine whether compositions (e.g., multi-staged release compositions in inventory) are acceptable for a subject based on, for example, one or more multi-staged release profiles for that subject, maximum dosages for the subject, minimum dosages for the subject, input (e.g., physician input, healthcare provider input, etc.), or the like. In some implementations, the system 1100 can rank inventory based on a matching score. The system 1100 can compare a target multi-staged release profile of the subject to release profile of premade compositions to determine whether they match based on, for example, one or more matching criterion. The matching criterion can be inputted by, for example, a user, a physician, a healthcare provider, or the like. If the release profile of the premade composition is within an acceptable range of the planned release profile, the system 1100 can identify a match. The user can then be notified that a matching composition is in inventory, and the notification can include access information. The access information can include, without limitation, inventory location information, purchasing information, manufacturing information, links to vendor websites, dispensary information, prescription information, combinations thereof, or the like. In some embodiments, the system 1100 transmits a prescription via the network 1130 to a pharmacy computer 1105B. The user can then purchase the product at the pharmacy.

In response to the system 1100 determining that no suitable premade composition is available, the system 1100 can generate and send, via the network 1130, instructions for manufacturing to a manufacturer 1144. The instructions can include, without limitation, dosage form, number of compositions, percentages of compositions, manufacturing or processing steps, or other information suitable for use in manufacturing the multi-staged release composition. In some embodiments, the system 1100 uses one or more machine learning models to determine the manufacturing instructions, and the machine learning model can be trained using manufacturing data sets including manufacturing quality data. The system 1100 can identify acceptable compositions in inventory based on one or more criterion for the cannabinoid therapy. The criterion can include, without limitation, one or more release profiles, dosage ranges, manufacturer information, grower data, cannabinoid processing criterion, etc.

In some embodiments, the system 1100 can determine whether to manufacture a subject-specific multi-staged release composition based on an availability or inventory schedule of compositions. If acceptable premade compositions will be available within a desired period of time, the system 1100 can notify the subject of their availability. In some embodiments, the system 1100 can query inventory databases to identify acceptable compositions in inventory. The system 1100 can then send notifications identifying the available compositions for review by the subject. If a user (or physician, healthcare worker, etc.) approves the identified available composition, the system 1100 can order or provide purchasing instructions. If the user rejects the identified composition, the system 1100 can identify alternative compositions in inventory for user review and approval. If the user wants a subject-specific formulation, the user can select on-demand manufacturing of the user-specific formulation.

The system 1100 can use techniques disclosed herein to determine one or more cannabinoid therapies based on, for example, physician input, user input, user biometrics, prior patient outcomes, or the like. Prior patient outcomes can be selected based on matching cannabinoid therapies, subject/user conditions, etc. Cannabinoid therapies can include, without limitation, therapies for neurological diseases (e.g., Parkinson's disease, Huntington's disease, Alzheimer's, multiple sclerosis, etc.), anorexia, irritable bowel syndrome, pain management, psychological disorders, or the like. The system 1100 can generate a patient-specific dosing model complementing or matching criteria of the cannabinoid therapy for treating a therapeutic condition based pm the prior patient outcomes.

Figure 12:
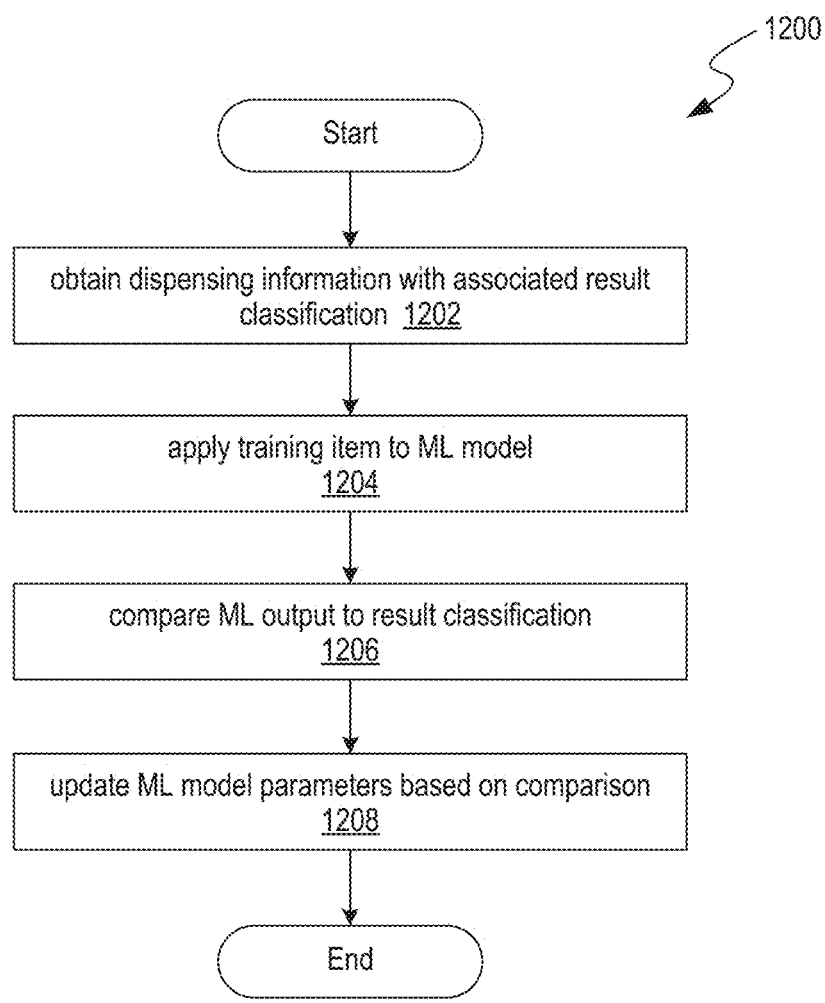
FIG. 12 illustrates a flowchart showing a method for training a machine learning model, according to an embodiment.

FIG. 12 illustrates a flowchart showing a method 1200, in accordance with some embodiments. Machine learning models, such as neural networks, can be trained to produce types of results. A neural network can be trained by obtaining, at block 1202, a quantity of "training items," where each training item includes input similar to input the model will receive when in use and a corresponding scored result. At block 1204, the input from each training item can be supplied to the model to produce a result. At block 1206, the result can be compared to the scored result. At block 1208, model parameters can then be updated, based on how similar the model result is to the scored result and/or whether the score is positive or negative. The method 1200 can be used to generate one or more trained machine learning models for outputting any of the following: composition, formulation, manufacturing process, dosing schemes, therapeutically effective amounts for a specific user, prediction of a future value of the health parameter within a period of time, prediction of therapeutic effect, predictions for avoiding adverse events, etc. The steps of the method 1200 can be selected based on the inputs and desired output and are discussed below.

At block 1202, model input can include, without limitation, stored data (e.g., data from databases 104, 106, 108, 110, 112, 114 of FIGS. 1-6), composition information, cannabinoid preferences, user-specific input (e.g., sensitivity level(s) to active agent sensitivity, analgesic sensitivity, bioenhancer sensitivity, etc.), caregiver input, and so forth. The training data input can be classified and/or paired with results to create training items. The classification can be selected based on the model characteristics and output. The results for training items can be, for example, user feedback to model outputs, healthcare provided suggestion feedback (e.g., whether the healthcare accepted model provided recommendations completely, or made certain changes, or disregarded), user rating or scoring of doses, biometric data analyzed to determine results, the existence of certain positive or negative user experiences, or the like. The product input can include, without limitation, characteristics disclosed herein, such as number of staged releases, length of each staged release, release profiles, target efficiency, user input, and so forth. The user input can include, without limitation, objective data, such as personal data collected by biometric or wearable devices. The user feedback may result in refined personal dosing schemes, recommended compositions/formulas, etc. The data discussed in connection with FIGS. 1-11 can be used as model input, model selection, etc. The input, subject scoring, and other information can be collected via, for example, a user device (e.g., user devices 1105A, 1105A of FIG. 11), input/output devices (e.g., input/output devices 1040 of FIG. 10), etc. In some embodiments, user feedback is aggregated. Aggregated user feedback may be used to develop and refine a heuristic algorithm to provide schemes, recommendations, etc., to new users, users using new substances, or the like.

At block 1204, input from each training item can be supplied to the model to produce a result or output. The output can be converted to arrays of integers that, when provided to the machine learning model, produce values that specify dosing schemes, device settings, etc. Any number of models can be generated to recommend dosing schemes, products for purchase, recommended flavoring products, etc.

At block 1206, results can be compared to the scored result or result classification. For example, result dosing schemes can be compared to actual dosing schemes used by users that produced the training item. The model can correlate composition information to predicted user experience or outcome. The composition information can release profiles, effect profiles, active agent characteristics, active agent interaction (e.g., interaction between multiple active agents), formulation characteristics, etc.

At block 1208, model parameters can be updated, based on how similar the model result is to the scored result and/or whether the score is positive or negative. The model parameters can then be adjusted so the model output is more like the prior formulation or dosing scheme and user experience if that prior user experience was a success or less like the prior dosing scheme, if the prior user experience was unsuccessful (e.g., undesired effect). The amount of adjustment to the model parameters can be a function of how different the model prediction was from the actual dosing scheme used and/or the level of success or failure of the product usage. Machine learning models can be trained to produce various results, determine dosing schemes (e.g., constant or variable dosing schemes), or the like. Models can be grouped or classified based on user characteristics, such as user sensitivity to active agents.

The method 1200 can generate dispensing schemes based on formulation form (e.g., pill, tablet, capsule, etc.), a user's profile, previous sensor data for that user, and/or information and/or sensor data from a plurality of other users. In some embodiments, a health state is quantified as a score or metric representing the user's overall health status and/or risk, which can be generated based on any suitable combination of sensor data and/or other data. In some embodiments, user-specific setting or recommendations may be based upon, for example, the health state, specific user's experience feedback, etc. The user experience feedback may query the user for a variety of parameters. A model can be trained using sets of user feedback, flavor profiles, dosage information, composition information, volumes, temperatures (e.g., active ingredient temperatures, flavor compound temperatures, etc.), type of administration (e.g., oral, transmucosal, etc.), and corresponding scores for usage.

The method 1200 can be used to train machine learning models for different dosage form. For example, one machine learning model can be used to formulate pills. Another machine learning model can be used to generate a formulation for capsules. Yet another machine learning model can be used to generate a formulation for topical or transdermal patches. In some embodiments, the systems disclosed herein can receive dosage form input. The system can then select a machine learning model based on the received dosage form. The system can retrieve data from a database associated with a form, user data, etc. In some embodiments, the retrieved data can be selected based on historical patient data for patients with similar or matching health profiles.

In some embodiments, multiple machine learning training procedures can be performed. Example procedures can include obtaining suitable training data set associated with a result, applying each training data set to the model, and updating model parameters based on comparison of model result to training set result. Each model can be designed for a different result. A neural network can be trained by obtaining a quantity of "training items or data set," where each training item or data set includes input similar to input the model will receive when in use and a corresponding scored result. The input from each training item/data set can be supplied to the model to produce a result. The result can be compared to the scored result. Model parameters can then be updated based on how similar the model result is to the scored result and/or whether the score is positive or negative. A training procedure can include clustering, predictive analysis, etc. as discussed above. The training procedure can be selected based on the amount, quality, and/or characteristics of the data.

In accordance with some embodiments, a computer implemented method for a multi-staged release composition for cannabinoid therapy includes storing data associated with a subject and generating a subject-specific dosing model for the subject based on the stored data. The method also includes determining a multi-stage release profile according to the generated subject-specific dosing model. The method includes selecting a dosage form for the multi-staged release composition based on the determined multi-stage release profile. The method includes determining two or more compositions staged for release at different times and/or with different release profiles based on the dosage form and the multi-stage release profile. The two or more compositions comprise one or more active agents comprising cannabinoids, one or more bioavailability enhancer, or both. The method also includes storing a set of data for the multi-staged release composition in a database. The set of data includes the two or more compositions and the dosage form.

In some embodiments, the method includes generating the subject-specific dosing model by using a machine learning technique. Generating the subject-specific dosing model includes obtaining classified training items. The classified training items include training data paired with a set of outcomes. The set of outcomes includes multiple levels of therapeutic effects achieved by treatment of training subjects with multi-staged release compositions. The therapeutic effects can be associated with a therapeutic condition selected from at least one of alleviating pain, providing energizing effects, increasing appetite, assisting with sleep, stimulating introspection, or aiding meditative practice. Generating the subject-specific dosing model includes applying the classified training items to a machine learning algorithm to generate the subject-specific dosing model.

In some embodiments, the method further includes comparing the generated subject-specific dosing model to the training data paired with the set of classifications and updating the subject-specific dosing model based on the comparison.

In some embodiments, the training data includes subject data of training subjects. The subject data of training subjects includes one or more of a therapeutic condition associated with a respective training subject and one or more of sleep data associated with the respective training subject, biometric data associated with the respective training subject, input from the respective training subject, input from a physician associated with the respective training subject, and retrieved data from an electronic medical record for the respective training subject.

In some embodiments, the training data includes one or more of a number of stages, a length of stages, dosage amounts, and/or data associated with the treatment of the training subjects with the multi-staged release compositions.

In some embodiments, the method further includes determining whether an acceptable premade multi-staged release composition is available for the subject based on the multi-stage release profile. The premade multi-staged release composition includes the determined two or more compositions. In response to determining the premade multi-staged release composition is available, the method includes providing access information for the premade multi-staged release composition to the subject. In response to determining that the premade multi-staged release composition is not available, the method includes sending instructions for manufacturing the multi-staged release composition for the subject.

In some embodiments, the method further comprises comparing the multi-stage release profile to a release profile of the premade multi-staged release composition to determine whether the premade multi-staged release composition is acceptable for the subject.

In some embodiments, the method further comprises matching the premade multi-staged release composition to the subject based on at least one cannabinoid therapy criterion.

In some embodiments, the method further includes querying at least one inventory database of multi-staged release compositions to identify an acceptable multi-staged release composition in inventory. The method also includes sending a notification for the subject of the identified acceptable multi-staged release composition for the subject.

In some embodiments, the method further comprises determining a cannabinoid therapy model based on prior patient cannabinoid therapy outcomes for prior patients that match the subject. The generation of the subject-specific dosing model is based on the cannabinoid therapy and a therapeutic amount at least one of the two or more compositions.

In some embodiments, the method further includes determining whether to manufacture a subject-specific multi-staged release composition based on an availability schedule of acceptable non-subject-specific multi-staged release composition for the subject.

In some embodiments, determining the multi-stage release profile for the multi-staged release composition includes matching the multi-stage release profile to the subject-specific dosing model.

In some embodiments, the dosage form includes a pill, a tablet, a capsule, a transdermal patch, a transmucosal patch, a lozenge, intranasal formulation, or a suppository.

In some embodiments, the multi-stage release profile includes: a number of stages, lengths of respective stages, amount of dosage for the respective stages, and tapering for the respective stages.

In some embodiments, receiving the subject data of the subject includes receiving biometric data obtained by a wearable electronic device worn by a subject.

In some embodiments, receiving the subject data of the subject includes receiving biometric data obtained from the subject using a wearable electronic device.

In accordance with some embodiments, a system for manufacturing a multi-staged release composition includes a composition manufacturing system configured to manufacture unit dosage forms and a dosage designing server system. The dosage designing server system is in communication with a user device and the composition manufacturing system. The dosage designing server system is programmed to receive, from the user device, a user request for an indication of two or more compositions staged for release for treatment of a therapeutic condition of a subject. In response to the user request, receive subject data of the subject. The subject data includes data retrieved from one or more databases of the server system, and input received from the respective user device. The server system is programmed to analyze the subject data to generate a dosing model and determine a multi-stage release profile for the multi-staged release composition according to the dosing model. The server system is programmed to select a dosage form for the multi-staged release composition based on the multi-stage release profile. The server system is also programmed to determine the two or more compositions staged for release at different times or with different release profiles based on the dosage form and the multi-stage release profile. One or more staged compositions comprise one or more active agents comprising cannabinoids, one or more bioavailability enhancer, or both. The server system is programed to send instructions to the composition manufacturing system to manufacture unit doses of the multi-staged release composition in accordance with the indication of the two or more compositions staged for release.

In some embodiments, the user device is an electronic device associated with the subject.

In some embodiments, the user device is an electronic device associated with a physician treating the subject.

In some embodiments, causing, by the dosage designing server system, the composition manufacturing system to manufacture the multi-staged release composition in accordance with the with the indication of the two or more compositions staged for release.

In some embodiments, dosage designing server system is configured to cause the composition manufacturing system to manufacture the multi-staged release composition in accordance with the with the indication of the two or more compositions staged for release.

In an illustrative embodiment, any of the operations, processes, etc., described herein can be implemented as computer-readable instructions stored on a computer-readable medium. The computer-readable instructions can be executed by a processor of a mobile unit, a network element, and/or any other computing device.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

From the foregoing, it will be appreciated that specific embodiments of the invention have been described herein for purposes of illustration, but that various modifications may be made without deviating from the scope of the invention. Accordingly, the invention is not limited except as by the appended claims.

Reducing Opioids from Pain Regimens

Opioid addiction is a debilitating disease characterized by physical and psychological reliance on opioids, a class of molecules found in certain prescription pain medications and illegal drugs such as heroin. The United States is in the midst of an opioid abuse epidemic. Opioid addiction commonly starts in patients who are prescribed painkillers but fail to detox from opioids after an extended period of time due to the persistence of pain and/or increasing dependence on the prescription drugs containing opioids.

Over time, patients may become tolerant to opioids, which can lead to an escalation in opioid dosing. Escalated dosing can exacerbate withdrawal effects when opioids are removed and increase the risk of addiction. Long-term opioid use is associated with poor health outcomes including overdose, organ system failures, and death. Additionally, patients who are opioid-dependent preoperatively have been shown to have worse clinical outcomes following surgical treatment.

There is a need to provide a method for patients with acute and chronic pain to avoid unnecessarily high dosages of opioids or safely taper off, and eventually eliminate, the use of opioids to improve health outcomes. Many patients are turning to *Cannabis* and/or extracts of *Cannabis*, which contain pain-relieving cannabinoids, such as cannabidiol (CBD) and tetrahydrocannabinol (THC), as well as other non-cannabinoid compounds to treat pain. Areas of the United States with legal access to medical and adult-use *Cannabis* products show a decrease in rates of opioid use. While physicians are largely prevented, for a host of reasons, from actively prescribing cannabinoids as a treatment for pain, this could change in the future, as medical science and regulatory regimes increasingly accept the validity of *Cannabis* and *Cannabis*-derived compounds for certain patients. In addition, the current practice of medicine restricts the use of therapeutic pain treatments to after a pain-generating event even when planned, e.g. surgery. By focusing on pain pre-treatment there is much to be gained in terms of decreasing the magnitude of the resulting pain and, as a result, the amount of pain-killers, including opioids, that must be used post pain-inducing event. This paradigm focuses on modulating, and often times down-regulating, the inflammasome prior to an event that will trigger inflammatory cascades, such as surgery or extreme competition. Humans historically appear to have had lower baseline levels of activity in the human inflammasome compared to modern day humans. This could be a result of changes in the diet, environmental exposures, or activity levels that have placed the inflammasome of the average modern day human in a suboptimally elevated baseline state that leads to inflammatory and pain dysfunction post physiological or psychological insult. There is suggestion that an elevated baseline inflammatory state leads to worse outcomes post stress- and/or pain-inducing event, which can in turn require increased levels of anti-inflammatory and/or pain treatments. Dosing schedules that are longer in duration or greater in magnitude can increase the probability of addiction (e.g. opioids) or for bodily injury, such as unnecessary taxation of the liver (e.g. acetaminophen).

A software kit for reducing dependence on opioids may be useful for a wide variety of practitioners, patients, and opioid-dependents who wish to transition from opioid-based pain management to cannabinoid pain management, which may involve significantly less dependency, addiction potential, and overall health hazards. Such software kits could be provided in pharmaceutical settings where dosing can be tightly controlled and monitored and provide patients and those dependent on opioids with relief from symptoms associated with opioid withdrawal.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The devices, systems, and methods of the present disclosure provide for an improved, automatically adjustable way of reducing opioids in a patient's pain-modulating regimen. The present disclosure reduces the risk of opioid addiction leading to long-term use of opioids. Long-term use of opioids may lead to poor health, organ system failures, or even death from overdose. The method is based on generating a dosage scheme for a patient based on parameters associated with the patient's health condition, including a designed pre-pain treatment regimen when pain is anticipated before events such as surgery or other physiologically taxing activities. The dosage scheme includes dosage schemes for an opioid compound and a cannabinoid compound so that the dosages of opioids decrease over a period of time and where the dosing of the cannabinoid compound begins prior to pain, The dosage scheme can then be automatically adjusted based on the pain level of the patient. The patient's pain level is assessed based on feedback received (e.g., on a standardized pain scale) from the patient or based on physiological pain level indicators based on biometric data. Examples of commonly used opioid drugs include but are not limited to oxycodone, codeine, hydrocodone, hydromorphone, oxymorphone, methadone, morphine, fentanyl and tapentadol.

In accordance with some embodiments, a method for reducing opioids in a pain-modulating regimen of a patient is performed by a computer system. The method includes generating, by a computer system, a dosage scheme for the patient based on parameters associated with the health condition of the patient. The dosage scheme includes a first dosage scheme for an opioid compound and a first dosage scheme for a cannabinoid compound. The opioid and the cannabinoid may be administered to the patient concurrently over a period of time or the cannabinoid may be administered days before the opioid administration begins. The first dosage scheme for the opioid compound includes a first plurality of dosages with a decreasing amount of an active ingredient in the opioid compound over the period of time. The method also includes receiving pain level indicators associated with the patient. The pain level indicators include a first pain level indicator based on an input from the patient and a second pain level indicator based on biometric data obtained by a wearable device. The wearable device is configured to be worn by the patient. The method includes determining, by the computer system, whether to adjust the dosage scheme based on the pain level indicators. In response to determining to adjust the dosage scheme, the method includes generating an adjusted dosage scheme based on the pain level indicators. The adjusted dosage scheme includes a second dosage scheme for the opioid compound. The adjusted dosage scheme is different from the first dosage scheme for the opioid compound to be administered to the patient.

In accordance with some embodiments, a method for administering drugs to a patient includes generating, by a computer system, an initial dosage scheme for the patient based on parameters associated with a health condition of the patient. The initial dosage scheme includes a first dosage scheme for a first drug and a first dosage scheme for a second drug to be administered to the patient concurrently over a period of time. The first dosage scheme for the first drug includes a first plurality of dosages with a decreasing amount of an active ingredient in the first drug over the period of time. The method includes receiving, by the computer system, one or more health condition indicators associated with the patient. The one or more health condition indicators include an indicator based on an input from the patient. The method also includes generating, by the computer system, a subsequent dosage scheme based on the one or more health condition indicators.

In accordance with some embodiments, a method for opioid management in a pain-modulating regimen for a patient includes receiving, by a computing system, patient data of a patient. The method includes generating, by at least one trained cannabinoid dosing machine learning model, a pain relief regimen based on the received patient data. The pain relief regimen includes an opioid tapering dosage scheme and a cannabinoid dosage scheme. The cannabinoid is designed to compensate for opioid tapering of the opioid tapering dosage scheme such that the pain relief regimen effectively alleviates the pain of the patient. In some embodiments, the present disclosure includes a semi-autonomous system for mitigating the risks of opioids with cannabinoids. The system may taper the quantity of opioids to minimize the risk of opioid dependence. For example, the system provides for dosage schemes of reducing an administered dosage of opioids while concurrently administering cannabinoids to manage a patient's pain. The risk associated with opioids may be physical dependence or addiction. In some embodiments, the risk associated with opioids is respiratory arrest or death, or liability on the part of the prescribing physician for over-prescribing or mis-prescribing. In some embodiments, cannabinoids may be included in the dosage scheme irrespective of non-medical prescribing limitations.

In some embodiments, the system interfaces with opioid-prescribing monitoring databases to maintain compliance.

In some embodiments, biometric data, as well as input provided by a patient (e.g., a user), are analyzed to adjust dosage regimens in real time. The system also may optimize the dosage scheme toward the minimal quantity of necessary opioids over time.

In some embodiments, the system provides indications for dosages including one or more compounds possessing phytocannabinoid-based chemical structures or exhibiting pharmacological activity on the endocannabinoid system. The cannabinoid compound may be selected from a group consisting of tetrahydrocannabinolic acid (THCA), tetrahydrocannabinol (THC), cannabidiolic acid (CBDA), cannabidiol (CBD), cannabigerolic acid (CBGA), cannabigerol (CBG), cannabichromenic acid (CBCA), cannabichromene (CBC), cannabinol (CBN), cannabielsoin (CBE), cannabicyclol (CBL), and cannabicitran (CBT), in addition to all respective isomers and human metabolites of in-group molecules. "A *Cannabis* compound" shall mean any constituent extracted or derived from a plant belonging to the genus *Cannabis*, including, but not limited to cannabinoid, terpenoid and flavonoid compounds as well as synthetic, semi-synthetic or highly purified versions of any such constituent.

In some embodiments, the system is for mitigating the risks of anesthetics and sedatives with cannabinoids. The system may successfully taper the quantity of sedatives or anesthetics to minimize the risk of the patient regaining consciousness unexpectedly or minimize the effective quantity of sedatives or anesthetics required due to pre-treatment with cannabinoids. The risk associated with sedatives or anesthetics may be respiratory arrest or death. In some embodiments, the risk associated with anesthetics is physical dependence developed by the anesthesiologist due to environmental exposure to unnecessary anesthetics.

In some embodiments, the cannabinoids are administered via the same or different route of administration as sedatives or anesthetics.

In some embodiments, the system is for decreasing or optimizing the total consumption of prescription drugs.

Figure 13:
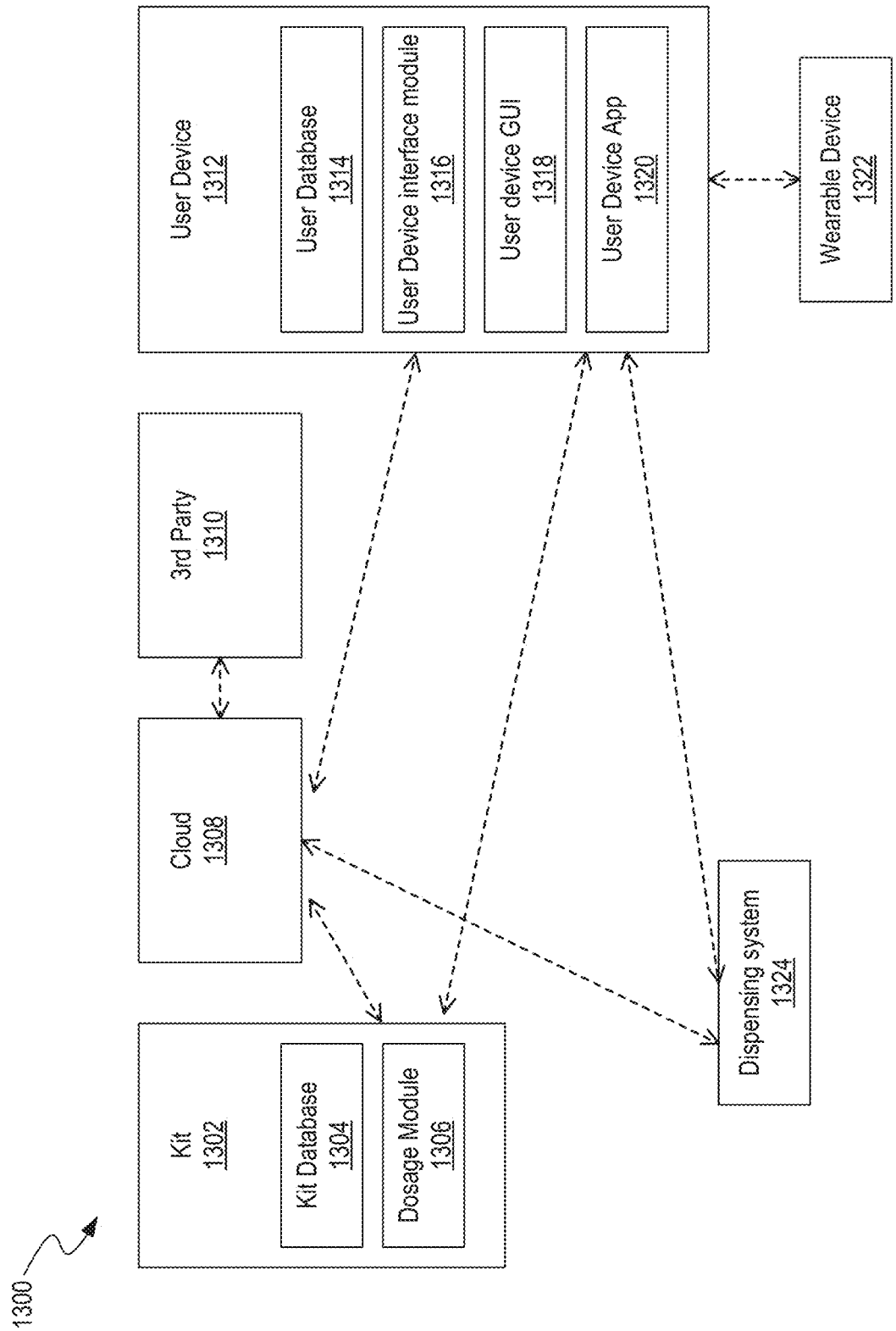
FIG. 13 illustrates a system for eliminating opioids from a patient's pain regimen by gradually replacing the opioid doses with cannabinoids and other pain treatments, in accordance with some embodiments.

A Software Kit and Processes for Reducing Opioids from Patient's Pain-Modulating Regimen FIG. 13 shows a system 1300 including a software kit 1302 (e.g., a software application or a program) for eliminating opioids from a patient's pain regimen by gradually replacing the opioid doses with cannabinoids and other less harmful pain treatments. The other pain treatments may include acetaminophen, non-steroidal anti-inflammatory drugs (e.g., aspirin, ibuprofen, naproxen), and other drugs; plant-derived extracts and complex mixtures (e.g., kratom, turmeric, white willow, and Boswellia); and mind-body techniques (e.g., acupuncture and meditation). The software kit 1302 offers a solution for pain management and opioid cessation in patients who have been prescribed painkillers but fail to detox from opioids after an extended time due to the persistence of pain and/or increasing dependence on the prescription drugs. The software kit 1302 may help mitigate the risk of a patient becoming tolerant to opioids, which often leads to an escalation in dosing of opioids-a strong risk factor for addiction. The system 1300 further includes a user device 1312 that is in communication with the software kit 1302 and a cloud 1308 (e.g., a cloud server) for facilitating the communications and operations of the system 1300. In some embodiments, the system 1300 further includes a third-party device 1310.

The software kit 1302 may offer a solution for patients with acute and chronic pain by eliminating the use of opioids and improving health outcomes through the intelligent use of *Cannabis*, cannabinoids (e.g., THC, CBD, and chemical/physiological analogues), and/or extracts of *Cannabis* to treat pain. Thus, the software kit 1302 may determine a dosing scheme based on pain severity and expected length, i.e., addition of the THC, CBD, and/or analogues in a specific ratio for a specific pain level such that higher pain levels may be associated with higher doses of the dosing scheme or higher ratios of specific components within the scheme. Importantly, the software kit 1302 may offer pre-treatment regimens of cannabinoids to mitigate the severity of pain and inflammation before it occurs or before it increases. This approach represents a novel approach to mitigating inflammation and pain by pre-treating the inflammasome of the patient before inflammation, physiological damage and pain-generating stimuli are scheduled to occur.

The software kit 1302 may include a software kit database 1304 having indications of the pharmaceutical doses of the drugs measured out in relevant periods such as hours in a day, days, weeks, months, etc. Indications of pharmaceutical doses refer to information or data associated that can be provided to the patient (e.g., by displaying the indication on a display of a computer device). The indications of the pharmaceutical doses can include volumes, weights, concentrations, dosing frequency, pharmaceutical identifiers, etc., associated with the pharmaceutical compounds. The software kit 1302 may have a pharmaceutical composition including a cannabinoid and a nonsteroidal anti-inflammatory drug (NSAID).

The pharmaceutical doses may be in any one or a combination of forms, such as pills, capsules, tablets, transdermal patches, injections, tinctures, smokable herbs, vaporizers, or any other form in which opioids or cannabinoids may be administered. The nonsteroidal anti-inflammatory drug (NSAID) may be, for example, aspirin, ibuprofen, naproxen, etc. The pharmaceutical composition has a cannabinoid composition, which includes a *Cannabis* compound, a pain management composition, which may be pharmaceutical and/or botanical, and an opioid cessation composition (e.g., methadone). In one embodiment, the software kit 1302 may offer opioid cessation including compositions of opioids and cannabinoids in various proportions. The proportion of opioids may gradually decrease throughout the software kit 1302 compositions as the proportions of cannabinoids gradually increase. It can be noted that the cannabinoids may be selected for pain management therapy. The final composition of the software kit 1302 may contain zero or a negligible quantities of opioids. In addition, the composition of cannabinoids can also follow a tapering regimen after the conclusion of opioids.

In some embodiments, the software kit 1302 may offer matching of cannabinoids and *Cannabis* compounds with nutritional supplements for synergistic effects. The software kit 1302 may facilitate assessing the intended effect of a nutritional supplement and matching it with the cannabinoid extract with the most synergistic properties.

In some embodiments, the software kit 1302 may be coupled to the user device 1312 to facilitate user feedback to the software kit 1302, via a user device app 1320 on the user device 1312. The user feedback may allow the regimen to be adjusted based on a change in a patient's pain level. For example, improvements in pain can produce a new regimen with reduced dosing in real time such as advising the patient to halve the next suggested dose or skip a dose entirely. The patient feedback can include pain scores on a standardized pain score scale. Such standardized pain score scale can include visual analog scale (VAS), numerical rating scale (NRS), defense and veterans pain rating scale (DVPRS), non-verbal pain scale (NVPS), pain assessment in advanced dementia scale (PAINAD), behavioral pain scale (BPS), critical-care pain observation tool (CPOT), or any other standardized pain scale score.

The user device 1312 may also help in tracking the usage of the software kit 1302 over time as well as continually monitoring the patient's pain. Tracking of the usage of the software kit 1302 and the patient's pain may be achieved by making a graph in which the Y-axis displays dosing measures of opioid (e.g., oxycodone) pain management and the X-axis displays dosing measures of the cannabinoids. It should be noted that the chart may have a negative or downward (left-to-right) slope since the opioid doses decrease as the cannabinoid doses increase, creating an inverse relationship, and each point on the chart could represent one week, day, or hour in the pain regimen.

In one embodiment, the software kit 1302 may include specific instructions for the dosing regimen and for the need to wean patients off opioids (based on risks and dangers of dependency) as well as information about the effectiveness and safety of the cannabinoid formulation. In one case, a plurality of software kits 1302 might be available and the physician may prescribe a particular software kit 1302 to the patient based on the pain level, tolerance, doses, etc., of the patient. In another case, the software kit 1302 may be customized for each patient by the physician based on the pain level, tolerance, doses, etc., of the patient. In one embodiments, the software kit 1302 may be chosen based on the duration of post-operation (e.g., surgical) care, with dosing for specific pain types and magnitudes. In some embodiments, the software kit 1302 may be chosen based on a need to reduce opioids pre-operatively. It can be noted that once the pain is at a manageable level, the patient may be allowed to reorder cannabinoid therapy without a prescription, but would perhaps need to go to the doctor and have pain assessed for additional opioid doses.

For example, a topical CBD can prevent pain and modulate inflammation in some pseudo-surgical applications (for example, applying topical CBD prior to a tattooing operation). Thus, topically applied presurgical and post-surgical CBD could be an effective pain and inflammation management tool. In one embodiment, one or more software kits 1302 may be available and choices for the software kit 1302 may be based on the type of injury/surgery/operation. For example, a patient experiencing liver failure may opt to receive a liver transplant and the recovery from such a transplant may take 2 to 4 months. The patient may have an initial pain intensity of 8 that may gradually decrease with time and may require 100 mg of an opioid, 100 mg of a cannabinoid, and a total of 1800 mg of therapeutic agents of all types on the day of surgery. The amount of opioid(s) and cannabinoid(s) may change based on the change in pain intensity. Hence, as the pain decreases in magnitude the quantity of opioid(s) administered may decrease while the quantity of cannabinoid(s) may increase.

In one embodiment, the software kit 1302 may be associated with a software app, which tells the patient which elements of the software kit 1302 to use, based on the patient pain check-in or a questionnaire. The software kit database 1304 of the software kit 1302 may include pharmaceutical doses of the drugs measured out in relevant periods such as hours of the day, days, weeks, months, etc. The software kit database 1304 may also include a combination of opioid(s), cannabinoid(s), and other painkillers in various proportions based on user parameters.

The pharmaceutical doses may be in any one or a combination of forms, such as pills, capsules, tablets, transdermal patches, injections, tinctures, smokable herbs, vaporizers, or any other form in which opioids or cannabinoids may be administered. In one embodiment, the software kit database 1304 may also include dosages of drugs before surgery to wean patients onto cannabinoid treatment after surgery since administering cannabinoids before pain actually occurs can decrease both the perception and the physiological manifestation of pain. Reduction of opioids preoperatively may lead to a better control of a patient's pain during and after surgery thereby causing an improved outcome for the patient. For example, the software kit database 1304 includes, for two days before surgery, a dosage of 25 mg of 11-OH delta-9 tetrahydrocannabinol (11-OH-d9-THC) for the patient experiencing the liver failure, twice a day. The software kit database 1304 may include indications of pharmaceutical doses of drugs measured out in relevant hours of day and days for short-term pain. For example, the software kit database 1304 indicates that, for the day of surgery, a dosage of 25 mg of hydrocodone and 25 mg of CBD is to be administered to the patient 4 times a day, and 500 mg of acetaminophen and 300 mg of ibuprofen are to be administered twice a day. The software kit database 1304 may include indications of pharmaceutical doses of drugs measured out in week- and month-long periods for pain of extended duration. For example, the software kit database 1304 includes, for the first week post-surgery, a regimen of 25 mg of hydrocodone, 25 mg of CBD, 500 mg of acetaminophen, and 300 mg of ibuprofen twice a day.

In some embodiments, the software kit 1302 includes a dosage module 1306 that may receive data from the patient via a user device interface module 1316. In some embodiments, the system 1300 includes interfaces between dosage module 1306 and user device interface module 1316 and prescription monitoring databases to ensure that both the prescriber and the patient maintain compliance with all local, state, and federal statutes and codes. Such background interfacing between the semi-autonomous prescribing system and the prescription monitoring database could serve as a checksum to protect the health of the patient and the potential liability of the prescriber. In one embodiment, the data may include a pain level received from the patient through the user device interface module 1316. For example, the dosage module 1306 receives the pain level of 8 (out of 10) associated with the patient with the liver failure on the day of his surgery, from the user device interface module 1316. In some embodiments, the dosage module 1306 may retrieve the user parameters from a user database 1314. For example, the dosage module 1306 extracts the user parameters, i.e., gender, age, weight, height, medical conditions, personality, and disposition associated with the patient from the user database 1314. The medical conditions may include medical conditions that are associated with pain or that can cause pain. The medical conditions may further include any medical conditions that may affect the effectiveness of any pain relief medications. The medical conditions may also include conditions that can be affected by any pain relief medications. The disposition may refer to a disposition to addiction including a history of addictive behavior, genetic disposition to addiction or drug or alcohol abuse, et cetera.

In some embodiments, the dosage module 1306 matches the pain level and the user parameters with a dose level. In some embodiments, the dose level may be retrieved from the software kit database 1304. For example, the dosage module 1306 matches the pain level of 8 (out of 10) associated with the patient and the user parameters associated with the patient with the dose level on the day of the patient's surgery. For example, the patient's pain level and parameters are matched with a dose level including 25 mg of hydrocodone and 25 mg of CBD 4 times a day, and 500 mg of acetaminophen and 300 mg of ibuprofen twice a day, i.e., $((25\times4)+(25\times4)+(500\times2)+(300\times2))$ mg=1800 mg of total medications or medicaments per day. The dosage module 1306 may further determine the dosage amount for the patient. For example, the dosage module 1306 determines that the patient requires 25 mg of hydrocodone and 25 mg of CBD 4 times a day, and 500 mg of acetaminophen and 300 mg of ibuprofen twice a day, i.e., ((25×4)+(25×4)+(500×2)+(300×2)) mg=1800 mg of total painkiller and inflammation-modulating compounds on the day of his surgery. In some embodiments, the dosage amount is determined based on the software kit database 1304. In some embodiments, the dosage module 1306 may determine which prescription is required for the patient. The prescription may be dependent on the day associated with the surgery (such as the day of surgery or 2 days after surgery).

In one embodiment, the dosage module 1306 may determine the dosage amounts for the patient for a week with a decreasing quantity of opioids and an increasing quantity of cannabinoid(s). For example, 1st day—1800 mg, 2nd day—1800 mg, 3rd day—1800 mg, 4th day—1800 mg, 5th day—1810 mg, 6th day—1820 mg, and 7th day—1810 mg. In another embodiment, the dosage module 1306 may determine the dosage amounts for the patient for one or more weeks with a decreasing quantity of opioids and an increasing quantity of cannabinoid(s). For example, 1st week—1800 mg, 2nd week—1875 mg, 3rd week—2850 mg, 4th week—3025 mg, 5th week—3220 mg, 6th week—4210 mg, 7th week—4405 mg, and >7th week—4400 mg. The dosage module 1306 may extract the dosage indications from the software kit database 1304. For example, the dosage module 1306 extracts from the software kit database 1304 that the patient requires 1800 mg of painkillers on the day of his surgery. Based on the extracted dosages from the software kit database 1304, the dosage module 1306 may send the dosage notification to the user device interface module 1316. For example, the dosage module 1306 sends a notification to the user device interface module 1316 stating that the patient requires 1800 mg of painkillers on the day of his surgery, i.e., 25 mg of hydrocodone and 25 mg of CBD 4 times a day, and 500 mg of acetaminophen and 300 mg of ibuprofen twice a day. In one embodiment, the dosage module 1306 may also send risks of dependence and alternative therapies to the user device interface module 1316. In some embodiments, the dosage module 1306 may utilize the concept of artificial intelligence (AI) to determine the dosages as well as risks of dependence and alternative therapies. The processes for training and applying artificial intelligence to determine the dosages, as well as risks, are discussed in detail with respect to FIG. 20.

The system 1300 may also include the cloud 1308. The cloud 1308 or communication network may be a wired and/or a wireless network. The communication network, if wireless, may be implemented using communication techniques such as Visible Light Communication (VLC), Worldwide Interoperability for Microwave Access (WiMAX), Long Term Evolution (LTE), Wireless Local Area Network (WLAN), infrared (IR) communication, Public Switched Telephone Network (PSTN), radio waves, and other communication techniques known in the art. The communication network may allow ubiquitous access to shared pools of configurable system resources and higher-level services that can be rapidly provisioned with minimal management effort, often over the internet, and relies on sharing of resources to achieve coherence and economies of scale, like a public utility, while third-party clouds enable organizations to focus on their core businesses instead of expending resources on computer infrastructure and maintenance.

In some embodiments, the system 1300 may include a third-party device 1310 (e.g., a computer device such as a laptop, smartphone, tablet, computer, smart speaker, or input/output (I/O) device) such as, but not limited to, a device associated with a doctor, caretaker, physician, or pharmacy, etc. The third-party device 1310 may add new data or update existing data in the software kit database 1304 based on the user parameters such as pain intensity, gender, age, weight, height, medical conditions, personality, and disposition. The third-party device 1310 may add indications of pharmaceutical doses of drugs measured out in relevant hours of day and days for short-term pain. The third-party device 1310 may be used to prescribe different types of cannabinoid treatment for individual patients. For example, some patients may end up with some level of chronic pain and the third-party device 1310 may be used to prescribe dosages for treatment of the chronic pain. As another example, the third-party device 1310 adds, for the day of surgery, a dosage of 25 mg of hydrocodone and 25 mg of CBD for the patient 4 times a day, and 500 mg of acetaminophen and 300 mg of ibuprofen twice a day. The third-party device 1310 may add pharmaceutical doses of drugs measured out in week and month for long-term pain. For example, the third-party device 1310 adds, for the first week post-surgery, a dosage of 25 mg of hydrocodone and 25 mg of CBD for the patient four times a day, and 500 mg of acetaminophen and 300 mg of ibuprofen twice a day.

In some embodiments, the system 1300 may include one or more user devices 1312 (e.g., a computer device such as a laptop, smartphone, tablet, computer, smart speaker, or I/O device). In some embodiments, the user device 1312 corresponds to, includes, or is in communication with a wearable device 1322. In some embodiments, the wearable device 1322 is a smartwatch, a wristband, a fitness tracker, or a wearable medical device. The wearable device 1322 includes one or more sensors configured to detect one or more health condition indicators associated with the patient. The health condition indicators include one or more of a pain level, a heart rate, a temperature, a blood pressure, a respiration rate, an oxygenation level, a motor activity level, a pupil constriction/dilation level, and sleep phase information. The wearable device 1322 may utilize the user device 1312 as additional memory or computing power or connection to the internet.

In some embodiments, the system 1300 may include, or be in communication with, one or more dispensing containers or systems 1324 (e.g., a medical dispensing system or a dosage system). The dispensing system 1324 can be in wireless communication with the user device 1312 and/or the cloud 1308. The dispensing system 1324 can include, for example, a pill box, a smart dispensing container, or the like. A pill box or a pill organizer or medication organizer ("pill box") can include small compartments labeled with days of the week and sometimes times of the day. The pill box can be used to organize and store medications to ensure that individuals take the right pills at the right times. The pill box can be a smart pill box so that the compartments can be locked and unlocked by electronic mechanisms.

The dispensing system 1324 can be configured to receive instructions from the user device 1312 and/or from the kit 1302 via the cloud 1308 to allow a user to access medicines stored at the dispensing system in accordance with the instructions. For example, the dispensing system 1324 can allow a user access (e.g., by unlocking a door of the compartment) to medicine stored at a particular compartment at a particular time of the day in accordance with the instructions. The compartment can remain locked outside a particular time so that the user cannot open the compartment. For example, the pill box can be a smart dispensing container with a controller that stores, for example, authentication programs, protocols, schedules, user or healthcare settings, or the like. The authentication protocols can be used to authenticate a user via, for example, biometric information (e.g., via a fingerprint scanner, smartwatch, smartphone, image capture device, etc.), an input device (e.g., keypad), etc. Biometric information can include, without limitation, one or more of a fingerprint, voice, facial features, retina data, or the like. The authentication programs can compare and/or match the acquired biometric information with reference biometric information to authenticate the patient. The reference biometric information can be provided by a healthcare provider, the patient, or an authenticated or trusted source. The schedules can be physician-manage schedules, including dosing schedules, medication availability schedules, notification schedules, or the like. The dispensing 1324 can also include various scanners (e.g., retina scanners), microphones, cameras, and/or sensors to, for example, verify (e.g., based on barcoding or radio frequency identification (RFID) tag) the accuracy of the stored medicine, authenticate the identity of a user (e.g., by a password, or a fingerprint or facial recognition), and/or track the medicines that have been removed from the system by the user. The sensors can include fingerprint sensors for obtaining biometric information.

In some embodiments, feedback on efficacy (patient and/or caretaker feedback plus biometric data) can be collected from user device 1312 via input by humans or via interfacing with external biometric sensors (e.g., the heart rate, temperature, respiration rate, oxygenation levels, motor activity levels, pupil constriction/dilation, sleep phases, etc.). A key element of such a software kit 1302 enabled with user and biometric data input is the ability to adjust the treatment algorithm and/or dosing schedule automatically and in real time. In some embodiments, the software kit 1302 may utilize a user database 1314 that may contain the data received by the user device interface module 1316. The user database 1314 may contain the basic user data such as gender, age, weight, height, medical conditions, personality, and disposition. In addition, the user database 1314 can contain active-pharmaceutical ingredient-specific data that may also be relevant in tailoring dosage regimens of pharmacologically active compositions. For example, tailoring may include collecting and querying information about the patient's opioid history prior to prescription, patient-reported outcomes, side effects previously reported, and efficacy of prior prescription regimens. The patient-reported outcomes may include pain scores on the standardized pain score scale such as visual analog scale (VAS), numerical rating scale (NRS), defense and veterans pain rating scale (DVPRS), non-verbal pain scale (NVPS), pain assessment in advanced dementia scale (PAINAD), behavioral pain scale (BPS), critical-care pain observation tool (CPOT), or any other standardized pain scale score.

In some embodiments, the user device interface module 1316 may be triggered when the patient logs in to the user device app 1320, on the user device 1312. The user device interface module 1316 may enable the patient to extract dosages associated with a particular pain regimen of the patient. The user device interface module 1316 may continuously monitor for a dosage notification from the dosage module 1306. The user device interface module 1316 may receive the dosage notification from the dosage module 1306. For example, the user device interface module 1316 receives notification from the dosage module 1306 that the patient requires 1800 mg of painkillers on the day of his surgery, i.e., 25 mg of hydrocodone and 25 mg of CBD 4 times a day, and 500 mg of acetaminophen and 300 mg of ibuprofen twice a day. The user device interface module 1316 may facilitate displaying the dosage notification on a graphical user interface (GUI) 1318 of the user device 1312. For example, the user device interface module 1316 facilitates the display on the GUI 1318 of an indication that the patient requires 1800 mg of painkillers on the day of his surgery, i.e., 25 mg of hydrocodone and 25 mg of CBD 4 times a day, and 500 mg of acetaminophen and 300 mg of ibuprofen twice a day. In one embodiment, the user device interface module 1316 may also display risks of dependence and alternative therapies on the user device GUI 1318. In some embodiments, the user device interface module 1316 may utilize artificial intelligence (AI) to determine the risk of adverse events, including dependence, along with alternative therapies using both supervised and unsupervised training approaches.

In some embodiments, the system 1300 includes, or is in communication with, a drug administration system or device. The system 1300 may provide instructions to the drug administration system or device that indicate dosages of drugs to be administered to the patient. The drug administration system or device can be configured to control the quantity, volume, concentration, etc., of drugs administered to the patient.

In some embodiments, a drug administration device is configured to provide the patient with access to a particular dosage of tablets held in compartments. In some embodiments, the risk of addiction to opioids may be reduced by limiting the number of tablets available, allowing certain compartments to unlock at certain times of the day, on certain days, or on any schedule with medical utility. In one embodiment, a caregiver may need to unlock the compartments for the patient. In another embodiment, the dosage of drugs may be shipped or delivered to patients at appropriate times.

In some embodiments, the user device GUI 1318 may include one or more affordances that may either accept inputs from patients, facilitate displaying outputs to patients, or perform both actions. The patient can interact with the user device GUI 1318 via one or more input devices (e.g., input/output device 1925 described with respect to FIG. 19). The input devices may include user input buttons, switches, knobs, levers, keys, trackballs, touchpads, cameras, microphones, motion sensors, heat sensors, inertial sensors, touch sensors, or a combination of the above. Additionally or alternatively to the user device GUI 1318, a user interface may be implemented as a command-line interface (CLI), a voice interface, or a web-based user interface.

In some embodiments, the user device GUI 1318 may enable the patient to input data related to calendars or calendar events. In one embodiment, the user device GUI 1318 may send notifications in a user-friendly or interactive form to the patient. In some embodiments, the user device 1312 includes a user device app 1320 running on the user device 1312. In one case, the user device app 1320 is a mobile application. In another case, the user device app 1320 is a web application. In some embodiments, the user device GUI 1318 is associated with the user device app 1320 and is configured to facilitate various operations such as, but not limited to, displaying user profile, tracking the usage of the apparatus over time, logging the dose taken by the patient, tracking the dose regimen of the patient, and enabling the patient to communicate with their physician or healthcare provider. In one embodiment, the user device app 1320 may enable the patient to track the dosing. For example, the user device app 1320 may provide a user device GUI 1318 that shows the total dose provided to the patient, the maximum dose for a particular day, and the dose regimen over previous days. In one embodiment, the user device app 1320 may enable the patient to enter subjective measures that relate to the dosing, such as pain levels, intoxication levels, etc. In some embodiments, the patient may request the caregiver (e.g., a caregiver associated with the third-party device 1310) to modify the daily dose based on the subjective information. For example, the patient requests the caregiver to increase the dose of cannabinoids based on the increased pain level. In another embodiment, the patient may modify their own dose.

The functioning of the software kit database 1304 will now be explained with reference to FIG. 14. The figure (i.e., FIG. 14) shows a screenshot of a software kit database 1304 displayed by a computer device. The software kit database 1304 includes multiple indications of pharmaceutical doses of the drugs measured out in relevant periods such as hours of the day, days, weeks, months, etc. The multiple indications of pharmaceutical doses are part of a dosage scheme for a period of time. For example, the upper rows correspond to a dosage scheme for an 11-day time period and the lower rows correspond to a dosage scheme for an 8-week period of time. The software kit database 1304 includes a combination of opioids, cannabinoids (e.g., CBD), and other pain killers and/or inflammation-modulating substances in various proportions based on user parameters. The pharmaceutical doses may be in any one or a combination of forms, such as pills, capsules, tablets, transdermal patches, injections, tinctures, smokable herbs, vaporizers, or any other form in which opioids or cannabinoids may be administered. In one embodiment, the software kit database 1304 may also include indications of doses of drugs before surgery to build up cannabinoids in a patient to reduce pain immediately after surgery, since, in some embodiments, administering cannabinoids before the occurrence of pain or injury (e.g., surgical incisions) can decrease the perception of pain and the actual levels of inflammation.

For example, in FIG. 14 the software kit database 1304 includes, for 2 days before surgery, a dosage of 25 mg of CBD for the patient, twice a day. The software kit database 1304 may include indications of pharmaceutical doses of drugs measured out in relevant hours of day and days for short-term pain and inflammation modulation. For example, the software kit database 1304 includes, for the day of surgery, a dosage of 25 mg of hydrocodone and 25 mg of CBD for the patient 4 times a day, and 500 mg of acetaminophen and 300 mg of ibuprofen twice a day. The software kit database 1304 may include pharmaceutical doses of drugs measured out in week and month for long-term pain. For example, the software kit database 1304 includes, for the first week post-surgery, a dosage of 25 mg of hydrocodone and 25 mg of CBD for the patient four times a day, and 500 mg of acetaminophen and 300 mg of ibuprofen twice a day. Importantly, the software kit database 1304 provides a dosing schema that continuously decreases the level of opioids administered in direct conjunction with the levels of pain and inflammation experienced by the patient such that at the conclusion of the dosing schema, the patient's pain management regimen may include only cannabinoids and/or NSAID pain treatment but zero opioids. In this way, the patient's opioid-based treatments are gradually reduced until completely eliminated.

Figure 15:
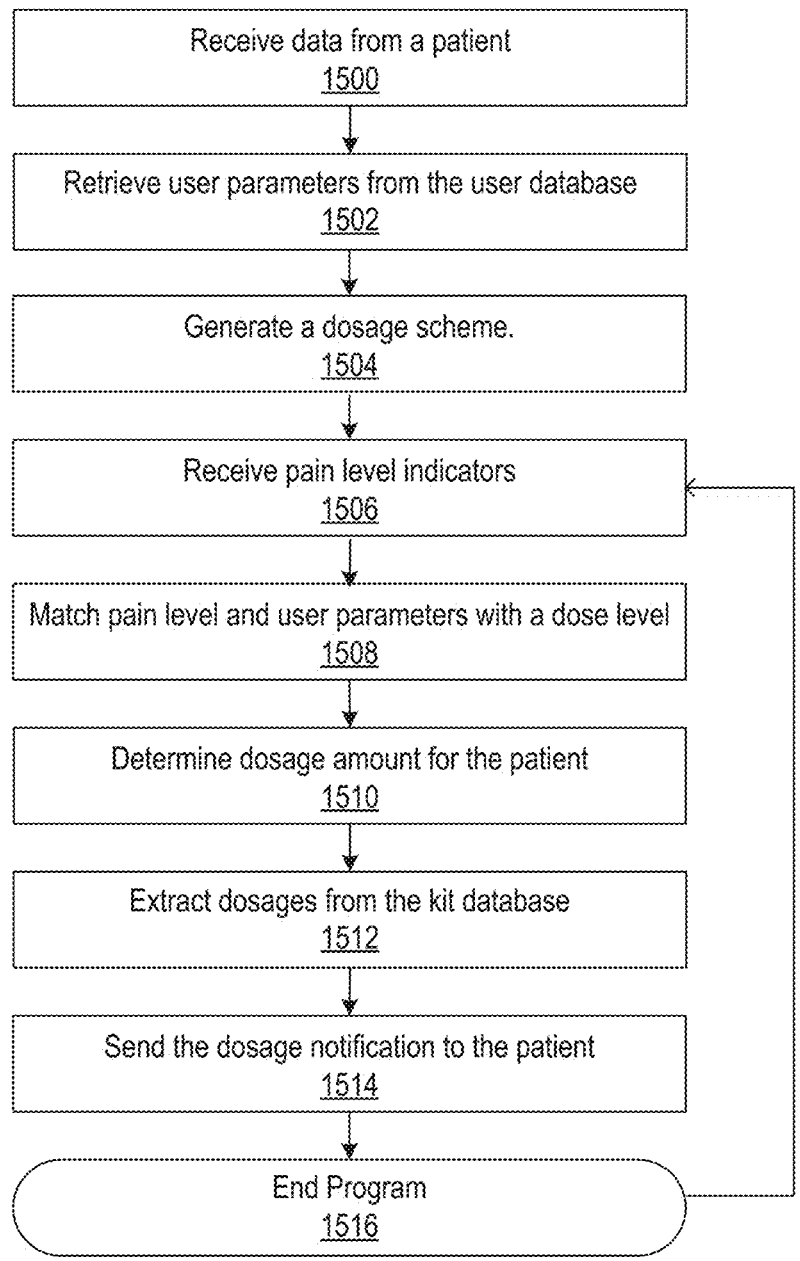
FIG. 15 illustrates a dosage module, in accordance with some embodiments.

FIG. 15 is a flowchart illustrating processes performed by the dosage module 1306 of the software kit 1302. At step 1500, the dosage module 1306 may receive data from the patient via a user device interface module 1316. In one embodiment, the data may be, but is not limited to, a pain level. For example, the dosage module 1306 receives from the user device interface module 1316 the pain level of 8 out of 10 (e.g., on a standardized pain scale) associated with the patient on the day of his surgery. The dosage module 1306 may retrieve, at step 1502, the user parameters from the user database 1314 associated with the patient. In one embodiment, the user parameters may be, but are not limited to, gender, age, weight, height, medical conditions, and disposition. The medical conditions may include medical conditions that are associated with pain or that can cause pain. The medical conditions may further include any medical conditions that may affect the effectiveness of any pain relief medications. The medical conditions may also include conditions affected by any pain relief medications. The medical conditions can be long-term or short-term. For example, the medical conditions may describe a surgery that is expected to cause pain to the patient.

In another embodiment, the user parameters may be biometric information produced by sensors worn, carried, implanted into, or in the general vicinity of the patient that allow the monitoring of physiological parameters of the patient's corporeal body. In some embodiments, the user parameters are obtained by the wearable device 1322 described above with respect to FIG. 13. For example, the dosage module 1306 retrieves the user parameters such as gender—male, age—32, weight—110 kgs, height—6'2", medical condition—diabetic, personality—strong, and disposition—4, associated with the patient from the user database 1314 and biometric data such as heart rate—60 beats per minute, respiration rate—15 breaths per minute, oxygenation levels—90%, blood-oxygen saturation (% $SpO_2$ or $SaO_2$), motor activity levels—low, pupil size—constricted, sleep profile—low REM, etc.

At step 1504, the dosage module 1306 generates a dosage scheme. The dosage scheme provides for a plan of administering opioid compounds concurrently with other pain relief medications to the patient in accordance with the patient's pain level. The dosage scheme can be adjusted based on changing pain level. For example, a first dosage scheme is associated with a first pain level, a second dosage scheme is associated with a second pain level, and a third dosage scheme is associated with a third pain level.

In some embodiments, the dosage scheme includes a scheme for administering opioid compounds to the patient concurrently with other compensating pain relief medications. The other pain relief medications may include one or more of cannabinoid compounds, NSAID compounds, and other pain relief medications. In particular, the dosage scheme includes an opioid tapering dosage scheme including multiple dosages of opioids with decreasing active ingredient amounts over a period of time. The opioid tapering dosage scheme is configured to gradually reduce the total quantity of opioids in the patient's pain-modulating regimen. To compensate for the opioid tapering, the dosage scheme further includes a cannabinoid and/or other pain relief medication dosage scheme so that an overall effectiveness of alleviating the pain of the patient remains desirable. In some implementations, the dosage scheme is generated based on a trained cannabinoid dosing machine learning model described in further detail with respect to FIG. 20.

At step 1506, the dosage module 1306 receives pain level indicators associated with the patient. The pain level indicators may include a pain level score received from the patient and/or biometric data obtained from the patient. The pain level score may correspond to a pain level score provided based on the standardized pain score scale such as the visual analog scale (VAS), numerical rating scale (NRS), defense and veterans pain rating scale (DVPRS), non-verbal pain scale (NVPS), pain assessment in advanced dementia scale (PAINAD), behavioral pain scale (BPS), or critical-care pain observation tool (CPOT). The biometric data obtained from the patient may be associated with physiological indicators of pain and may include one or more of a heart rate, a temperature, a blood pressure, a respiration rate, an oxygenation level, a motor activity level, a pupil constriction/dilation level, and sleep phase information. In some embodiments, the biometric data is obtained by the wearable device 1322 (e.g., a smartwatch, a wristband, a fitness tracker, or a wearable medical device). Exemplary levels of some physiological indicators associated with pain are listed in Table 1. The physiological indicators associated with pain in Table 1 include systolic and diastolic blood pressure (BP), resting heart rate, oxygen saturation, and respiratory rate. For example, an elevated heart rate, an elevated blood pressure (either systolic and/or diastolic), a low oxygen saturation, and a low or elevated respiratory rate may be indications that the patient is experiencing pain at a particular level.

TABLE 1

Physiological Indicators of Pain

| | Systolic BP | Diastolic BP | Resting Heart Rate | Oxygen Saturation | Respiratory Rate |
|---|---|---|---|---|---|
| Normal | 100-120 | 60-80 | 60-100 | 95%-100% | 12-16 |
| Low | <90 | <60 | <60 | <90% | <12 |
| Elevated | 120-129 | <80 | >100 | | >25 |
| High Stage 1 Hypertension | 130-139 | 80-89 | | | |
| High Stage 2 Hypertension | ≥140 | ≥90 | | | |
| High Stage 3 Hypertension | >180 | >120 | | | |

At step 1508, the dosage module 1306 may match the pain level and/or inflammation level associated with the pain level indicators, and the user parameters with a dosage level indicated based on the dosage scheme generated at step 1504. For example, the dosage module 1306 determines based on the received pain level indicators that the patient has a particular pain level (e.g., level 8/10) on a standardized pain level scale. The determination of the pain level is done based on a pain level score received from the patient as well as biometric data obtained from the patient (e.g., one or more of the exemplary physiological indicators of pain illustrated in Table 1). The dosage module 1306 then matches the particular pain level and the user parameters retrieved at step 1502 with an appropriate dosage scheme generated at step 1504. The appropriate dosage scheme includes an indication for a gradually decreasing amount of active ingredients over a period of time as well as an increasing, decreasing, or constant amount of active ingredients of other pain relief medications. In one embodiment, the dosage level and/or the dosage scheme is from the software kit database 1304. The dosage scheme includes indications of doses for opioid compounds to be administered concurrently with cannabinoid compounds and/or other pain relief medications. For example, the dosage scheme includes indications of 25 mg of hydrocodone and 25 mg of CBD 4 times a day, and 500 mg of acetaminophen and 300 mg of ibuprofen twice a day to be administered to the patient on the day of the patient's surgery.

At step 1510, based on the matching, the dosage module 1306 may determine the dosage amount for the patient. For example, the dosage module 1306 determines that the patient requires 25 mg of hydrocodone and 25 mg of CBD 4 times a day, and 500 mg of acetaminophen and 300 mg of ibuprofen twice a day, i.e., ((25×4)+(25×4)+(500×2)+(300×2)) mg=1800 mg of total pharmacologically relevant composition on the day of his surgery. In some embodiments, the dosage amount is determined based on, or extracted from, the software kit database 1304.

In one embodiment, the dosage module 1306 may determine which prescription is required for the patient. In one example embodiment, the prescription is dependent on the day associated with the surgery (such as the day of surgery or 2 days after the patient's surgery). Based on the determined dosage amount, the dosage module 1306 may extract, at step 1512, the indications of dosages from the software kit database 1304. For example, the dosage module 1306 extracts from the software kit database 1304 that the patient requires 1800 mg of a pharmacologically relevant composition on the day of his surgery. Based on the extracted dosage indications from the software kit database 1304, the dosage module 1306 may send, at step 1514, the dosage notification to the patient via the user device interface module 1316. Alternatively, the dosage notification is sent to the third-party device 1310 (e.g., to a physician or other caregiver). For example, the dosage module 1306 sends a notification to the user device interface module 1316 stating that the patient requires 1800 mg of a pharmacologically relevant composition on the day of his surgery, i.e., 25 mg of hydrocodone and 25 mg of CBD 4 times a day, and 500 mg of acetaminophen and 300 mg of ibuprofen twice a day. Thereafter, the program ends, at step 1516.

Steps 1506 through 1514 can be repeated to update the determined dosage amount for the patient based on the received pain level indicators. For example, after opioid compounds and other pain relief medications were administered to the patient in accordance with the determined dosage amount at step 1510, the patient's pain changes (e.g., increases or decreases). At step 1506, the dosage module 1306 receives updated pain level indicators from the client. At step 1508, the dosage module 1306 matches the updated pain level with an updated dose level, in accordance with the dosage scheme generated at step 1506. The dosage module 1306 further repeats the steps 1510 through 1516 accordingly.

In some embodiments, the process performed by the dosage module 1306, as described with reference to FIG. 15, further includes determining an addiction risk score for the patient based on the dosage scheme generated at step 1504 and matching of the pain level with the dose level in accordance with the dosage scheme. As steps 1506 and 1508 are repeated (e.g., the patient's pain level and dose changes), the dosage module 1306 re-determines the addiction risk score for the patient. The addiction risk score may be determined based on the patient data received at step 1500 including gender, age, weight, height, medical conditions, and disposition. In some embodiments, the method also includes comparing the re-determined addiction risk score and the original addiction risk. For example, if the dose level is changed so that the re-determined addiction risk score increases beyond a pre-defined threshold, the dosage module 1306 may re-determine the dosage level at step 1510. In some embodiments, the addiction risk score is determined based on standardized drug screening and assessment tools. Such screening and assessment tools may include the Opioid Risk Tool—Opioid Use Disorder (ORT-OUD), Opioid Risk Tool (ORT), National Institute on Drug Abuse (NIDA) Drug Screening Tool, Tobacco, Alcohol, Prescription medication, and other Substances (TAPS) tool, Screening to Brief Intervention (S2BI), Drug Abuse Screening Test (DAST-10), or any other standardized drug screening and assessment tool. Determining addiction risk scores using machine learning are discussed in connection with FIG. 18.

Functioning of the user device 1312 will now be explained with reference to FIG. 16. The figure (i.e., FIG. 16) shows a screenshot of the user database 1314 of the software kit 1302 displayed on a computer device. The user database 1314 may contain the data received by the user device interface module 1316 from the user device 1312 and/or the third-party device 1310. The user database 1314 contains the user admin data such as gender, age, weight, height, medical conditions, personality, and disposition. For example, FIG. 16 illustrates the user admin data for patients "Anthony" and "Jake." The user admin data for patient Anthony includes gender—male, age—32, weight—110 kgs, height—62" medical condition—diabetic, personality—strong, and disposition—4, and for patient Jake includes gender—male, age—24, weight—65 kgs, height—5'8", medical condition—no other condition, personality—weak, and disposition—2. Additionally, the biometric data could include a heart rate, a respiration rate, oxygenation levels, blood-oxygen saturation (% $SpO_2$ or $SaO_2$) levels, motor activity levels, pupil size, sleep profile information, etc.

Figure 17:
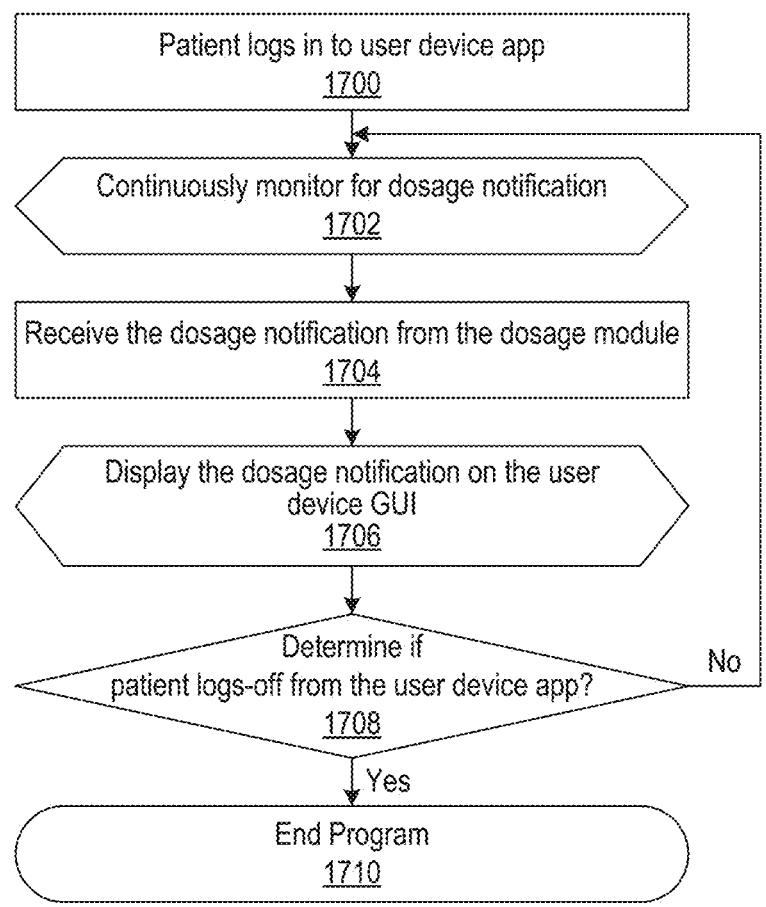
FIG. 17 illustrates a user device interface module, in accordance with some embodiments.

Functioning of the user device interface module 1316 will now be explained with reference to FIG. 17. The figure (i.e., FIG. 17) is a flowchart illustrating processes performed by the user device interface module 1316 of the user device 1312. At step 1700, the user device interface module 1316 is triggered when the patient logs in either consciously or unconsciously (e.g., via biometric-activated switch) to the user device app 1320 on the user device 1312. The user device interface module 1316 may enable the patient to extract dosages associated with a particular pain regimen of the patient. At step 1702, after the patient logs in to the user device app 1320, the user device interface module 1316 may continuously monitor for the dosage notification from the dosage module 1306. At step 1704, the user device interface module 1316 may receive the dosage notification from the dosage module 1306. For example, the user device interface module 1316 receives an indication from the dosage module 1306 that the patient requires 1800 mg of a pharmacologically relevant composition on the day of his surgery, i.e., 25 mg of hydrocodone and 25 mg of cannabidiolic acid (CBDA) or cannabidiolic acid methyl ester 4 times a day, and 500 mg of acetaminophen and 300 mg of ibuprofen twice a day.

At step 1706, the user device interface module 1316 may display the dosage notification on the user device GUI 1318. At step 1708, the user device interface module 1316 may determine if the patient logs off from the user device app 1320. In one case, if the user device interface module 1316 determines that the patient does not log off from the user device app 1320, then the user device interface module 1316 may return to step 1702 to continuously monitor for the dosage notification from the dosage module 1306. In another case, if the user device interface module 1316 determines that the patient logs off from the user device app 1320, then the program ends, at step 1710.

In some embodiments, the user device interface module 1316 may utilize the user device GUI 1318 to enable the patient to input data. Further, the user device interface module 1316 may store the input data in the user database 1314 to allow the exchange of the input data with the dosage module 1306. In one embodiment, the input data may include the user admin data such as, but not limited to, gender, age, weight, height, medical conditions, personality, and disposition. Further, the user device interface module 1316 may prompt the patient with various questions to enable the patient to input data. For example, the user device interface module 1316 may prompt the user with questions such as, but not limited to, "What is the user's gender?", "What is the user's age?", "What is the user's weight?", "What is the user's height?", "Does the user have any other medical condition?", "What is the personality of the user?", "What is the disposition level of the user?", and "What is the pain intensity?". In one embodiment, the user device interface module 1316 may provide options in one or more questions from which the patient may choose such as, but not limited to, male and female options for the question "What is user's gender?"; very weak, weak, average, strong, and very strong options for the question "What is the personality of the user?"; a 1-5 rating meter for the question "What is the disposition level of the user?"; and a 1-10 rating meter for the question "What is the pain intensity?".

In some embodiments of the present disclosure, the software kit 1302 may include an indication of a pharmacologically relevant composition consisting of one or more cannabinoids, one or more non-opioid analgesics such as acetaminophen, and one or more nonsteroidal anti-inflammatory drugs (NSAIDs). The nonsteroidal anti-inflammatory drugs (NSAIDs) may be, for example, aspirin, ibuprofen, and naproxen. In some embodiments of the present disclosure, the software kit 1302 may include an indication of a cannabinoid composition for pain management and opioid cessation. The cannabinoid composition may include one or more cannabinoids and a pain management composition, which may be pharmaceutical and/or botanical. In some embodiments of the present disclosure, the software kit 1302 may include an indication of a pharmacologically relevant composition consisting of one or more cannabinoids, one or more anesthetic or sedative compounds such as amobarbital and ketamine, and/or one or more psychedelic drugs such as psilocybin (4-phosphoryloxy-N,N-dimethyltryptamine), psilocin, lysergic acid diethylamide (LSD), mescaline, and N,N-dimethyltryptamine (DMT). "A psychedelia compound" shall mean (1) any constituent extracted or derived from a plant, fungi or animal belonging to the genuses: *Acacia, Alchornea, Amanita, Amsonia, Anadenanthera, Apocynum, Areca, Argyreia, Artemisia, Arundo, Aspidosperma, Banisteriopsis, Burkea, Calea, Calligonum, Calycanthus, Catha, Carex, Claviceps, Copelandia, Datura, Delosperma, Desfontainia, Desmanthus, Desmodium, Dictyoloma, Diplopterys, Dutaillyea, Echinopsis, Elaeagnus, Erigonum, Erythroxylum, Festuca, Guiera, Gymnacranthera, Hammada, Heimia, Horsfieldia, flex, Ipomoea, Iryanthera, Leonotis, Leptactinia, Lespedeza, Limonia, Lolium, Lophophora, Meconopsis, Melicope, Mimosa, Mitragyna, Mucuna, Nectandra, Newbouldia, Nicotiana, Nymphaea, Opuntia, Osteophloem, Panaeolus, Pandanus, Papaver, Passiflora, Pauridiantha, Peganum, Petalostylis, Phalaris, Phyllodium, Phyllomedusa, Picrasma, Pilocarpus, Plectocomiopsis, Prosopis, Psilocybe, Psychotria, Punica, Rhinella, Rivea, Salvia, Shepherdia, Simira, Strychnos, Tabernaemontana, Tabernanthe, Testulea, Tetradium, Trachelospermum, Tribulus, Uncaria, Urtica, Vepris, Vestia, Vinca, Virola, Voacanga, Zanthoxylum,* and *Zygophyllum*; (2) any compounds in the following chemical classes: arylcyclohexylamines, beta-carbolines, cathinones, ergolines, indole alkaloids, lysergamides, methylxanthine alkaloids, muscimol (and precursors), phenethylamines, salvinorins, tryptamines, Phyllomedusa peptides, and generally any compound or class of compounds categorized as "hallucinogenic substance" in schedules 1-5 of the United States Controlled Substance Act or analogues thereof; or (3) any compounds or formulations that exhibit central nervous system (CNS) activity at adenosinergic, adrenergic, cannabinergic, dopaminergic, GABA, NMDA, norepinephrine, and serotoninergic (e.g., $5\text{-HT}_{2A}$ and $5\text{-HT}_{1A}$) receptors.

In some embodiments of the present disclosure, the software kit 1302 for opioid cessation includes indications of compositions of opioids and cannabinoids in various proportions. The proportion of opioids may gradually decrease throughout the software kit 1302 compositions as the proportions of cannabinoids gradually increase. The cannabinoids may be selected for pain management therapy. The final composition of the software kit 1302 may contain zero or a negligible quantity of opioids.

In some embodiments of the present disclosure, the software kit 1302 is configured to match cannabinoids and other *Cannabis* components with nutritional supplements for synergistic and/or additive effects. The matching may include assessing the intended effect of a nutritional supplement and matching it with the cannabinoid extract with the most synergistic properties.

In some embodiments of the present disclosure, the software kit 1302 may be programmed either by a human or by an artificial intelligence mechanism to drastically change the course of the dosage regimen in response to a deleterious signal or pattern from the data interface. For example, low $SpO_2$ levels may lock dispensing functions of the entire pharmacologically active composition or one or more of the component elements to avoid serious adverse events.

In some embodiments of the present disclosure, the software kit 1302 may include an indication for a multi-compartment capsule with a cannabinoid extract and a nonsteroidal anti-inflammatory drug. The patient may take both compartments of the capsule simultaneously or split the capsule to individually select only cannabinoid or only NSAID dosages.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Included examples of classes of pharmacologically active compounds and compositions are intended for illustrative purposes and are not intended to be limited by those explicitly disclosed examples.

Processes for Training Machine Learning Models

Figure 18:
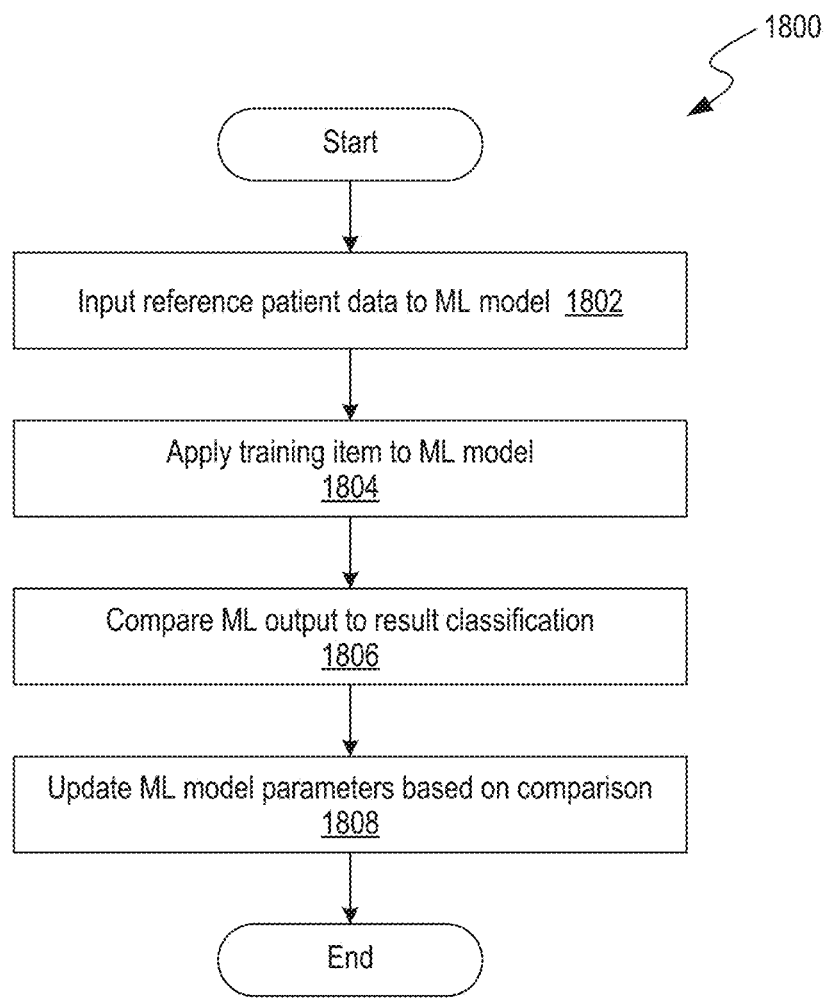
FIG. 18 illustrates a flowchart showing a method for training a machine learning model, in accordance with some embodiments.

FIG. 18 illustrates a flowchart showing a method 1800 for training a machine learning model, in accordance with some embodiments. Machine learning models, such as neural networks, can be trained to produce types of results. A neural network can be trained by obtaining, at block 1802, a quantity of "training items," where each training item includes input similar to input the model will receive when in use and a corresponding scored result. At block 1804, the input from each training item can be supplied to the model to produce a result. At block 1806, the result can be compared to the scored result. At block 1808, model parameters can then be updated, based on how similar the model result is to the scored result and/or whether the score is positive or negative. The method 1800 can be used to generate one or more trained machine learning models for outputting any of the following: dosing schemes for a combination of opioid compound(s) with cannabinoid compound(s), and/or other therapeutic compound(s), therapeutically effective amounts corresponding to a particular pain level (e.g., on a standard pain scale) over a period of time, prediction of a future pain level within a period of time, therapeutic effect, risk scores, etc. The steps of the method 1800 can be selected based on the inputs and desired output and are discussed below.

At block 1802, model input can include, without limitation, reference patient data and reference drug scheme data. The reference patient data (e.g., data from the software kit database 1304 of FIG. 13) may include pain level, gender, age, weight, height, medical conditions, personality, disposition, and so forth. The reference patient data may further include data associated with pain alleviation, opioid addiction, cannabinoid addiction, opioid efficacy in alleviating pain, and/or cannabinoid efficacy in alleviating pain. The reference drug scheme data may include indications of opioid compound dosages administered to a patient in accordance with an opioid tapering dosage scheme and indications of cannabinoid and/or other pain relief compound dosages administered to the patient in accordance with a respective cannabinoid and/or other pain relief compound dosage scheme. The training data input can be classified and/or paired with results to create training items. The classification can be selected based on the model characteristics and output. The results for training items can be, for example, patient feedback to model outputs (e.g., a pain score on a standardized scale), healthcare-provided suggestion feedback (e.g., whether the healthcare-accepted model provided recommendations completely, or made certain changes, or disregarded), biometric data associated with physiological indicators of pain (e.g., a heart rate, a temperature, a blood pressure, a respiration rate, an oxygenation level, a motor activity level, a pupil constriction/dilation level, and sleep phase information) analyzed to determine a pain score, the existence of certain positive or negative patient experiences with respect to pain alleviation, patient-reported measures and functional scores using standard scoring systems such as SF-36, OSI, NDI, WOMAC, EQ-5D, PROMIS, Oxford Hip and Knee scores, or similar outcome scoring systems, can be utilized as a proxy measure for pain and function, and can be used to refine the personal dosing schemes, settings, or the like. In addition, patient-reported measures and functional scores using standard scoring systems such as SF-36, OSI, NDI, WOMAC, EQ-5D, PROMIS, Oxford Hip and Knee scores, or similar outcome scoring systems, can be utilized as a proxy measure for pain and function, and can be used to refine the personal dosing schemes, settings, etc. The biometric data associated with physiological indicators may include objective data, such as personal data collected by biometric or wearable devices. The user feedback may result in refined personal dosing schemes, recommended products, recommended settings, etc. The data discussed in connection with FIG. 15 can be used as model input, model selection, etc. The input, subject scoring, and other information can be collected via, for example, a user device (e.g., user device 1312 of FIG. 13), input/output devices (e.g., input/output devices 1925 of FIG. 19, etc.). In some embodiments, user feedback is aggregated. Aggregated user feedback may be used to develop and refine a heuristic algorithm to provide schemes, recommendations, etc., to new patients, patients using new substances, or the like.

At block 1804, input from each training item can be supplied to the model to produce a result or output. The output can be converted to arrays of integers that, when provided to the machine learning model, produce values that specify dosing schemes for opioid compounds to be administered concurrently with cannabinoid and/or other pain relief medication compounds. Any number of models can be generated to recommend dosing schemes.

At block 1806, results can be compared to the scored result or result classification. For example, result dosing schemes can be compared to actual dosing schemes used by reference patients that produced the training item. The model can correlate the dosage schemes information to predicted patient experience. The dosage schemes can indicate any combinations of opioids, cannabinoids, and other pain relief medication compounds administered with any active ingredient amounts (e.g., by concentrations, volumes, weights), any types of compound formulations (e.g., pills, capsules, tablets, transdermal patches, injections, tinctures, smokable herbs, vaporizers, or any other form), dosage frequency, time period of administering the compounds, etc.

At block 1808, model parameters can be updated, based on how similar the model result is to the scored result and/or whether the score is positive or negative. The model parameters can then be adjusted so that the model output is more like the prior dosing scheme and patient experience if that prior patient experience was a success, or less like the prior dosing scheme if the prior patient experience was unsuccessful (e.g., pain alleviation not successful, other undesired side effects, etc.). The amount of adjustment to the model parameters can be a function of how different the model prediction was from the actual dosing scheme used and/or the level of success or failure of the product usage. Machine learning models can be trained to produce various results, such as to provide fast reduction of the opioid compound in the dosage scheme, target alleviation of pain, target types of compound formulations, target combination of the opioid compensating compounds including cannabinoid and/or other pain-relieving compounds, or the like. Models can be grouped or classified based on patient characteristics, such as patient sensitivity.

The method 1800 can generate dispensing schemes based on a patient's profile, previous sensor data for that patient, and/or information and/or sensor data from a plurality of other patients. In some embodiments, a health state is quantified as a score or metric representing the patient's overall health status and/or risk, which can be generated based on any suitable combination of sensor data and/or other data. In some embodiments, patient-specific settings or recommendations may be based upon, for example, the health state, specific patient's experience feedback, etc. The patient experience feedback may query the patient for a variety of parameters (e.g., the standardized pain scale scores, query to overall well-being of the patient, etc.). Questions may solicit information regarding, for example, the patient's experience with respect to pain alleviation, the patient's mood, the patient's fatigue level/sleep deprivation, the patient's appetite, the patient's activity and mobility, etc. For example, a model can be trained using sets of patient feedback and corresponding scores for usage. The sets of patient feedback and corresponding scores can be in accordance with standard scoring systems such as SF-36, OSI, NDI, WOMAC, EQ-5D, PROMIS, Oxford Hip and Knee scores, or similar outcome scoring systems.

In some embodiments, multiple machine learning training procedures can be performed. Example procedures can include obtaining suitable training data sets associated with a result, applying each training data set to the model, and updating model parameters based on comparison of the model result to the training set result. Each model can be designed for a different result. A neural network can be trained by obtaining a quantity of "training items or data sets," where each training item or data set includes input similar to input the model will receive when in use and a corresponding scored result. The input from each training item/data set can be supplied to the model to produce a result. The result can be compared to the scored result. Model parameters can then be updated based on how similar the model result is to the scored result and/or whether the score is positive or negative. A training procedure can include clustering, predictive analysis, etc., as discussed above. The training procedure can be selected based on the amount, quality, and/or characteristics of the data.

The method 1800 can generate risk scores for the patient. In some embodiments, the method 1800 includes determining an addiction risk score for the patient using a machine learning model. The machine learning model can be trained using training data sets containing patient risk factor data (e.g., history of drug abuse, methadone use, chronic opioid use, comorbid illness, number of physicians, etc.) In some training routines, the training data sets include, without limitation, standardized drug screening and assessment scores. Such screening and assessment scores may include, scores from one or more of the ORT-OUD, ORT, NIDA Drug Screening tool, TAPS tool, S2BI test, DAST-10, or any other standardized drug screening and assessment tool. The trained machine learning model can analyze patient data (e.g., patient data received at step 1500 of FIG. 15) to identify risk scores, predicted addition outcomes, and other addition related predictions. A dosage scheme can be generated or adjusted based on the based on the addiction risk score for the patient. This allows a healthcare professional monitor addition risk throughout treatment. If the patient becomes addicted, the patient data set can be used to retrain the machine learning model.

The machine learning model can also be trained to generate an adjusted dosage scheme based on the addiction risk score to, for example, keep an addition risk score below an threshold level. The threshold level can be set a physician, healthcare provider, or user can be related to usage time. For example, a threshold level for 1 month of continued opioid use can be equal to or less than 2.5%, 5%, 10% likelihood of continued opioid use. A threshold level for 1 year of continued opioid use can be equal to or less than 5%, 10%, 20%, or 30% addiction risk score for likelihood of continued opioid use. The planned usage information can be inputted into the model trained machine learning model such that the trained machine learning model generates a dosage scheme with an addiction risk score at or below the threshold level.

Computing Systems and Devices

In an illustrative embodiment, any of the operations, processes, etc., described herein can be implemented as computer-readable instructions stored on a computer-readable medium. The computer-readable instructions can be executed by a processor of a mobile unit, a network element, and/or any other computing device.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 19:
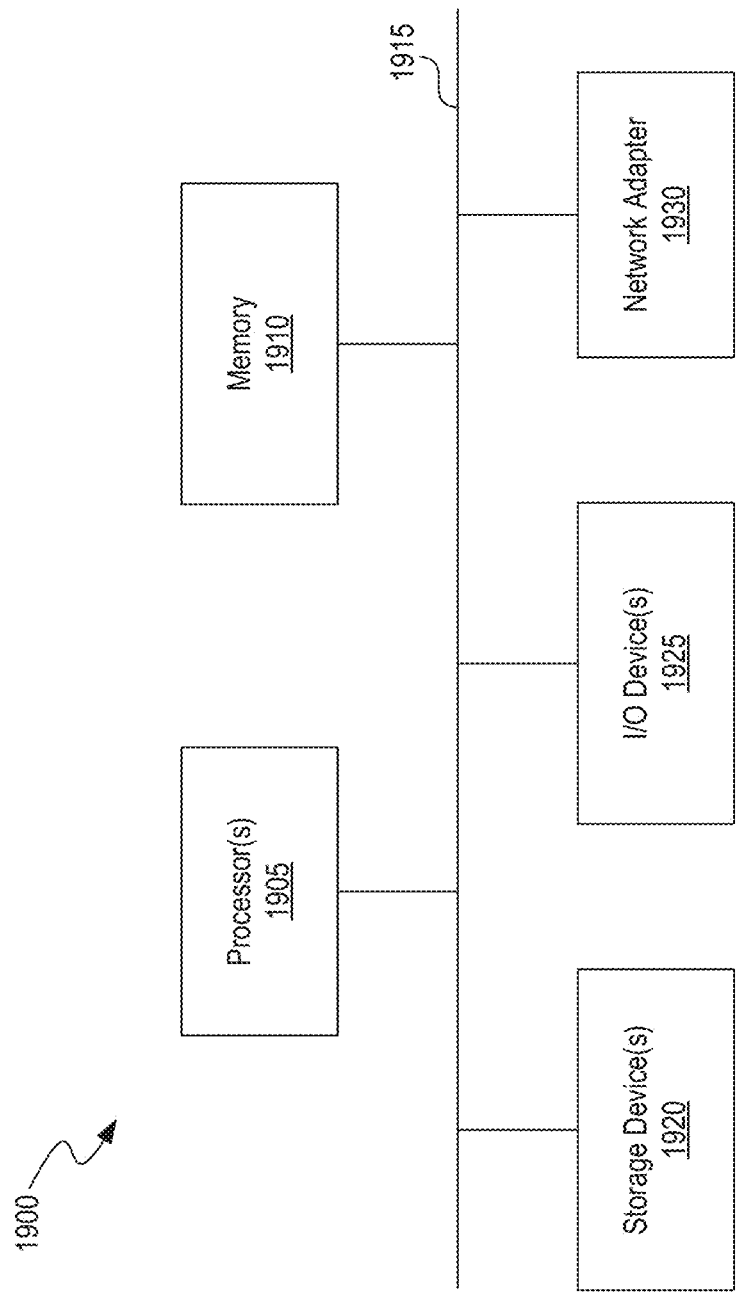
FIG. 19 is a block diagram of a computer system as may be used to implement features of some embodiments of the disclosed technology.

FIG. 19 is a block diagram of a computing system 1900 (also referred to as "a system") that may be used to implement features of some embodiments of the disclosed technology. In some embodiments, the computing system corresponds to the user device 1312, the third-party device 1310, and/or a computer device running the software kit 1302. The computing system 1900 may be used to implement any of the entities, components, or services depicted in the examples of FIGS. 13-18 (and any other components described in this specification).

The computing system 1900 may include one or more central processing units ("processors") 1905, memory 1910, input/output devices 1925 (e.g., keyboard and pointing devices, buttons, display devices, etc.), storage devices 1920 (e.g., disk drives), and network adapters 1930 (e.g., network interfaces) that are connected to an interconnect 1915. The interconnect 1915 is illustrated as an abstraction that represents any one or more separate physical buses, point-to-point connections, or both connected by appropriate bridges, adapters, or controllers. The interconnect 1915, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), an IIC (I2B) bus, or an Institute of Electrical and Electronics Engineers (IEEE) standard 1394 bus.

The memory 1910 and storage devices 1920 are computer-readable storage media that may store instructions that implement at least portions of the described technology. In addition, the data structures and message structures may be stored or transmitted via a data transmission medium, such as a signal on a communications link. Various communications links may be used, such as the internet, a local area network, a wide area network, or a point-to-point dial-up connection (e.g., a Bluetooth connection). Thus, computer-readable media can include computer-readable storage media (e.g., "non-transitory" media) and computer-readable transmission media.

The instructions stored in memory 1910 can be implemented as software and/or firmware to program the processor(s) 1905 to carry out the actions described above. In some embodiments, such software or firmware may be initially provided to the computing system 1900 by downloading it from a remote system through the computing system 1900 (e.g., via network adapter 1930).

The technology introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

The input/output devices 1925 may include input devices such as keyboards, mice, trackpads, trackballs, touchpads, touch mice, multi-touch touchpads and touch mice, microphones, multi-array microphones, drawing tablets, cameras, single-lens reflex (SLR) cameras, digital SLR (DSLR) cameras, CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers. Devices may include a combination of multiple input or output devices, including, for example, touch screens, physical buttons, microphones, fingerprint readers, accelerometers, vibration devices, etc. Some devices allow gesture recognition inputs by combining some of the inputs and outputs. Some devices allow for facial recognition, which may be utilized as an input for different purposes, including authentication and other commands. Such devices allow for voice recognition and inputs, including, for example, Microsoft Kinect, Siri for iPhone by Apple, Google Now, or Google Voice Search. Additional mobile devices have both input and output capabilities, including, for example, haptic feedback devices, touchscreen displays, or multi-touch displays. Touchscreen, multi-touch displays, touchpads, touch mice, or other touch sensing devices may use different technologies to sense touch, including, for example, capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, for example, pinch, spread, rotate, scroll, or other gestures. Some touchscreen devices, including, for example, Microsoft PixelSense or Multi-Touch Collaboration Wall, may have larger surfaces, such as on a tabletop or a wall, and may also interact with other electronic devices. Some I/O devices, display devices, or groups of devices may be augmented reality devices.

Figure 20:
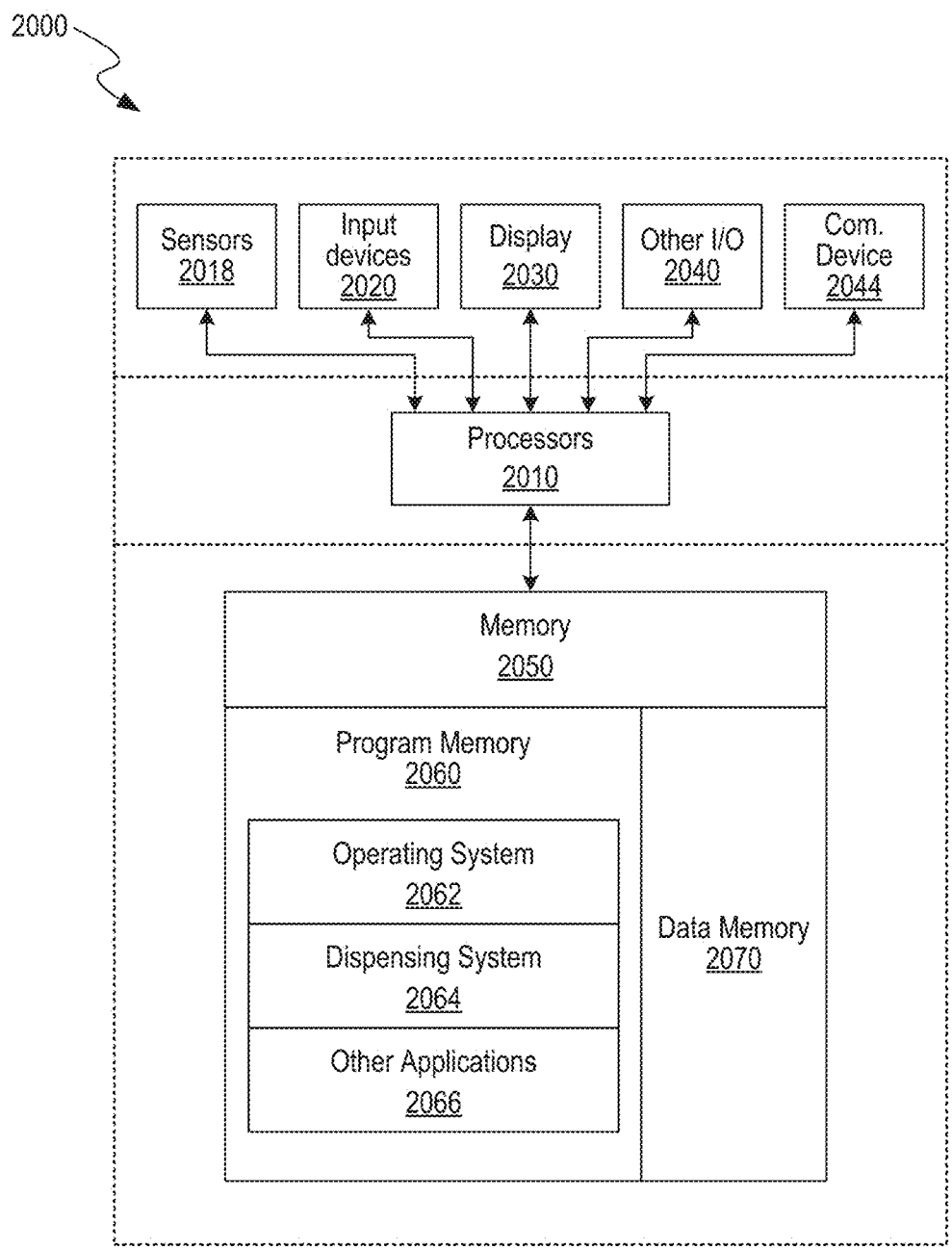
FIG. 20 is a block diagram illustrating an overview of a system on which some implementations of the disclosed technology can operate, in accordance with some embodiments.

FIG. 20 is a block diagram illustrating an overview of a system 2000 on which some implementations of the disclosed technology can operate. In some embodiments, the system 2000 corresponds to the user device 1312, the third-party device 1310, and/or a computer device running the software kit 1302. The system 2000 may be used to implement any of the entities, components, or services depicted in the examples of FIGS. 13-18 (and any other components described in this specification).

The system 2000 can include one or more sensors 2018 and input devices 2020 that provide input to a processor(s) 2010 (e.g., CPU(s), GPU(s), HPU(s), etc.), notifying it of, for example, adverse event(s), operation, and/or actions. The input can be mediated by a hardware controller that interprets the signals received from the input device and communicates the information to the processors 2010 using a communication protocol. The processors 2010 can be a single processing unit or multiple processing units in a device or distributed across multiple devices. The processors 2010 can be coupled to other hardware devices, for example, with the use of a bus, such as a PCI bus or SCSI bus. The processors 2010 can communicate with a hardware controller for devices, such as for a display 2030. Display 2030 can be used to display text, graphics, indicators, etc. In some implementations, display 2030 provides graphical and/or textual visual feedback (e.g., dosage information, pain level scores, biometric data, other user-associated data) to a patient. In some implementations, display 2030 includes the input device as part of the display, such as when the input device is a touchscreen. Examples of display devices are an LCD display screen, an LED display screen, a projected or augmented reality display, such as a heads-up display device or a head-mounted device, and so on. For example, an augmented reality display can display dosing information in a virtual environment (e.g., a virtual environment for meditation, therapy, etc.). Other I/O devices 2040 can also be coupled to the processor, such as a user device (e.g., user device 1312), network card, video card, audio card, USB, firewire or other external device, camera, speakers, etc. In some embodiments, the system 1300 also includes a communication device 2044 capable of communicating wirelessly or wire-based with a network node. The communication device can communicate with another device or a server through a network using, for example, TCP/IP protocols. The system 2000 can utilize the communication device to distribute operations across multiple network devices.

The processors 2010 can have access to a memory 2050 in a device or distributed across multiple devices. A memory includes one or more of various hardware devices for volatile and non-volatile storage, and can include both read-only and writable memory. For example, a memory can include random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 2050 can include program memory 2060 that stores programs and software, such as an operating system 2062, a dispensing or dosing system 2064 ("dispensing system 2064"), and other application programs 2066. Memory 2050 can also include data memory 2070, e.g., authentication information (e.g., cartridge authentication, user authentication, liquid composition authentication, etc.), biometric data, compound data, cartridge data, notification data, user personal health information, configuration data, settings, user options or preferences, etc., which can be provided to the program memory 2050 or any element of the system 2000.

The systems (e.g., systems 1900 and 2000) can be part of the system 1300 of FIG. 13 and other systems or components disclosed herein. For example, the user device 1312, the third-party device 1310, and/or the wearable device 1322 can include all or a portion of the systems 1900 (FIG. 19) or 2000 (FIG. 20). As another example, the software kit 1302 may be a software program or an application running on the systems 1900 (FIG. 19) or 2000 (FIG. 20). For example, the memory 2050 of the system 2000 (FIG. 20) may include instructions that, when executed by the processors 2010, cause the system 2000 to perform any of the processes described with respect to the software kit 1302, the user device 1312, the third-party device 1310, and/or the wearable device 1322, as described above with respect to FIGS. 13-18.

The systems and devices disclosed herein can be configured for machine learning model(s), such as example machine learning models discussed in connection with FIG. 18. The machine learning models can be of various types, such as Convolutional Neural Networks (CNNs), other types of neural networks (e.g., fully connected), decision trees, forests of classification trees, Support Vector Machines, etc. Machine learning models can be trained to produce particular types of results, operations, etc. For example, a training procedure can include obtaining suitable training items with input associated with a result, applying each training item to the model, and updating model parameters based on comparison of the model result to the training item result. The machine learning model(s) can be generated by, for example, the cloud 1308 of FIG. 13 using data from the software kit database 1304 of FIG. 13.

Figure 21:
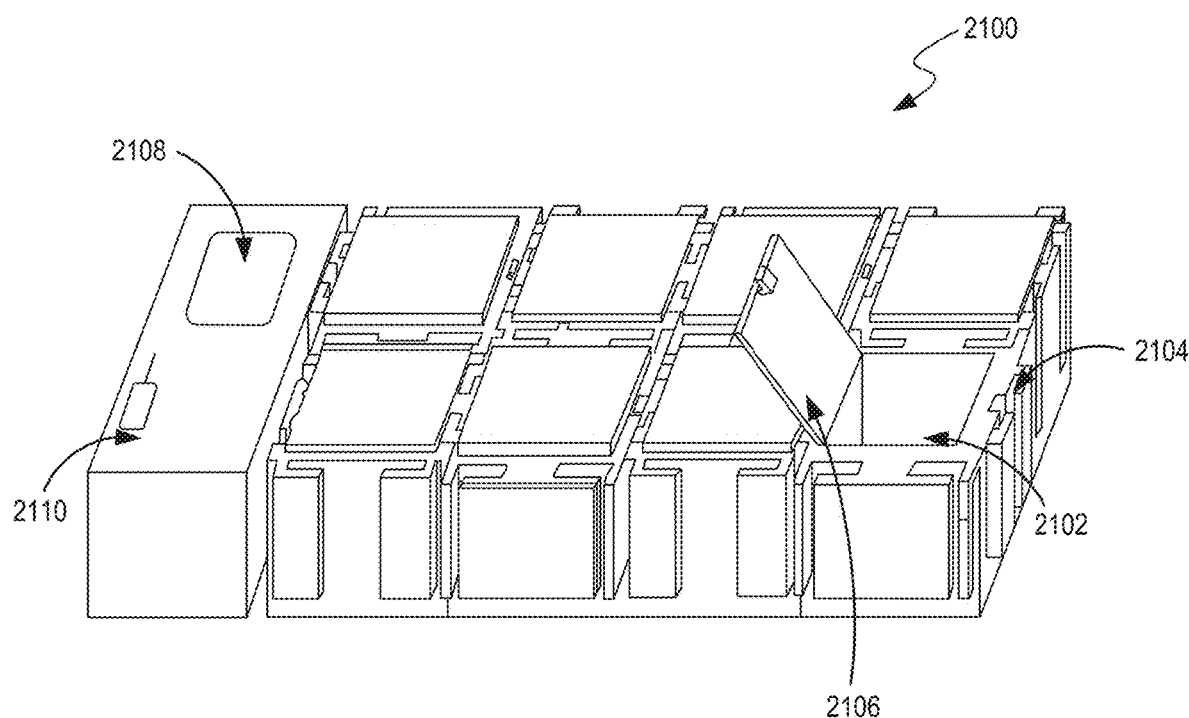
FIG. 21 illustrates a dispensing system, in accordance with some embodiments.

FIG. 21 illustrates a dispensing system 2100, in accordance with some embodiments. In some embodiments, the dispensing system 2100 corresponds to the dispensing system 1324 or the dispensing system 2064 described with respect to FIGS. 13 and 20, respectively. The dispensing system 2100 can include multiple compartments 2102 for storing medicines for medication administration based upon, for example, identification of the patient, verification of the correct medication, verification of indication for use, verification and calculation of correct dosage, verification of dosage time, or the like. The compartments 2102 can be individually operated to dispense doses, and each compartment 2102 can include a lid 2106 and a locking mechanism 2104. The locking mechanism 2104 (e.g., a latch mechanism, an electronic bolt mechanism, etc.) can be operated electronically to unlock the lid 2106. The dispensing system 2100 can also include a receiver/transmitter unit 2110 configured to communicate with, for example, a cloud 1308, the user device 1312, and/or the kit 1302 via the cloud 1308 of FIG. 13. For example, the dispensing system 2100 can receive instructions from the user device 1312 and/or the cloud 1308 to operate the dispensing system 2100. The dispensing system 2100 can further include a controller 2108 for controlling the operations of the dispensing system 2100. For example, the controller 2108 can control the locking mechanism 2104, the lid 2106 so that the locking mechanism 2104 can unlock the lid at particular times based on the instructions received by the dispensing system 2100, or other components of the dispensing system 2100. Furthermore, the locking mechanism 2104 can keep the lid 2106 to the compartment 2102 locked during other times. This way, a user can only have access to medicines stored inside a particular compartment during those particular times based on the instructions received from the user device 1312 and/or the kit 1302 via the cloud 1308 of FIG. 13.

The dispensing system 2100 can be used in multiple modes, including an offline mode and an online mode. In offline modes, the controller 2108 can control components based on, for example, locally stored schedules, received user requests (e.g., request for medication from the user and/or healthcare provider), and/or trigger events. The schedules can be from a physician, the user, or another source. For example, the schedules can be dosing schedules authenticated based on one or more verification protocols. The verification protocol can be used to perform one or more authentication routines to confirm that the schedule is from the patient's physician or healthcare provider. The dispensing system 2100 can dispense medication based on a user request that is approved based on, for example, the user request meeting one or more dispensing criteria, such as the patient experiencing a threshold pain level, patient vitals being within a dispensing range, etc. In some embodiments, the user request can be sent to the patient's healthcare provider or physician. The healthcare provider or physician can review the user request and approve or reject it. If the user request is approved, the approval can be sent to the dispensing system 2100. The dispensing system 2100 can then dispense the medication according to the approval.

The dispensing system 2100 can be used in offline modes of operation. The dispensing system 2100 can locally store authentication routines that can be used to authenticate the user. If the user needs medication, the user can input a medication request to the controller 2108. The user can then input biometric information used by the controller 2108 to authenticate the user. If the user is authenticated and dosing criteria are met, the controller 2108 can send commands to the locking mechanisms 2104 to open the appropriate compartment(s) 2102. The dispensing system 2100 can have a display that includes administration instructions (e.g., identify pills, number of pills, etc.), when medication should be administered, how medication should be administered, etc. If the controller 2108 determines additional information is needed, the controller 2108 can display and/or send information request to a user device, such as a smartphone, smartwatch, or the like. The user can then input the requested information to complete authentication, generate administration recommendations, generate schedules, or the like.

The controller 2108 can then open or unlock the appropriate compartment(s) 2102. Each compartment 2102 can have a dosage monitoring device for analyzing contents. The dosage monitoring device can include, without limitation, one or more cameras, scales, optical sensors, or other imaging devices for obtaining data related to the contents of the compartments. The controller 2108 can analyze the data to, for example, identify individual dosage, type of dosages (e.g., types of pills), and/or other information. The dispensing system 2100 can locally analyze the data to confirm proper dosing prior to administration, thereby protecting the patient from having access to improper medication. The dispensing system 2100 can also analyze its contents after administration to confirm that the appropriate dosage has been administered to the patient. This allows the dispensing system 2100 to track patient compliance.

The controller 2108 can identify trigger events for unlocking or opening compartment(s) 2102. In some embodiments, the controller 2108 can receive information from a wearable biometric device. The controller 2108 can identify a trigger event based on stored trigger settings inputted by, for example, physician, patient, or the like. For example, if the patient experiences excessive discomfort or pain, the biometric sensor can send data indicating an altered physiological state associated with the excessive discomfort or pain. The controller 2108 can determine that the user's discomfort or pain level has reached or exceeded a threshold level. The controller 2108 can then automatically open compartment(s) 2102 for dispensing medication selected to achieve a target outcome (e.g., reduce or eliminate discomfort or pain, reduce anxiety, relax the patient, prepare the patient for a procedure, etc.). The trigger events can include, for example, excess discomfort or pain, scheduled administration schedules, patient non-compliance, etc.

The dispensing system 2100 can notify the user that, for example, medication should be administered, the dispensing system 2100 has medication for administration, a compartment has been opened for medication administration, medication has been removed, or the like. The notification can be an audible alert (e.g., audible output from a speaker of the dispensing system 2100), a visual alert (e.g., a flashing light of the dispensing system 2100), and/or an alert sent to a user device, such as a user's smartphone or wearable device. The compartment 2102 can analyze its contents to confirm that the user has removed the appropriate dosage. If the user removes the appropriate dosage, the dispensing system 2100 can confirm compliance and send notifications to a user device, physician platform, or another device to track patient compliance. If the user removes an inappropriate dosage, the user can be notified that additional medication should be administered to meet the targeted dosage. The dispensing system 2100 can analyze the compartments 2102 and then specific 2102 and specific items (e.g., pills) to be administered to meet the targeted dosage. This allows the dispensing system 100 to notify the user that medications should be administered, monitor patient compliance, and notify the user if additional medications should be administered. The dispensing system 100 can also automatically refill prescriptions, notify the user when compartments 2102 should be refilled, and/or send administration notification(s).

A patient can use the dispensing system 2100 to analyze and log adverse events. For example, a user can input event information via a keyboard of the controller 2108. The information can be transmitted to a healthcare provider, physician, or another user. The dispensing system 2100 can confirm that the event has reached a sufficient level to dispense medication. For example, the dispensing system 2100 can receive pain information from the user. If the user experiences pain that exceeds a threshold level, the dispensing system 2100 can determined that the event is an adverse event (e.g., an adverse event for dispensing a dosage). The dispensing system 2100 can then allow the user to access medication to address the adverse event. The user can also receive instructions for taking the medication to avoid excess administration of medication consumption. The dispensing system 2100 can determine doses of medication suitable for addressing the adverse event while reducing or limiting the risk of addiction.

The dispensing system 2100 can operate as a hub for managing patient care and can receive (periodically or continually) information from one or more user devices, healthcare provider devices, etc. The dispensing system 2100 can determine whether to dispense medication based on the received information. In some embodiments, the dispensing system 2100 can receive patient information from, for example, smartwatches, smart rings, and other devices capable of obtaining patient information. The dispensing system 2100 can then send information to those devices based on the received patient information. For example, the dispensing system can send notifications and commands to the user devices to, for example, notify a user when medication should be taken, activities that should be performed (e.g., standing, walking, etc.), or the like. In some embodiments, the dispensing system 2100 can control medical equipment, such as respirators, glucose monitors, blood pressure measuring devices, and/or equipment for tracking pain levels. This allows the dispensing system 2100 to manage multiple devices to provide patient-specific care and medication routines.

Exemplary Embodiments of the Present Disclosure

In accordance with some embodiments, a method for reducing opioids in a pain-modulating regimen of a patient is performed by a computer system (system 1900 in FIG. 19 or system 2000 in FIG. 20). The method includes generating, by a computer system, a dosage scheme (e.g., the dosage scheme illustrated in FIG. 14) for the patient based on parameters associated with a health condition of the patient (e.g., patient data illustrated in FIG. 16). The dosage scheme includes a first dosage scheme for an opioid compound and a first dosage scheme for a cannabinoid compound. The opioid and the cannabinoid are to be administered to the patient concurrently over a period of time (e.g., a week, two weeks, a month). The first dosage scheme for the opioid compound includes a first plurality of dosages with a decreasing amount of an active ingredient in the opioid compound over the period of time. The method also includes determining an addiction risk score for the patient based on the dosage scheme and determining whether to adjust the dosage scheme based on the addiction risk score for the patient. In response to determining to adjust the dosage scheme, the method includes generating an adjusted dosage scheme based on the pain level indicators.

In some embodiments, the method also includes receiving pain level indicators associated with the patient. The pain level indicators include a first pain level indicator based on an input from the patient and a second pain level indicator based on biometric data obtained by a wearable device (e.g., wearable device 1322 in FIG. 13). The wearable device is configured to be worn by the patient. The method includes determining, by the computer system, whether to adjust the dosage scheme based on the pain level indicators. In response to determining to adjust the dosage scheme, the method includes generating an adjusted dosage scheme based on the pain level indicators. The adjusted dosage scheme includes a second dosage scheme for the opioid compound. The adjusted dosage scheme is different from the first dosage scheme for the opioid compound to be administered to the patient.

In some embodiments, the method includes determining based on the received pain level indicators at least one relationship between pain-reduction efficacy of the cannabinoid compound and pain-reduction efficacy of the opioid compound. The adjusted dosage scheme is generated based on the determined at least one relationship and has a predicted pain score that is less than a maximum pain score. For example, based on the input received from the patient and the biometric data obtained by the wearable device, and the dosage of the cannabinoid compound or the opioid compound, the system determines the pain-reduction efficacy of the cannabinoid or opioid compound, respectively. The determined relationship may then be used to predict a pain score for a patient receiving cannabinoid and/or opioid compounds according to the dosage scheme or the adjusted dosage scheme.

In some embodiments, the first dosage scheme for the cannabinoid compound includes a second plurality of dosages with an increasing amount of an active ingredient in the cannabinoid compound over the period of time. The cannabinoid compound dosages are thereby configured to compensate for the reducing amount of the active ingredient in the cannabinoid compound over the period of time.

In some embodiments, the dosage scheme further includes a third dosage scheme for a pain relief medication to be administered to the patient concurrently. The pain relief medication can include non-steroidal anti-inflammatory drugs (e.g., aspirin, ibuprofen, and naproxen) and other drugs, plant-derived extracts and complex mixtures (e.g., kratom, turmeric, white willow, and Boswellia), and mind-body techniques (e.g., acupuncture and meditation).

In some embodiments, the biometric data obtained by the wearable device includes one or more of a heart rate, a temperature, a blood pressure, a respiration rate, an oxygenation level, a motor activity level, a pupil constriction/dilation level, and sleep phase information. The biometric data may correspond to physiological indicators associated with pain, such as those included in Table 1.

In some embodiments, the method includes transmitting, by the computer system to a user device (e.g., the user device 1312 in FIG. 13) associated with the patient, instructions to administer the opioid compound and the cannabinoid compound to the patient in accordance with the adjusted dosage scheme. The transmitting is performed in response to receiving the pain level indicators associated with the patient. In some embodiments, the instructions include times, amounts, types, and methods of administering the opioid compound and the cannabinoid compound to the patient.

In some embodiments, the opioid compound and the cannabinoid compound are independently administered as pills, capsules, tablets, transdermal patches, injections, tinctures, smokable herbs, or as an inhalable vapor. For example, the opioid compound is administered as an injection and the cannabinoid is administered as an inhalable vapor. As another example, both the opioid and the cannabinoid are administered as tablets.

In some embodiments, the dosage scheme and the adjusted dosage scheme are configured to gradually reduce the opioid compound from the pain-modulating regimen of the patient by replacing the opioids with the cannabinoid compound. For example, as shown in FIG. 14, the opioid dose is reduced gradually from the day of the surgery to 8 days post-surgery.

In some embodiments, the method further includes determining, by the computer system, whether an amount of opioid administered to the patient in accordance with the dosage scheme or the adjusted dosage scheme is above a threshold limit. For example, the threshold limit can correspond to an amount of opioid compound that is defined by, for example, a health official, or by a healthcare provider (e.g., a hospital, a physician, an insurance company, or government agencies (e.g., Centers for Disease Control and Prevention (CDC), Federal Drug Administration (FDA), etc.) to be, for example, a maximum amount of opioid that a user can consume. The threshold limit may be defined per dosage unit, per day (e.g., defined daily dose), per week, etc. The threshold limit may depend on the patient's biometric information such as weight, age, health conditions, or the addiction risk score. The method further includes reducing the amount of opioid compounds administered to the patient in an instance where the amount of opioids is above the threshold limit.

In some embodiments, the computer system generates the adjusted dosage scheme partially based on an input received from a user of the computer system. For example, a physician may provide an input to adjust (e.g., increase or decrease) the amount of opioids to be administered to the patient, dosage times, or dosage intervals. In some instances, the computer system determines whether the amount of opioids administered to the patient is above the threshold limit described above. In accordance with a determination that the amount of opioid administered to the patient is above the threshold limit, the computer system provides an indication (e.g., a warning icon or a pop-up window) to the user. Such indication is configured to prevent instances of overprescribing.

In some embodiments, the computer system further provides indications (e.g., icons, pop-up windows, or other indications) indicating when the dosage scheme or the adjusted dosage scheme does not correspond to an appropriate medical billing code. For example, administering opioids under a medical billing code for surgery may be appropriate while administering opioids under a medical billing code for a toothache is not appropriate. The medical billing codes may further include limitations for administering opioids. For example, a medical billing code for surgery may allow a certain amount of opioids to be administered for a certain period of time to be covered by federal or state health coverages or by health insurance companies. The computer system will provide an indication in an instance where the amount of opioids is higher than the covered amount. Such indication is configured to prevent the administration of medications that are not covered by federal or state health coverages or by health insurance companies. In some embodiments, the computer system can generate dosing schemes based on reimbursement information, such as reimbursement billing and coding. For example, the computer system can determine dosage schemes ensure compliance and payment coverage by Centers for Medicare & Medicaid Services (CMS), insurance provider, or the like. The computer system can search for and retrieve, for example, codes, dosing limits, threshold limits, and other information from third party databases, such as FDA databases, CMS databases, CDC databases, etc. Patient dosing scheme can also be generated based on reporting requirements.

In some embodiments, the method further includes determining an addiction risk score for the patient based on the dosage scheme and determining an adjusted addiction risk score for the patient based on the adjusted dosage scheme (e.g., as described with respect to FIG. 15). The addiction risk score may be determined based on the patient data including pain intensity, gender, age, weight, height, medical conditions, personality, and disposition (e.g., history of prior addictions). The method also includes comparing the addiction risk score and the adjusted addiction risk score to determine whether the second dosage scheme meets at least one addiction risk criterion. In some embodiments, the addiction risk score is determined based on standardized drug screening and assessment tools. Such screening and assessment tools may include the Opioid Risk Tool-Opioid Use Disorder (ORT-OUD), Opioid Risk Tool (ORT), National Institute on Drug Abuse (NIDA) Drug Screening Tool, Tobacco, Alcohol, Prescription medication, and other Substances (TAPS) tool, Screening to Brief Intervention (S2BI), Drug Abuse Screening Test (DAST-10), or any other standardized drug screening and assessment tool.

An addiction risk criterion could include a threshold for reduction of the addiction risk score. For example, meeting the addiction risk criterion includes the requirement that the addiction risk score is maintained at or above the addiction risk score "medium" or below a 30% likelihood of developing an addiction. As another example, the addiction risk criterion is met when the addiction risk score does not increase by more than 20% (e.g., the addiction risk criterion is met when the addiction risk assessment score is increased by 20% or less). In some embodiments, the addiction risk criterion includes a time frame. For example, the addiction risk criterion is met when the patient has a likelihood of developing an addiction below the threshold over a period of time (e.g., the addiction risk criterion is expected to be maintained below the threshold for a week or a month).

In accordance with some embodiments, a system (e.g., the system 1300 in FIG. 13) for eliminating opioids from a pain-modulating regimen of a patient is disclosed. The system includes a computer device programmed to be in communication with a user device and a wearable device associated with the patient. The system is configured to perform the disclosed methods.

In some embodiments, the user device (e.g., the user device 1312 in FIG. 13) is configured to receive instructions to administer the opioid compound and the cannabinoid compound to the patient in accordance with the dosage scheme and the adjusted dosage scheme and display the instructions to the patient.

In some embodiments, the wearable device (e.g., the wearable device 1322) is configured to obtain the biometric data from the patient and transmit the biometric data to the computer device, thereby enabling the computer device to generate the adjusted dosage scheme. In some embodiments, obtaining the biometric data includes detecting, by one or more sensors of the wearable device, one or more of a heart rate, a temperature, a blood pressure, a respiration rate, an oxygenation level, a motor activity level, a pupil constriction/dilation level, and sleep phase information of the patient. The wearable device may be a smartwatch, a wristband, a fitness tracker, or a wearable medical device.

In accordance with some embodiments, a method for administering drugs to a patient includes generating, by a computer system, an initial dosage scheme (e.g., step 1504 in FIG. 15) for the patient based on parameters associated with a health condition of the patient. The initial dosage scheme includes a first dosage scheme for a first drug and a first dosage scheme for a second drug to be administered to the patient concurrently over a period of time. The first dosage scheme for the first drug includes a first plurality of dosages with a decreasing amount of an active ingredient in the first drug over the period of time. The method includes receiving, by the computer system, one or more health condition indicators associated with the patient. The one or more health condition indicators include an indicator based on an input from the patient. The method also includes generating, by the computer system, a subsequent dosage scheme based on the one or more health condition indicators.

In some embodiments, the method further includes administering a first set of dosages of the opioid compound and a first set of dosages of the cannabinoid compound to the patient in accordance with the dosage scheme. The method also includes administering a second set of dosages of the opioid compound and a second set of dosages of the cannabinoid compound to the patient in accordance with the adjusted dosage scheme. Administering can be done by a device coupled or in communication with the computer system. For example, the system 1300 includes or is in communication with a drug administration system or device. The drug administration system or device can be configured to control the quantity, volume, concentration, etc., of drugs administered to the patient. Alternatively, the administering is done by a person (e.g., the patient or the patient's caretaker).

In accordance with some embodiments, a method for opioid management in a pain-modulating regimen for a patient includes receiving, by a computing system, patient data of a patient. The method includes generating, by at least one trained cannabinoid dosing machine learning model, a pain relief regimen based on the received patient data. For example, the pain relief regimen is generated by a trained cannabinoid dosing machine learning model described with respect to FIG. 18. The pain relief regimen includes an opioid tapering dosage scheme and a cannabinoid dosage scheme (e.g., as shown in FIG. 14). The cannabinoid is designed to compensate for opioid tapering of the opioid tapering dosage scheme such that the pain relief regimen effectively alleviates pain of the patient whereas, in some embodiments, a cannabinoid dosage scheme that begins prior to a pain-generating event is intended to lessen the starting opioid dosage and in some cases obviate it altogether due to decreasing the magnitude of pain perceived by the patient after a pain-generating event.

In some embodiments, the pain relief regimen includes a first dosage scheme including a first opioid tapering dosage scheme for an opioid compound and a first cannabinoid dosage scheme for a cannabinoid compound to be administered to the patient concurrently over a period of time.

In some embodiments, the method further includes receiving, by the computing system, one or more pain level indicators for the patient. The pain level indicators may include patient feedback or biometric data including physiological indicators of pain (e.g., Table 1). The method includes determining whether to adjust the pain relief regimen based on the received one or more pain level indicators. In response to determining to adjust the pain relief regimen, the method includes generating an adjusted effective pain relief regimen based on a relationship between the one or more pain level indicators and an addiction risk score. An addiction risk score refers to a likelihood of a patient developing an addiction to, for example, opioids. The addiction score can include a verbal evaluation. For example, the addiction risk can be assessed as "high," "medium," or "low." Alternatively, the addiction risk can be assessed as a numerical value. For example, 10%, 20%, 30%, 40%, 50%, 60%, 70%, 80%, or 90% likelihood of developing an addiction. The addiction risk can be determined based on the patient's disposition to addiction including, for example, a history of addictive behavior, genetic disposition to addiction or drug or alcohol abuse, electroencephalogram (EEG) patterns, or functional magnetic resonance imaging (fMRI) patterns, etc. The addiction risk can also be determined based on medical conditions. For example, medical conditions associated with chronic pain or extremely high pain may increase the likelihood of developing an addiction. The adjusted dosage scheme includes a modified opioid tapering dosage scheme for reducing a risk of opioid addiction by the patient.

In some embodiments, retraining the at least one trained cannabinoid dosing machine learning model is performed by using a plurality of reference patient sets that include pain data and opioid misuse data.

In some embodiments, the method further includes receiving pain data of the patient associated with the pain relief regimen. The pain data can be received as an input from the patient or as biometric data (e.g., measured by the wearable device 1322). The method also includes using the at least one trained cannabinoid dosing machine learning model to analyze the received pain data and to identify, based on the analysis of the received pain data, one or more patient-specific correlations between opioid dosing of the opioid tapering dosage scheme and cannabinoid dosing of the cannabinoid dosing scheme. The method includes generating an adjusted pain relief regimen based on the identified one or more patient-specific correlations to alleviate pain of the patient.

In some embodiments, generating the pain relief regimen includes predicting pain levels of the patient over a period of time and determining, based on the predicted pain levels, the opioid tapering dosage scheme for at least one opioid compound and the cannabinoid dosage scheme for at least one cannabinoid compound. The predictive pain level capability also provides insight for cannabinoid pre-treatment which is a critical part of some embodiments.

In some embodiments, the method also includes determining a reduction of pain alleviation associated with opioid tapering of the opioid tapering dosage scheme over a period of time. The method includes determining the cannabinoid dosage scheme for providing pain alleviation that is substantially proportional to the reduction of pain alleviation associated with opioid tapering of the opioid tapering dosage scheme over the period of time.

In some embodiments, the method further includes comparing the patient data to a plurality of reference patient data sets to identify one or more similar patient data sets in the plurality of reference patient data sets. The similarity is based on at least one of pain alleviation, opioid addiction, cannabinoid addiction, opioid efficacy, or cannabinoid efficacy. The method includes selecting a subset of the one or more similar patient data sets that includes data indicative of a favorable pain relief and non-addiction outcome. The method also includes identifying, for at least one similar patient data set of the selected subset, one or more dosing parameters associated with the favorable pain relief and non-addiction outcome. The method includes using the one or more dosing parameters to generate the pain relief regimen.

In some embodiments, a method for dispensing opioids using a dispensing container (e.g., the dispensing system 1324 in FIG. 13 and the dispensing system 2100 in FIG. 21) in an anti-addiction pain-modulating regimen includes generating, by a computer system (e.g., the system 2000 in FIG. 20 including the software kit 1302 in FIG. 13), a dosage scheme for dispensing an opioid compound using the dispensing container including a controller programmable according to the dosage scheme and locked compartments storing the opioid compound, wherein the dosage scheme is based on one or more parameters associated with a health condition of a patient, wherein: the dosage scheme includes a first dosage scheme for an opioid compound and a first dosage scheme for a cannabinoid compound to be administered to the patient concurrently over a period of time; and the first dosage scheme for the opioid compound includes a first plurality of dosages with a decreasing amount of an active ingredient in the opioid compound over the period of time; determining an addiction risk score for the patient based on the dosage scheme; determining, by the computer system, whether to adjust the dosage scheme based on the addiction risk score for the patient; in response to determining to adjust the dosage scheme, generating, by the computer system, an adjusted dosage scheme based on the addiction risk score, wherein: the adjusted dosage scheme includes a second dosage scheme for the opioid compound that is different from the first dosage scheme for the opioid compound to be administered to the patient; sending the second dosage scheme for operating the dispensing container, wherein the controller stores one or more authentication programs and is programmed to authenticate the patient using the one or more authentication programs, and in response to authenticating the patient, unlock one or more of the compartments to allow the patient to access to a dosage of the opioid compound held in the one or more compartments according to the second dosage scheme.

In some embodiments, authentication of the patient includes acquiring biometric information from the patient, and comparing the biometric information with reference biometric information associated with the patient, wherein biometric information includes a fingerprint, voice, facial features, or retina data.

In some embodiments, the controller is further programmed to perform the authentication of the patient and unlocking of the one or more compartments at a particular time of a day that is predefined based on the adjusted dosage scheme.

In some embodiments, the dosage scheme and the adjusted dosage scheme for dispensing the opioid compound using the dispensing container are configured for pre-treating the patient prior to a surgery of an expected physiological or psychological stress.

In some embodiments, the method includes receiving, by the computer system, pain level indicators associated with the patient, wherein the pain level indicators include: a first pain level indicator based on an input from the patient; and a second pain level indicator based on biometric data obtained by a wearable device configured to be worn by the patient, and determining, by the computer system, whether to adjust at least one of the dosage scheme or the adjusted dosage scheme based on the pain level indicators.

In some embodiments, the method includes determining, based on the received pain level indicators, at least one relationship between pain-reduction efficacy of the cannabinoid compound and pain-reduction efficacy of the opioid compound, wherein the adjusted dosage scheme is generated based on the determined at least one relationship and has a predicted pain score that less than a maximum pain score.

In some embodiments, the method includes in response to receiving the pain level indicators associated with the patient, transmitting, by the computer system to a user device associated with the patient, instructions to administer the opioid compound and the cannabinoid compound to the patient in accordance with the adjusted dosage scheme.

In some embodiments, the first dosage scheme for the cannabinoid compound includes a second plurality of dosages with an increasing amount of an active ingredient in the cannabinoid compound over the period of time.

In some embodiments, the dosage scheme further includes a third dosage scheme for a pain relief medication to be administered to the patient concurrently.

In some embodiments, the method includes unlocking a first compartment to allow the patient to access a first set of dosages of the opioid compound and a first set of dosages of the cannabinoid compound in accordance with the dosage scheme; and unlocking a first compartment to allow the patient to access a second set of dosages of the opioid compound and a second set of dosages of the cannabinoid compound in accordance with the adjusted dosage scheme.

In some embodiments, the opioid compound and the cannabinoid compound stored in the locked compartments include pills, capsules, tablets, transdermal patches, injections, tinctures, smokable herbs, or inhalable vapor source.

In some embodiments, the dosage scheme and the adjusted dosage scheme are configured to gradually reduce or increase the opioid compound from the pain-modulating regimen of the patient by replacing the opioids with the cannabinoid compound.

In some embodiments, the method includes determining, by the computer system, whether an amount of opioid administered to the patient in accordance with the dosage scheme or the adjusted dosage scheme is above a threshold limit; and reducing the amount of opioid that the patient has access to in an instance where the amount of opioid is above the threshold limit.

In some embodiments, the method includes generating the adjusted dosage scheme partially based on an input received from a user of the computer system; determining, by the computer system, whether an amount of opioid administered to the patient in accordance with the adjusted dosage scheme is above a threshold limit; and in response to determining that the amount of opioid administered to the patient in accordance with the adjusted dosage scheme is above the threshold limit, providing, by the computer system, an threshold exceeded indication to the user.

In some embodiments, a system for dispensing opioids using a dispensing container in an anti-addiction pain-modulating regimen, the system including: a computer system programmed to be in communication with the dispensing container associated with a patient, the computer system configured to: generate a dosage scheme for dispensing an opioid compound using the dispensing container including a controller programmable according to the dosage scheme and locked compartments storing the opioid compound, wherein the dosage scheme is based on one or more parameters associated with a health condition of the patient, wherein: the dosage scheme includes a first dosage scheme for an opioid compound and a first dosage scheme for a cannabinoid compound to be administered to the patient concurrently over a period of time; and the first dosage scheme for the opioid compound includes a first plurality of dosages with a decreasing amount of an active ingredient in the opioid compound over the period of time; determine an addiction risk score for the patient based on the dosage scheme; determine by the computer system, whether to adjust the dosage scheme based on the addiction risk score for the patient; in response to determining to adjust the dosage scheme, generate an adjusted dosage scheme based on the addiction risk score, wherein: the adjusted dosage scheme includes a second dosage scheme for the opioid compound that is different from the first dosage scheme for the opioid compound to be administered to the patient; send the second dosage scheme for operating the dispensing container, wherein the controller stores one or more authentication programs and is programmed to authenticate the patient using the one or more authentication programs, and in response to authenticating the patient, unlock one or more of the compartments to allow the patient to access to a dosage of the opioid compound held in the one or more compartments according to the second dosage scheme.

In some embodiments, a method for dispensing firsts using a dispensing container in an anti-addiction pain-modulating regimen includes generating, by a computer system, a dosage scheme for dispensing a first compound using the dispensing container including a controller programmable according to the dosage scheme and locked compartments storing the first compound, wherein the dosage scheme is based on one or more parameters associated with a health condition of a patient, wherein: the dosage scheme includes a first dosage scheme for an first compound and a first dosage scheme for a cannabinoid compound to be administered to the patient concurrently over a period of time; the first dosage scheme is for pre-treatment of the patient prior to a surgery or physiological or psychological stress; and sending the dosage scheme for operating the dispensing container, wherein the controller stores one or more authentication programs and is programmed to authenticate the patient using the one or more authentication programs, and in response to authenticating the patient, unlock one or more of the compartments to allow the patient to access to a dosage of the first compound held in the one or more compartments according to the dosage scheme.

Example 1. CBD-Facilitated Taper

This example demonstrates that CBD is used to facilitate taper of opioid (oxycodone) use in opioid-naive patients, mildly opioid-dependent patients, and moderately opioid-dependent patients. For dosing schedules, the following abbreviations are used: BID=2 times per day, every 12 hours; PO=by mouth; QD=daily; Q4H=every 4 hours; Q6H=every 6 hours; TID=3 times per day, every 8 hours.

Tables 2-4 are examples of dosing schedules for illustration purposes only. Depending on the conditions and responses of individual patients, the dosing schedules can be adjusted accordingly.

TABLE 2

CBD-Only Facilitated Taper for Opioid-Naive Patient

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |
| Oxycodone | 5 mg Q4H (20 mg QD) | 2.5 mg Q4H (10 mg QD) | 0 mg | 0 mg | 0 mg | 0 mg |
| Cannabinol (CBD) | — | 300 mg QD divided TID | 300 mg QD divided TID | 300 mg QD divided TID | 300 mg QD divided TID | 300 mg QD divide dTID |

TABLE 3

CBD-Only Facilitated Taper for Mildly Opioid-Dependent Patient

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |
| Oxycodone | 5 mg Q4H (30 mg QD) | 4 mg Q4H (20 mg QD) | 2.5 mg Q6H (10 mg QD) | 2.5 mg Q6H (10 mg QD) | 0 mg | 0 mg |
| Cannabinol (CBD) | — | 300 mg QD divided TID | 300 mg QD divided TID | 300 mg QD divided TID | 300 mg QD divided TID | 300 mg QD divided TID |

TABLE 4

CBD-Only Facilitated Taper for Moderately Opioid-Dependent Patient

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |
| Oxycodone | 10 mg Q4H (60 mg QD) | 7.5 mg Q4H (45 mg QD) | 5 mg Q4H (30 mg QD) | 2.5 mg Q4H (15 mg QD) | 2.5 mg Q6H (10 mg QD) | 0 mg |
| Cannabinol (CBD) | — | 300 mg QD divided TID | 300 mg QD divided TID | 300 mg QD divided TID | 300 mg QD divided TID | 300 mg QD divided TID |

Example 2. CBD- and THC-Facilitated Taper

This example demonstrates that CBD and THC are used to facilitate taper of opioid (oxycodone) use in moderately opioid-dependent patients. For dosing schedules, the following abbreviations are used: BID=2 times per day, every 12 hours; P=by mouth; QD=daily; Q4H=every 4 hours; Q6H=every 6 hours; TID=3 times per day, every 8 hours.

Table 5 is an example of dosing schedules for illustration purposes only. Depending on the conditions and responses of individual patients, the dosing schedules can be adjusted accordingly.

TABLE 5

CBD- and THC-Facilitated Taper for Moderately Opioid-Dependent Patient

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |

TABLE 5-continued

CBD- and THC-Facilitated Taper for Moderately Opioid-Dependent Patient

Oral Dosing Medication Taper Sample Schedule

| | Week 1 | Week 2 | Week 3 | Week 4 | Week 5 | Week 6 |
|---|---|---|---|---|---|---|
| Oxycodone | 10 mg Q4H (60 mg QD) | 7.5 mg Q4H (45 mg QD) | 5 mg Q4H (30 mg QD) | 2.5 mg Q4H (15 mg QD) | 2.5 mg Q6H (10 mg QD) | 0 mg |
| Cannabinol (CBD) | — | 200 mg PO QD | 200 mg PO QD | 200 mg PO QD | 200 mg PO QD | 200 mg PO QD |
| Delta-9 Tetrahydrocannabinol (THC) | — | 20 mg PO BID | 20 mg PO BID | 10 mg PO BID | 10 mg PO BID | 5 mg PO |

Example 3. Psilocybin-Facilitated Dependence Awareness & Taper

This example demonstrates that psilocybin is used to facilitate taper of opioid (oxycodone) use in patients. For dosing schedules, the following abbreviations are used: BID=2 times per day, every 12 hours; PO=by mouth; QD=daily; Q4H=every 4 hours; Q6H=every 6 hours; TID=3 times per day, every 8 hours.

Table 6 is an example of dosing schedules for illustration purposes only. Depending on the conditions and responses of individual patients, the dosing schedules can be adjusted accordingly.

TABLE 6

Psilocybin-Facilitated Dependence Awareness & Taper

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |
| Oxycodone | 10 mg Q4H (60 mg QD) | 7.5 mg Q4H (45 mg QD) | 5 mg Q4H (30 mg QD) | 2.5 mg Q4H (15 mg QD) | 2.5 mg Q6H (10 mg QD) | 0 mg |
| Psilocybin (or pharmaceutical equivalent) | 0 mg | 0 mg | 20-30 mg PO (once, under supervision) | 0 mg | 0 mg | 20-30 mg PO (once, under supervision) |

Example 4. Ketamine-Facilitated Dependence Awareness & Taper

This example demonstrates that ketamine is used to facilitate taper of opioid (oxycodone) use in patients. For dosing schedules, the following abbreviations are used: BID=2 times per day, every 12 hours; PO=by mouth; QD=daily; Q4H=every 4 hours; Q6H=every 6 hours; TID=3 times per day, every 8 hours.

Table 7 is an example of dosing schedules for illustration purposes only. Depending on the conditions and responses of individual patients, the dosing schedules can be adjusted accordingly.

TABLE 7

Ketamine-Facilitated Dependence Awareness & Taper

Oral Dosing Medication Taper Sample Schedule

| | Week 1 | Week 2 | Week 3 | Week 4 | Week 5 | Week 6 |
|---|---|---|---|---|---|---|
| Acetaminophen | 3000 mg QD divided TID | 3000 mg QD divided TID | 3000 mg QD divided TID | 2000 mg QD divided TID | 2000 mg QD divided TID | 2000 mg QD divided TID |
| Ibuprofen | 600 mg PO TID | 600 mg PO TID | 400 mg PO TID | 400 mg PO TID | 200 mg PO TID | 200 mg PO TID |

TABLE 7-continued

Ketamine-Facilitated Dependence Awareness & Taper

Oral Dosing Medication Taper Sample Schedule

|  | Week 1 | Week 2 | Week 3 | Week 4 | Week 5 | Week 6 |
|---|---|---|---|---|---|---|
| Oxycodone | 10 mg Q4H (60 mg QD) | 7.5 mg Q4H (45 mg QD) | 5 mg Q4H (30 mg QD) | 2.5 mg Q4H (15 mg QD) | 2.5 mg Q6H (10 mg QD) | 0 mg |
| Ketamine | — | — | 1.0-2.0 mg/lb. body weight PO (once, under supervision) | — | — | 1.0-2.0 mg/lb. body weight PO (once, under supervision) |

Example 5. Pre-Treatment Schedules

This example demonstrates that pre-treatment in patients prior to a surgery (Table 8) and extreme physiological and/or psychological stress (Table 9). For dosing schedules, the following abbreviations are used: BID=2 times per day, every 12 hours; Pd=by mouth; TD=daily; Q4H=every 4 hours; Q6H=every 6 hours; TID=3 times per day, every 8 hours.

Tables 8 and 9 are examples of dosing schedules for illustration purposes only. Depending on the conditions and responses of individual patients, the dosing schedules can be adjusted accordingly.

TABLE 8

Pre-Treatment Schedule for Inflammasome-Modulation Treatment Prior To Surgery

Oral Dosing Medication Taper Sample Schedule

|  | Day-2 | Day-1 | Day of Surgery (Post) | Week 1 | Week 2 | Week 3 | Week . . . |
|---|---|---|---|---|---|---|---|
| Acetaminophen | — | — | 3000 mg QD divided TID | 3000 mg QD divided TID | 2000 mg QD divided TID | 2000 mg QD divided TID | . . . |
| Ibuprofen | — | — | 600 mg PO TID | 600 mg PO TID | 200 mg PO TID | 200 mg PO TID | . . . |
| Oxycodone | — | — | 5 mg Q4H (20 mg QD) | 2.5 mg Q4H (10 mg QD) | — | — | . . . |
| Cannabidiol (CBD) | 300 mg QD divided TID | 300 mg QD divided TID | 300 mg QD divided TID | 300 mg QD divided TID | 300 mg QD divided TID | 300 mg QD divided TID | . . . |

TABLE 9

Pre-Treatment Schedule for Treatment Prior To Extreme Physiological and/or Psychological Stress Oral Dosing Medication Taper Sample Schedule

|  | Day-2 | Day-1 | Day of Stressor (Post) | Day 1 | Day 2-7 | Week 2 |
|---|---|---|---|---|---|---|
| Ibuprofen | — | — | 200 mg PO TID | 200 mg PO BID | 200 mg PO QD | 100 mg PO QD |
| Cannabidiol (CBD) | 300 mg QD divided TID | 300 mg QD divided TID | 300 mg QD divided TID | 300 mg QD divided TID | 300 mg QD divided TID | 300 mg QD divided TID |
| Tetrahydrocannabinol (THC) [Optional] | 10 mg PO QD | — | — | — | — | — |
| Psilocybin [Optional] | 10-15 mg PO (once, under supervision) | — | — | — | — | — |

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include, but are not limited to, physically mate-able and/or physically interacting components and/or wirelessly interactable and/or wirelessly interacting components and/or logically interacting and/or logically interactable components.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of the invention, and it is understood that such equivalent embodiments are to be included herein.

What is claimed:

1. A method for dispensing opioids in an anti-addiction pain-modulating regimen, the method comprising:
generating, by a computer system, a dosage scheme for dispensing an opioid compound, wherein the dosage scheme is based on one or more parameters associated with a health condition of a patient, wherein:
the dosage scheme includes a first dosage scheme for an opioid compound and a first dosage scheme for a cannabinoid compound to be administered to the patient concurrently over a period of time; and
the first dosage scheme for the opioid compound includes a first plurality of dosages with a decreasing amount of an active ingredient in the opioid compound over the period of time;
determining an addiction risk score for the patient based on the dosage scheme;
determining, by the computer system, whether to adjust the dosage scheme based on the addiction risk score for the patient;
in response to determining to adjust the dosage scheme, generating, by the computer system, an adjusted dosage scheme based on the addiction risk score, wherein:
the adjusted dosage scheme includes a second dosage scheme for the opioid compound that is different from the first dosage scheme for the opioid compound to be administered to the patient;
sending the second dosage scheme to a dispensing container, wherein the dispensing container is configured to allow the patient to access a dosage of the opioid compound according to the second dosage scheme.

2. The method of claim 1, further including:
receiving, by the computer system, pain level indicators associated with the patient, wherein the pain level indicators include:
a first pain level indicator based on an input from the patient; and
a second pain level indicator based on biometric data obtained by a wearable device configured to be worn by the patient, and
determining, by the computer system, whether to adjust at least one of the dosage schemes or the adjusted dosage scheme based on the pain level indicators.

3. The method of claim 2, further comprising:
determining, based on the received pain level indicators, at least one relationship between pain-reduction efficacy of the cannabinoid compound and pain-reduction efficacy of the opioid compound,
wherein the adjusted dosage scheme is generated based on the determined at least one relationship and has a predicted pain score that less than a maximum pain score.

4. The method of claim 2, further including:
in response to receiving the pain level indicators associated with the patient, transmitting, by the computer system to a user device associated with the patient, instructions to administer the opioid compound and the cannabinoid compound to the patient in accordance with the adjusted dosage scheme.

5. The method of claim 1, wherein the first dosage scheme for the cannabinoid compound includes a second plurality of dosages with an increasing amount of an active ingredient in the cannabinoid compound over the period of time.

6. The method of claim 1, wherein the dosage scheme further includes a third dosage scheme for a pain relief medication to be administered to the patient concurrently.

7. The method of claim 1, further including:
unlocking a first compartment to allow the patient to access a first set of dosages of the opioid compound and a first set of dosages of the cannabinoid compound in accordance with the dosage scheme; and
unlocking a first compartment to allow the patient to access a second set of dosages of the opioid compound and a second set of dosages of the cannabinoid compound in accordance with the adjusted dosage scheme.

8. The method of claim 1, wherein the opioid compound and the cannabinoid compound comprise pills, capsules, tablets, transdermal patches, injections, tinctures, smokable herbs, or inhalable vapor source.

9. The method of claim 1, wherein the dosage scheme and the adjusted dosage scheme are configured to gradually reduce or increase the opioid compound from the pain-modulating regimen of the patient by replacing the opioids with the cannabinoid compound.

10. The method of claim 1, further including:
determining, by the computer system, whether an amount of opioid administered to the patient in accordance with the dosage scheme or the adjusted dosage scheme is above a threshold limit; and
reducing the amount of opioid in the dosage scheme in an instance where the amount of opioid is above the threshold limit.

11. The method of claim 1, further including:
generating the adjusted dosage scheme partially based on an input received from a user of the computer system;
determining, by the computer system, whether an amount of opioid administered to the patient in accordance with the adjusted dosage scheme is above a threshold limit; and
in response to determining that the amount of opioid administered to the patient in accordance with the adjusted dosage scheme is above the threshold limit, providing, by the computer system, a threshold exceeded indication to the user.

12. The method of claim 1, wherein the dispenser container includes:
a controller programmable according to the adjusted dosage scheme; and
locked compartments storing the opioid compound; and wherein:
the dispenser system is configured to unlock one or more of the compartments to allow a patient to access the dosage of the opioid compound held in the one or more compartments.

13. The method of claim 12, wherein the controller stores one or more authentication programs and is programmed to authenticate the patient using the one or more authentication programs, and the dispensing container is configured to unlock the one or more of the compartments in response to authenticating the patient.

14. The method of claim 13, wherein authentication the patient comprises:
acquiring biometric information from the patient, and
comparing the biometric information with reference biometric information associated with the patient, wherein biometric information comprises a fingerprint, voice, facial features, or retina data.

15. The method of claim 13, wherein the controller is further programmed to perform the authentication of the patient and unlocking of the one or more compartments at a particular time of a day that is predefined based on the adjusted dosage scheme.

16. A system for dispensing opioids in an anti-addiction pain-modulating regimen, the system comprising:
a computer system configured to:
generate a dosage scheme for dispensing an opioid compound, wherein the dosage scheme is based on one or more parameters associated with a health condition of a patient, wherein:
the dosage scheme includes a first dosage scheme for an opioid compound and a first dosage scheme for a cannabinoid compound to be administered to the patient concurrently over a period of time; and
the first dosage scheme for the opioid compound includes a first plurality of dosages with a decreasing amount of an active ingredient in the opioid compound over the period of time;
determine an addiction risk score for the patient based on the dosage scheme;
determine by the computer system, whether to adjust the dosage scheme based on the addiction risk score for the patient;
in response to determining to adjust the dosage scheme, generate an adjusted dosage scheme based on the addiction risk score, wherein:
the adjusted dosage scheme includes a second dosage scheme for the opioid compound that is different from the first dosage scheme for the opioid compound to be administered to the patient;
send the second dosage scheme to a dispensing container, wherein the dispensing container is configured to allow the patient to access a dosage of the opioid compound according to the second dosage scheme.

17. The system of claim 16, wherein the dispenser container includes:
a controller programmable according to the adjusted dosage scheme; and
locked compartments storing the opioid compound; and wherein:
the dispenser system is configured to unlock one or more of the compartments to allow a patient to access the dosage of the opioid compound held in the one or more compartments.

18. The system of claim 17, wherein the controller stores one or more authentication programs and is programmed to authenticate the patient using the one or more authentication programs, and the dispensing container is configured to unlock the one or more of the compartments in response to authenticating the patient.

19. The system of claim 18, wherein authentication the patient comprises:
acquiring biometric information from the patient, and
comparing the biometric information with reference biometric information associated with the patient, wherein biometric information comprises a fingerprint, voice, facial features, or retina data.

20. A method for dispensing compounds in an anti-addiction pain-modulating regimen, the method comprising:
generating, by a computer system, a dosage scheme for dispensing a first compound, wherein the dosage scheme is based on one or more parameters associated with a health condition of a patient, wherein:
the dosage scheme includes a first dosage scheme for the first compound and a first dosage scheme for a cannabinoid compound to be administered to the patient concurrently over a period of time;
the first dosage scheme for the first compound includes a first plurality of dosages with a decreasing amount of an active ingredient in the first compound over the period of time; and
the first dosage scheme is for pre-treatment of the patient prior to a surgery or physiological or psychological stress;
determining an addiction risk score for the patient based on the dosage scheme;
determining, by the computer system, whether to adjust the dosage scheme based on the addiction risk score for the patient;
in response to determining to adjust the dosage scheme, generating, by the computer system, an adjusted dosage scheme based on the addiction risk score, wherein:
the adjusted dosage scheme includes a second dosage scheme for the first compound that is different from the first dosage scheme for the first compound to be administered to the patient;

sending the second dosage scheme to a dispensing container, wherein
the dispensing container is configured to allow the patient to access a dosage of the first compound according to the second dosage scheme.

* * * * *